US012773513B2

(12) United States Patent
Romagnoli et al.

(10) Patent No.: US 12,773,513 B2
(45) Date of Patent: Oct. 27, 2026

(54) TEXTILE MASK SYSTEMS

(71) Applicant: ResMed Pty Ltd, Bella Vista (AU)

(72) Inventors: Jose Ignacio Romagnoli, Sydney (AU); Julian Ross Lombardo, Sydney (AU); Jessica Lea Dunn, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 133 days.

(21) Appl. No.: 17/948,511

(22) Filed: Sep. 20, 2022

(65) Prior Publication Data

US 2023/0014701 A1 Jan. 19, 2023

Related U.S. Application Data

(63) Continuation of application No. 16/387,893, filed on Apr. 18, 2019, now Pat. No. 11,452,832, which is a continuation of application No. 14/131,737, filed as application No. PCT/AU2012/000836 on Jul. 12, 2012, now Pat. No. 10,300,235.

(Continued)

(51) Int. Cl.

*A61M 16/06* (2006.01)
*A61M 16/08* (2006.01)

(52) U.S. Cl.

CPC ........ *A61M 16/0605* (2014.02); *A61M 16/06* (2013.01); *A61M 16/0611* (2014.02); *A61M 16/0666* (2013.01); *A61M 16/0683* (2013.01); *A61M 16/0875* (2013.01); *A61M 16/0616* (2014.02); *A61M 16/0622* (2014.02); *A61M 16/0816* (2013.01); *A61M 16/0825* (2014.02);

(Continued)

(58) Field of Classification Search

CPC .... A41D 13/11–1192; A61M 16/0605; A61M 16/06; A61M 16/0611; A61M 16/0666; A61M 16/0683; A61M 16/0875; A61M 16/0616; A61M 16/0622; A61M 16/0816; A61M 16/0825; A61M 2207/00; A61M 2210/0618; A61M 16/0688

USPC ............ 128/206.24, 207.13, 206.21, 206.27, 128/207.11, 206.28, 207.18, 206.12, 128/206.18, 207.17, 205.25

See application file for complete search history.

(56) References Cited

U.S. PATENT DOCUMENTS

| | | | |
|---|---|---|---|
| 3,682,171 | A | 8/1972 | Dali et al. |
| 3,750,665 | A | 8/1973 | Stranicky |

(Continued)

FOREIGN PATENT DOCUMENTS

| | | | |
|---|---|---|---|
| AU | 4683797 | A | 7/1998 |
| AU | 715075 | B2 | 1/2000 |

(Continued)

OTHER PUBLICATIONS

Notice of Reasons for Rejection and English translation thereof mailed Apr. 5, 2021 in corresponding JP Application p. 2020-017965 (7 pages).

(Continued)

*Primary Examiner* — Elliot S Ruddie

(74) *Attorney, Agent, or Firm* — Nixon & Vanderhye P.C.

(57) ABSTRACT

A mask system for providing pressurized breathable gas includes at least one panel and a seal member, wherein the panel comprises a textile. The panel defines a cavity adapted to receive a patient's nose. The seal member is adapted to sealingly engage with the patient's face. The panel and seal member may be integrally formed in one piece.

20 Claims, 49 Drawing Sheets

Related U.S. Application Data

(60) Provisional application No. 61/457,935, filed on Jul. 12, 2011.

(52) U.S. Cl.
CPC . *A61M 2207/00* (2013.01); *A61M 2210/0618* (2013.01)

(56) References Cited

U.S. PATENT DOCUMENTS

| | | | | |
|---|---|---|---|---|
| 4,458,679 | A | 7/1984 | Ward | |
| 4,782,832 | A | 11/1988 | Trimble et al. | |
| 5,724,965 | A * | 3/1998 | Handke | A61M 16/0605 128/207.18 |
| 6,019,101 | A | 2/2000 | Cotner | |
| 6,044,844 | A | 4/2000 | Kwok et al. | |
| 6,494,207 | B1 | 12/2002 | Kwok | |
| 6,631,718 | B1 | 10/2003 | Lovell | |
| 7,036,508 | B2 | 5/2006 | Kwok | |
| 7,461,656 | B2 | 12/2008 | Guanaratnam | |
| 7,779,832 | B1 | 8/2010 | Ho | |
| 7,845,352 | B2 | 12/2010 | Sleeper et al. | |
| 8,146,597 | B2 | 4/2012 | Kwok et al. | |
| 10,300,235 | B2 | 5/2019 | Romagnoli et al. | |
| 2002/0005198 | A1 | 1/2002 | Kwok et al. | |
| 2002/0117177 | A1 | 8/2002 | Kwok | |
| 2003/0145857 | A1 | 8/2003 | Sullivan et al. | |
| 2003/0196657 | A1 | 10/2003 | Ging | |
| 2004/0094159 | A1 | 5/2004 | Kwok et al. | |
| 2004/0226566 | A1* | 11/2004 | Gunaratnam | A61M 16/0825 128/207.18 |
| 2006/0027237 | A1 | 2/2006 | Sleeper et al. | |
| 2006/0102184 | A1 | 5/2006 | Kullik et al. | |
| 2006/0231103 | A1 | 10/2006 | Matula et al. | |
| 2006/0283461 | A1 | 12/2006 | Lubke | |
| 2007/0163594 | A1 | 7/2007 | Ho | |
| 2007/0175479 | A1 | 8/2007 | Kemmer et al. | |
| 2007/0209663 | A1 | 9/2007 | Marque et al. | |
| 2007/0267021 | A1 | 11/2007 | Kwok | |
| 2008/0047560 | A1* | 2/2008 | Veliss | A61M 16/0611 128/207.11 |
| 2008/0060649 | A1* | 3/2008 | Veliss | A61M 16/0616 128/207.18 |
| 2008/0142015 | A1* | 6/2008 | Groll | A61M 16/0683 128/206.24 |
| 2008/0230067 | A1 | 9/2008 | Kwok et al. | |
| 2008/0264422 | A1 | 10/2008 | Fishman | |
| 2009/0120442 | A1 | 5/2009 | Ho | |
| 2010/0282265 | A1 | 11/2010 | Melidis | |
| 2010/0294281 | A1 | 11/2010 | Ho | |
| 2011/0048426 | A1 | 3/2011 | Sleeper et al. | |
| 2011/0088699 | A1 | 4/2011 | Skipper | |
| 2011/0162654 | A1 | 7/2011 | Carroll et al. | |
| 2011/0174310 | A1 | 7/2011 | Burz et al. | |
| 2011/0247628 | A1 | 10/2011 | Ho | |
| 2011/0253144 | A1 | 10/2011 | Groll | |
| 2012/0055485 | A1 | 3/2012 | Anthony | |
| 2012/0152255 | A1 | 6/2012 | Barlow | |
| 2014/0158136 | A1 | 6/2014 | Romagnoli | |
| 2019/0240436 | A1 | 8/2019 | Romagnoli et al. | |

FOREIGN PATENT DOCUMENTS

| | | | | |
|---|---|---|---|---|
| AU | 2008323541 | | 5/2009 | |
| AU | 2008323541 | A1 | 5/2009 | |
| AU | 2009215562 | A1 | 8/2009 | |
| AU | 2009215562 | B2 | 11/2011 | |
| CA | 2716038 | A1 | 8/2009 | |
| CN | 1177929 | A | 4/1998 | |
| CN | 1623609 | A | 6/2005 | |
| CN | 101076376 | A | 11/2007 | |
| CN | 101516427 | A | 8/2009 | |
| CN | 101687085 | | 3/2010 | |
| CN | 101861180 | A | 10/2010 | |
| CN | 102046233 | A | 5/2011 | |
| CN | 102264424 | A | 11/2011 | |
| CN | 102281925 | A | 12/2011 | |
| CN | 101076376 | B | 6/2012 | |
| DE | 20201005143 | U1 | 8/2010 | |
| EP | 1778365 | A2 | 5/2007 | |
| EP | 2147769 | A1 | 1/2010 | |
| EP | 2219719 | A1 | 8/2010 | |
| EP | 2303379 | A1 | 4/2011 | |
| EP | 2 359 888 | | 8/2011 | |
| EP | 4819047 | | 9/2011 | |
| EP | 2379148 | A1 | 10/2011 | |
| EP | 2444113 | A2 | 4/2012 | |
| EP | 2379148 | | 10/2016 | |
| EP | 2219719 | | 12/2017 | |
| GB | 2470172 | A | 11/2010 | |
| GB | 2470172 | B | 8/2011 | |
| GB | 2481887 | A | 1/2012 | |
| GB | 2481887 | B | 9/2012 | |
| JP | 2002-102352 | | 4/2002 | |
| JP | 2004-530480 | | 10/2004 | |
| JP | 2005-40589 | | 2/2005 | |
| JP | 2005-537906 | | 12/2005 | |
| JP | 2007-508917 | | 4/2007 | |
| JP | 2008-502380 | | 1/2008 | |
| JP | 2008507343 | A | 3/2008 | |
| JP | 2008-526392 | | 7/2008 | |
| JP | 2009-544371 | | 12/2009 | |
| JP | 2009-545408 | | 12/2009 | |
| JP | 2010-507405 | | 3/2010 | |
| JP | 2011-500229 | | 1/2011 | |
| JP | 2011-502657 | | 1/2011 | |
| JP | 2011502657 | A | 1/2011 | |
| JP | 2011143255 | A | 7/2011 | |
| JP | 2011519284 | A | 7/2011 | |
| JP | 4819047 | B2 | 11/2011 | |
| JP | 2012513229 | A | 6/2012 | |
| JP | 2012-515562 | | 7/2012 | |
| JP | 2012-528608 | | 11/2012 | |
| JP | 2013-501541 | | 1/2013 | |
| WO | WO 2000/050121 | A1 | 8/2000 | |
| WO | WO 2005/032634 | A1 | 4/2005 | |
| WO | WO 2006/014630 | A2 | 2/2006 | |
| WO | WO 2006/074514 | | 7/2006 | |
| WO | WO 2007/045023 | A1 | 4/2007 | |
| WO | WO 2007/089553 | A2 | 8/2007 | |
| WO | WO 2008/011682 | | 1/2008 | |
| WO | WO 2008/011683 | | 1/2008 | |
| WO | WO-2008011682 | A1 * | 1/2008 | A61M 16/06 |
| WO | WO 2008/019294 | | 2/2008 | |
| WO | 2009/026627 | A1 | 3/2009 | |
| WO | WO 2009/062265 | A1 | 5/2009 | |
| WO | WO 2009/105528 | A2 | 8/2009 | |
| WO | 2009-291615 | | 12/2009 | |
| WO | WO 2009/143586 | A1 | 12/2009 | |
| WO | WO 2010/009877 | A1 | 1/2010 | |
| WO | 2010/016774 | A1 | 2/2010 | |
| WO | 2010/067235 | A1 | 6/2010 | |
| WO | US 2007/0209663 | | 6/2010 | |
| WO | WO 2010/073138 | A1 | 7/2010 | |
| WO | WO 2010125074 | A1 | 11/2010 | |
| WO | WO 2010139014 | A1 | 12/2010 | |
| WO | WO 2011/017763 | | 2/2011 | |
| WO | WO 2011/022779 | | 3/2011 | |
| WO | WO 2013/006913 | A1 | 1/2013 | |

OTHER PUBLICATIONS

European Search Report mailed Aug. 20, 2020 in corresponding EP Application 201716586.

JP Notice of Allowance mailed Jan. 6, 2020 in corresponding JP Application p. 2018-184364.

NZ First Examination Report mailed Feb. 17, 2020 in corresponding NZ Application 761226.

JP Notice of Reasons for Rejection and English translation thereof mailed Aug. 9, 2019 in corresponding JP Application p. 2018-184364.

(56) References Cited

OTHER PUBLICATIONS

CN Notification of the Second Office Action and English translation thereof mailed August 21, 2019 in corresponding CN Application 201710312263.X.
International Search Report issued in International Patent Application No. PCT/AU2012/000836, mailed Nov. 27, 2012.
Written Opinion of the International Searching Authority issued in International Patent Application No. PCT/AU2012/000836, mailed Nov. 27, 2012.
International Preliminary Report on Patentability issued in International Patent Application No. PCT/AU2012/000836, mailed Nov. 11, 2013.
First Office Action issued Mar. 22, 2019 in a corresponding Chinese Application No. 201710312263.X, and an English translation thereof (22 pages).
A First Examination Report issued in corresponding New Zealand Application No. 745367, dated Aug. 27, 2018 (3 pages).
A Second Office Action issued Apr. 2, 2018, in a corresponding Japanese Patent Application No. 2014-519348 (5 pages), and an English translation thereof (9 pages).
A First Office Action issued Apr. 2, 2018, in a corresponding Japanese Patent Application No. 2017-95411 (3 pages), and an Enlish translation thereof (5 pages).
A Communication dated Oct. 27, 2017, forwarding an Extended European Search Report in European Patent Application No. EP 171782758 (8 pages).
A Pre-Appeal Examination Report dated Jul. 4, 2017, in a corresponding Japanese Application No. JP 2014-519348 (3 pages), and an English translation thereof (4 pages).
A First Examination Report issued Mar. 22, 2017, in a corresponding New Zealand Application No. 728994 (3 pages).
Decision of Rejection issued Jan. 16, 2017, in a corresponding Japanese Application No. 2014-519348 (3 pages) and an English translation thereof (5 pages).
Third Office Action issued Nov. 1, 2016 in a corresponding Chinese Application No. 2012800441380 (10 pages), and an English translation thereof (12 pages).
Communication Pursuant to Article 94(3) EPC issued Jul. 21, 2016 in a corresponding European Application No. 12 810 931.1-1662 (5 pages).
First Office Action issued May 9, 2016 in a corresponding Japanese Application No. 2014-519348 (19 pages) and an English translation thereof (15 pages).
Office Action issued Jun. 9, 2022 in corresponding EP Application No. 20171658.6 (6 pages).
Second Office Action issued Apr. 25, 2016 in a corresponding Chinese Application No. 201280044138.0 (14 pages) and an English translation thereof (14 pages).
Office Action issued Jul. 11, 2022 in corresponding JP Appl. No. 2021-132746, and English translation (10 pages).
First Examination Report issued Sep. 11, 2015 in a corresponding New Zealand Application No. 711886 (3 pages).
Further Examination Report issued Sep. 11, 2015 in a corresponding New Zealand Application No. 619627 (2 pages).
Office Action issued Aug. 11, 2015 in a corresponding Chinese Application No. 2012800441380 (15 pages) and English translation thereof (16 pages).
Patent Examination Report No. 3 issued May 20, 2015 in corresponding Australian Patent Application No. 2012283758 (4 pages).
Supplementary European Search Report issued Oct. 31, 2014 in corresponding European Patent Application No. EP 12 81 0931.
First Examination Report dated Jul. 28, 2014 in New Zealand Application No. 619627 (2 pages).
Patent Examination Report No. 1 issued Jul. 15, 2014 in corresponding Australian Application No. 2012283758.
First Office Action with English Translation in corresponding CN Application No. 202310045913.4, 28 pages, dated Jan. 22, 2025.
First Office Action in corresponding U.S. Appl. No. 18/982,808, 15 pages, dated Mar. 5, 2025, citing U.S. Pat. No. 1,702,400 (Drager), U.S. Pat. No. 2,818,066 (Glidden), U.S. Pat. No. 11,452,832 (Romagnoli), US 2007/0125386 (Quinn), US 2023/0014701 (Romagnoli).
Second Office Action with English Translation in corresponding CN Application No. 202310045913.4, 23 pages, dated Jul. 26, 2025.
Decision on Rejection Office Action with English Translation in corresponding Chinese Application No. 2023100456913.4 dated Mar. 20, 2026. (18 pages).

* cited by examiner

TEXTILE MASK SYSTEMS

CROSS-REFERENCE TO APPLICATION

This application is a continuation of U.S. patent application Ser. No. 16/387,893 filed Apr. 18, 2019, issued as U.S. Pat. No. 11,452,832, which is a continuation of U.S. patent application Ser. No. 14/131,737, filed Jan. 9, 2014, issued as U.S. Pat. No. 10,300,235, which is the U.S. national phase of International Application No. PCT/AU2012/000836, filed Jul. 12, 2012, which designated the U.S. and claims the benefit of U.S. Provisional Application No. 61/457,935, filed Jul. 12, 2011, the entire contents of each of which are hereby incorporated herein by reference.

FIELD OF THE TECHNOLOGY

The present technology relates to a nasal mask system used for treatment, e.g., of Sleep Disordered Breathing (SDB) with Continuous Positive Airway Pressure (CPAP) or Non-Invasive Positive Pressure Ventilation (NIPPV).

BACKGROUND OF THE TECHNOLOGY

Patient interfaces, such as a full-face or nasal mask systems, for use with blowers and flow generators in the treatment of Sleep Disordered Breathing (SDB), including sleep apnea, typically include a soft face-contacting portion, such as a cushion, and a rigid or semi-rigid shell or frame. In use, the interface is held in a sealing position by headgear so as to enable a supply of air at positive pressure (e.g., 2-30 cm $H_2O$) to be delivered to the patient's airways.

One factor in the efficacy of therapy and compliance of patients with therapy is the comfort and fit of the patient interface.

The present technology provides alternative arrangements of mask systems to enhance the efficacy of therapy and compliance of patients with therapy.

SUMMARY OF TECHNOLOGY

One aspect of the present technology relates to a mask constructed of a textile.

Another aspect of the present technology relates to a mask constructed of a textile composite and a seal member. The seal member may be constructed of a polymer.

Another aspect of the present technology relates to a mask constructed of a textile composite and a seal member. The seal member may be constructed of a polymer, wherein the polymer is tacky.

Another aspect of the present technology relates to a mask constructed of a first textile composite and a second textile composite.

Another aspect of the present technology relates to a mask constructed of a first textile composite and a second textile composite. The first textile composite and second textile composite are sealingly engaged.

Another aspect of the present technology relates to a mask constructed of a first textile composite and a second textile composite. The first textile composite and second textile composite are sealingly engaged along a perimeter surface using a welding process. The welding process may be radiofrequency or ultrasonic welding.

Another aspect of the present technology relates to a mask constructed of a first textile composite and a second textile composite, and the first textile composite and second textile composite are sealingly engaged along a perimeter surface using a radiofrequency weld or ultrasonic weld. The perimeter surface may be arranged in a three dimensional form.

Another aspect of the present technology relates to a mask constructed of a textile arranged in a dome shape.

Another aspect of the present technology relates to a mask constructed of a textile arranged in a positive Gaussian curvature.

Another aspect of the present technology relates to a mask constructed of a textile, the textile having a curvature, the curvature substantially defined by a rigidized frame.

Another aspect of the present technology relates to a mask constructed of a textile, the textile may be crushable or deformable under force applied by a human hand or finger pressure.

Another aspect of the present technology relates to a mask constructed of a wall, the wall not able to support its own weight. The wall may be substantially floppy. The wall may be substantially non-resilient. The wall may be formed of a textile. The wall may have a hand of one or more of the following terms: drapable, rough, fibrous, coarse, silky, soft, flexible, warm, non-clammy. The wall may be a material having the feel of a textile. The wall may be opaque, or substantially non-translucent.

Another aspect of the present technology relates to a mask including a wall, the wall not able to support its own weight. The wall may be formed of a textile. The wall may be attached to a sealing portion, preferably the sealing portion supports the wall. The sealing portion may be formed of a polymer such as silicone.

Another aspect of the present technology relates to a mask including a substantially non-rigid, substantially non-resilient wall, the wall constructed of a textile. In use, the wall is preferably shaped to accommodate a patient's face by one or a combination of: activation of positive pressure, darts in the wall, resilient seal structure, rigidized frame.

Another aspect of the present technology relates to a mask having a substantially inextensible, substantially non-resilient textile wall. The textile wall may be connected to a resilient seal member.

Another aspect of the present technology relates to a mask having a combination of at least one semi-rigid, flexible and/or resilient support member, and a substantially inextensible, substantially non-resilient textile wall. In use the support member allows the mask structure to unfold, e.g. from a first folded state to a second unfolded state. Preferably, the mask may also include at least one substantially rigid connection member adapted to receive an air delivery conduit. Preferably, the t least one substantially rigid connection member may include a vent.

Another aspect of the present technology relates to a mask including a wall or shell, the wall or shell constructed and arranged to have a predefined shape, the wall or shell being made from a non-rigid element; and a support beam adapted to conform to the patient's upper lip region, the support beam adapted to support its own weight, the support beam may also be substantially inextensible.

Another aspect of the present technology relates to a mask including a textile shell, the textile shell connected to or otherwise formed with a rigidizer, the rigidizer having a length that is greater than its width and/or thickness. Preferably the rigidizer is positioned over the patient's upper lip. Preferably, the rigidizer is not positioned over the patient's nasal bridge. Preferably, the rigidizer anchors and/or positions other rigid elements with respect to one another, e.g., one or more cuffs, a vent portion, an annular elbow connection.

Another aspect of the present technology relates to a mask constructed of a first textile composite and a second textile composite, and the first textile composite and second textile composite are sealingly engaged along a perimeter surface. The first and second textile composite may form a cavity.

Another aspect of the present technology relates to a mask constructed of a textile composite. The textile composite may comprise a fabric and a polymer.

Another aspect of the present technology relates to a mask constructed of a combination of textile and polymer. The mask may comprise a chamber forming portion including a seal member. The chamber forming portion may be comprised of a composite textile comprising a fabric and a polymer. The seal member may be comprised of a polymer. The polymer may be a low hardness polymer such as a silicone having a Shore A hardness of 5-20.

Another aspect of the present technology relates to a mask constructed of a textile composite. The mask may further comprise a one or more cuffs. The cuff(s) may be arranged to receive a supply of breathable gas from an air delivery tube. The cuff(s) may be adapted to sealingly engage with the textile. The cuff(s) may also be removably attachable. Further, the cuff(s) may be welded to the textile. The cuff(s) may be sealable by placing a plug in the cuff. The cuff(s) may include male and/or female connectors. The cuff(s) may include a venting portion adapted to vent expired exhaust gases. For example, one cuff may receive incoming air and another cuff may exhaust expired gases.

Another aspect of the present technology relates to a mask system for delivering pressurized breathable gas to a patient. The mask system comprises a chamber forming portion including 1) at least one panel at least partially delimiting a cavity adapted to receive a nose of a patient, the at least one panel including a first panel having an opening formed therein through which the patient's nose is received into the cavity; and 2) a seal member formed as part of or coupled to the first panel and adapted to sealingly engage the patient's face, wherein the first panel comprises a textile and the seal member comprises a polymer.

Another aspect of the present technology relates to a mask system for delivering pressurized breathable gas to a patient. The mask system comprises a chamber forming portion including a back panel at least partially delimiting a cavity adapted to receive a patient's nose, the back panel including an upper panel coupled to a lower panel such that an opening is formed between the upper panel and the lower panel, the opening configured such that the patient's nose is received into the cavity through the opening, wherein the upper panel has an upper seal portion configured to seal against the patient's external nares, and the lower portion has a lower seal portion configured to seal against the patient's upper lip.

Another aspect of the present technology relates to a tube management system for reducing drag on a tube arranged to deliver breathable gas to a chamber forming portion positioned on a patient's face in sealing engagement therewith. The tube management system comprises headgear to support the chamber forming portion on the patient's face, the headgear including an anchor member provided towards a rear of the patient's head (e.g., below the occiput, adjacent the nape, or below the ear) and configured to receive the tube to reduce or prevent disruptive forces exerted on the chamber forming portion by the tube.

Another aspect of the present technology relates to a headgear for supporting a patient interface (e.g., a mask) on a patient's face, the patient interface arranged to be positioned adjacent the patient's nose in sealing communication with at least one of the patient's airways. The headgear consists essentially of a single strap coupled to the mask and extending from a first portion of the mask to a second portion of the mask.

Another aspect of the present technology relates to a mask for use in respiratory therapy. The mask comprises a seal adapted to surround and sealingly engage a patient's airway; a cushion adapted to support the seal; and an enclosing portion adapted to form a chamber with the seal and the cushion, wherein the seal is adapted to stretch over the patient's nose bridge, and the enclosing portion is formed of a textile.

Another aspect of the present technology relates to a mask for a respiratory device. The mask comprises a seal forming portion adapted to stretch over the patient's nose bridge; a cushion portion constructed and arranged to match the contours of the patient's face; and a chamber forming portion constructed of a textile and adapted to flex around the patient's face.

Another aspect of the present technology relates to a mask for use in treating sleep disordered breathing. The mask comprises a chamber constructed from a textile; a cuff adapted to connect with an air delivery tube; and a rigid element adapted to support the chamber in position on the patient's face, the rigid element formed integrally with the cuff (e.g., in one piece).

Another aspect of the present technology relates to a mask adapted for use in the treatment of sleep disordered breathing. The mask comprises a chamber constructed of a textile, wherein the textile includes darts constructed and arranged to shape the textile in a three dimensional form.

Another aspect of the present technology relates to a mask adapted for use in the treatment of sleep apnea. The mask comprises a chamber forming structure constructed of a textile; a support beam; at least one cuff; and a vent, wherein the support beam, the at least one cuff and the vent are formed in one piece.

Other aspects, features, and advantages of the present technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various embodiments of the technology. In such drawings:

FIG. 1-2 is a side view of the nasal mask system of FIG. 1 removed from the patient's face;

FIG. 1-3 is a first perspective view of the nasal mask system of FIG. 1-2;

FIG. 1-4 is a second perspective view of the nasal mask system of FIG. 1-2;

FIG. 1-5 is a rear view of the nasal mask system of FIG. 1-2;

FIG. 1-6 is a front view of the nasal mask system of FIG. 1-2;

FIG. 1-7 is a top view of the nasal mask system of FIG. 1-2;

FIG. 1-8 is a bottom view of the nasal mask system of FIG. 1-2;

FIG. 1-9 is a first exploded perspective view of the nasal mask system of FIG. 1-2;

FIG. 1-10 is a second exploded perspective view of the nasal mask system of FIG. 1-2;

FIG. 1-11 is a cross-sectional view along the line 1-11-1-11 in FIG. 1-5;

FIG. 1-12 is a perspective view of the cross-section along the line 1-12-1-12 in FIG. 1-5;

FIG. 1-13 is a side view of a cross-section along a line similar to the line 1-12-1-12 in FIG. 1-5;

FIG. 2-1 is a front view of a back panel and a sealing member positioned on a patient's face in accordance with an example of the disclosed technology;

FIG. 2-2 is a perspective view of the back panel and sealing member of FIG. 2-1;

FIG. 3-1 is a vertical cross-section of a mask according to an example of the disclosed technology;

FIG. 3-1A is a horizontal cross-section of the mask of FIG. 3-1 shown positioned on a patient's face according to an example of the disclosed technology;

FIG. 3-2 is a horizontal cross-section of a mask positioned on a patient's face according to an example of the disclosed technology;

FIG. 4-1 is a vertical cross-section of a mask according to an example of the disclosed technology;

FIG. 4-1A is a horizontal cross-section of the mask of FIG. 4-1 shown positioned on a patient's face according to an example of the disclosed technology;

FIG. 5-1 is a perspective view of a mask having a raised section according to an example of the disclosed technology;

FIG. 5-2 is a perspective view of a portion of the mask of FIG. 5-1;

FIG. 5-2A shows the mask portion of FIG. 5-2 positioned on a patient's face in accordance with an example of the disclosed technology;

FIG. 5-3 is a schematic representation showing a partial cross-section of a mask being positioned on a patient's face in accordance with an example of the disclosed technology;

FIG. 5-4 is a horizontal cross-section of a mask positioned on a patient's face according to an example of the disclosed technology;

FIG. 5-5 is a partial cross-sectional view of a mask showing padding connected to the mask according to an example of the disclosed technology;

FIG. 5-6 is a partial cross-sectional view of a mask showing padding connected to the mask according to an example of the disclosed technology;

FIG. 5-7 is a partial cross-sectional view of a mask showing padding connected to the mask according to an example of the disclosed technology;

FIG. 5-8A is a perspective view of a mask including padding according to an example of the disclosed technology;

FIG. 5-8B is a top view of the mask of FIG. 5-8A;

FIG. 5-8C is a cross-sectional view of the mask of FIG. 5-8A positioned on a patient having a relatively shallow nose bridge height in accordance with an example of the disclosed technology;

FIG. 5-8D is a cross-sectional view of the mask of FIG. 5-8A positioned on a patient having a relatively larger nose bridge height in accordance with an example of the disclosed technology;

FIG. 6-1 is a vertical cross-section of a mask including a rigidizing element according to an example of the disclosed technology;

FIG. 7-1 is a front view of a portion of a mask including a rigidizing element according to an example of the disclosed technology;

FIG. 7-2 is a perspective view of a portion of a mask including a rigidizing element according to an example of the disclosed technology;

FIG. 7-3 is a perspective view of a portion of a mask including a rigidizing element being positioned on a patient's face according to an example of the disclosed technology;

FIG. 8-1 is a horizontal cross-section of a mask including a rigidizing element positioned on a patient's face according to an example of the disclosed technology;

FIG. 8-2 is a horizontal cross-section of a mask including a rigidizing element positioned on a patient's face according to an example of the disclosed technology;

FIG. 9 is a schematic representation of a mask positioned on a patient having a relatively narrower nose and on a patient having a relatively wider nose;

FIG. 10-1 is a perspective view of a mask system having a multi-layer seal member according to an example of the disclosed technology;

FIG. 10-2 is an exploded perspective view of a multi-layer seal member according to an example of the disclosed technology;

FIG. 11-1 shows a base layer of the seal member positioned on a patient's face according to an example of the disclosed technology;

FIG. 11-2 is a front view of the base layer of FIG. 11-1;

FIG. 11-3 is a front view showing the base layer of FIG. 11-1 being pulled into position on the patient's face according to an example of the disclosed technology;

FIG. 11-4 is a side view showing the base layer of FIG. 11-1 being pulled into position on the patient's face according to an example of the disclosed technology;

FIG. 12-1 is a front view showing the base layer and a cushioning layer of the seal member according to an example of the disclosed technology;

FIG. 12-2 shows the base layer and the cushioning layer of FIG. 12-1 positioned on a patient's face according to an example of the disclosed technology;

FIG. 12-3 is a schematic representation of a cushion including a seal member without the cushioning layer positioned on a patient's face according to an example of the disclosed technology;

FIG. 12-4 is a schematic representation of a cushion including a seal member having the cushioning layer positioned on a patient's face according to an example of the disclosed technology;

FIG. 13-1 is a front view showing the base layer, the cushioning layer and an interfacing layer of a seal member according to an example of the disclosed technology;

FIG. 13-2 is a front view of the interfacing layer of FIG. 13-1;

FIG. 13-3 is a front view showing the base layer, the cushioning layer and the interfacing layer of FIG. 13-1 being pulled into position on the patient's face according to an example of the disclosed technology;

FIG. 13-4 is a side view showing the base layer, the cushioning layer and the interfacing layer of FIG. 13-1 being pulled into position on the patient's face according to an example of the disclosed technology;

FIG. 15-1 is a perspective view of a mask system according to an example of the disclosed technology;

FIG. 15-2 shows the mask system of FIG. 15-1 being positioned on a patient's face according to an example of the disclosed technology;

FIG. 15-3 is a front view of an upper panel and a lower panel of the mask system of FIG. 15-1;

FIG. 15-4 is a front view of the upper panel of FIG. 15-3;

FIG. 15-5 is a schematic representation of the upper panel positioned on a patient's face according to an example of the disclosed technology;

FIG. 15-6 is a schematic representation of the lower panel positioned on a patient's face according to an example of the disclosed technology;

FIG. 15-7 is a front view showing the upper panel and the lower panel of FIG. 15-1 being pulled into position on the patient's face according to an example of the disclosed technology;

FIG. 16-1 is an exploded view of a mask system according to an example of the disclosed technology;

FIG. 16-2 is an exploded perspective view of a mask system according to an example of the disclosed technology;

FIG. 16-3 is a perspective view of a mask system according to an example of the disclosed technology;

FIG. 16-4 is a cross-sectional view along the line 16-4-16-4 of FIG. 16-3;

FIG. 16-5 is a cross-sectional view along the line 16-5-16-5 of FIG. 16-3;

FIG. 17-1 is a perspective view of a mask according to an example of the disclose technology;

FIG. 17-2 is a cross-section of the mask of FIG. 17-1;

FIG. 17-3 is a rear perspective view of the mask of FIG. 17-1;

FIG. 17-4 is a side view of the mask of FIG. 17-1 positioned on a patient's face according to an example of the disclosed technology;

FIG. 17-5 is a front view showing mask sections before assembly according to an example of the disclosed technology;

FIG. 18-1 is a perspective view of a mask system according to an example of the disclose technology;

FIG. 18-2 is a perspective view of a mask system according to an example of the disclose technology;

FIG. 18-3 is a cross-sectional view along the line 18-3-18-3 of FIG. 18-2;

FIG. 18-4A is a front perspective view of headgear positioned on a patient's head according to an example of the disclosed technology;

FIG. 18-4B is a side perspective view of the headgear of FIG. 18-4A;

FIG. 18-5 is a perspective view of a mask system according to an example of the disclose technology;

FIGS. 18-6A to 18-6D are perspective views of headgear according to examples of the disclosed technology;

FIG. 18-6E is an enlarged front view of the headgear fastening member of FIG. 18-6D.

FIGS. 18-7A and 18-7B are perspective views of a mask including a cushion tab;

FIG. 19-1 is a perspective view of a mask system according to an example of the disclose technology;

FIGS. 19-2 and 19-3 are front views of a partial mask system positioned on a patient's face according to an example of the disclosed technology;

FIGS. 19-4 and 19-5 are side views of a partial mask system positioned on a patient's face according to an example of the disclosed technology;

FIGS. 21-1A to 21-2 show an air delivery tube according to an example of the disclosed technology;

FIG. 21-3A is a front view of an air delivery tube according to an example of the disclosed technology;

FIG. 21-3B is an enlarged detail of a connection before an air delivery tube and a mask according to an example of the disclosed technology;

FIG. 21-4 is a cross-section of an air delivery tube according to an example of the disclosed technology;

FIGS. 21-5A to 21-5D show a process of making an air delivery tube according to an example of the disclosed technology;

FIG. 21-6A is a perspective view of an air delivery tube according to an example of the disclosed technology;

FIG. 21-6B is an end view of the air delivery tube of FIG. 21-6A;

FIG. 21-6C is a perspective view of the support structure of FIG. 21-6A;

FIG. 21-7A is a front view of a tube sheet according to an example of the disclosed technology;

FIG. 21-7B is a perspective view showing the tube sheet of FIG. 21-7A being formed into a tube according to an example of the disclosed technology;

FIG. 21-8A is a top view of a support structure according to an example of the disclosed technology;

FIG. 21-8B is an end view of an air delivery tube including the support structure of FIG. 21-8A according to an example of the disclosed technology;

FIG. 21-9 is a perspective view of a support structure according to an example of the disclosed technology;

FIG. 21-10 is a perspective view of a support structure according to an example of the disclosed technology;

FIG. 21-11 is a perspective view of a support structure according to an example of the disclosed technology;

FIG. 21-12A is a perspective view of a support structure according to an example of the disclosed technology;

FIG. 21-12B is a top view of the support structure of FIG. 21-12A; and

FIG. 21-13 is a perspective view of a support structure according to an example of the disclosed technology.

DETAILED DESCRIPTION OF ILLUSTRATED EXAMPLES

The following description is provided in relation to several examples (most of which are illustrated, some of which may not) which may share common characteristics and features. It is to be understood that one or more features of any one example may be combinable with one or more features of the other examples. In addition, any single feature or combination of features in any of the examples may constitute additional examples.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. The respiratory therapy devices or blowers described herein may be designed to pump fluids other than air.

One or more examples may include exemplary dimensions. Although specific dimensions and ranges may be provided, it is to be understood that these dimensions and ranges are merely exemplary and other dimensions and ranges are possible depending on application. For example, ranges that vary from those provided +/−10% may be suitable for particular applications.

In this specification, any reference to the term 'resilience' is defined to mean a material that is able to spring back or return to its original shape after deformation. The time for the material to return or spring back may be less than approximately 1 second.

In this specification, the handle or hand is defined to mean the quality of a fabric or yarn assessed by the reaction obtained from the sense of touch, it is concerned with the judgment of roughness, smoothness, harshness, pliability, thickness, etc.

Substantially rigid is taken to mean not readily deforming to finger pressure. Substantially non-rigid is taken to mean readily deforming to finger pressure.

1.0 Mask System

Examples of the disclosed technology are directed towards a mask system (for example, a nasal mask system) that is unobtrusive, comfortable, visually appealing, easy to fit, manufacturable in high volumes, provides an effective seal with the patient and/or fits a large majority of the population. While each example below is described as including a nasal type interface, aspects of the technology may be adapted for use with other suitable interface types, e.g. full face, oro-nasal, mouth, pillows, prongs, etc.

Figure 1:
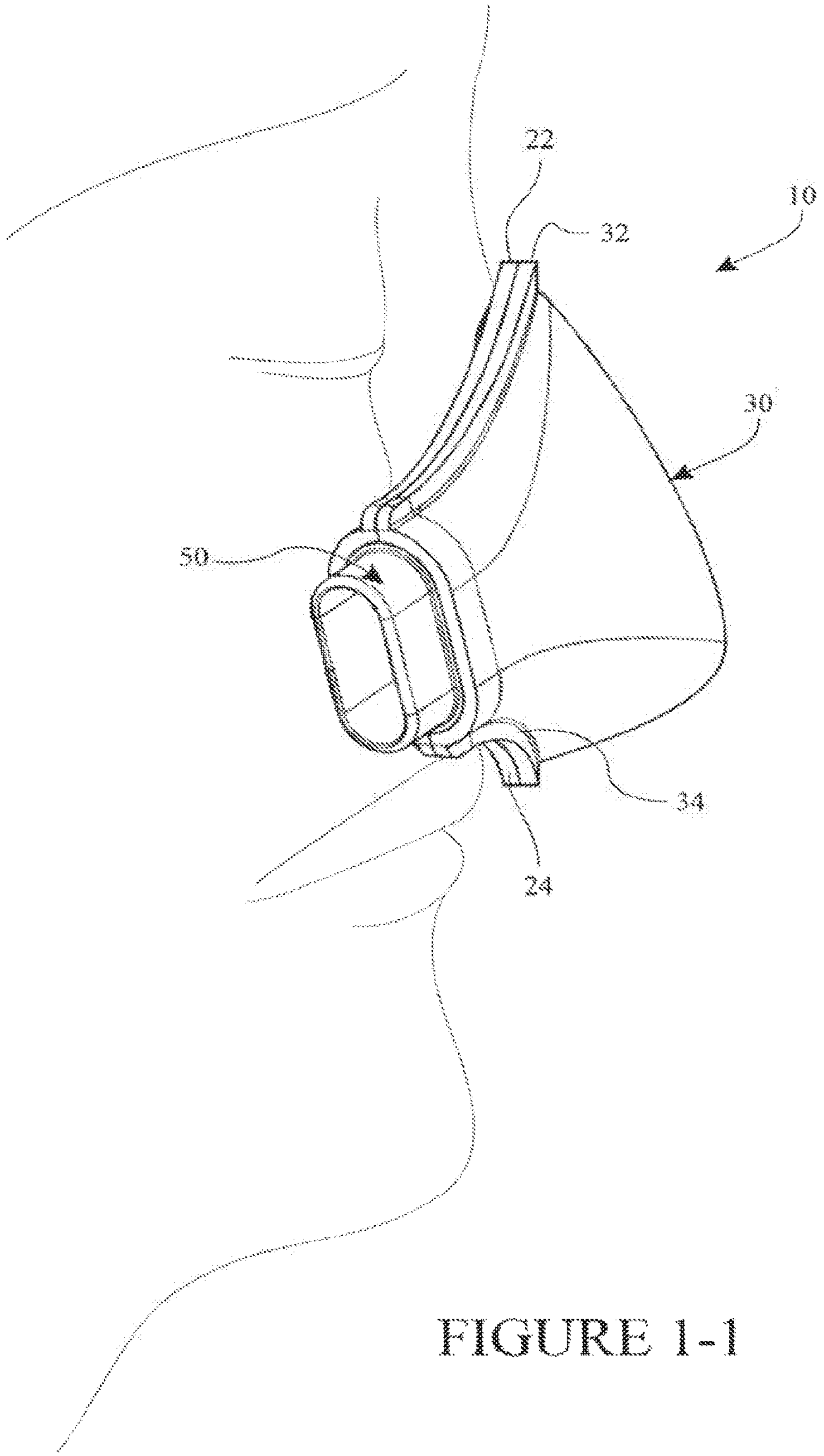
FIG. 1-1 is a side view of a nasal mask system positioned on a patient's face according to an example of the disclosed technology.
Figures 1, 2:
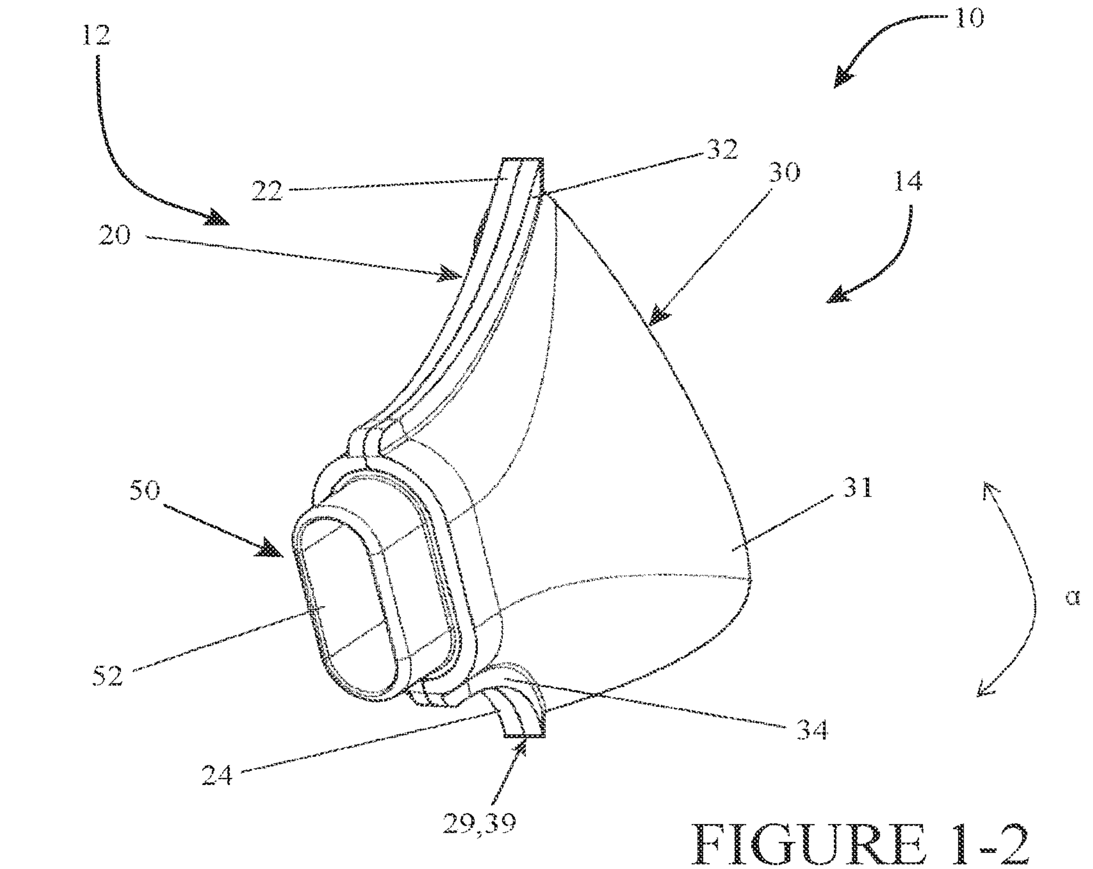

In accordance with an example of the disclosed technology shown in FIGS. 1-1 to 1-13, the mask system includes a patient interface (e.g., mask 10) adapted to engage a patient's face to seal therewith and deliver breathable gas to the patient's airways. The patient interface may form a chamber, pocket or enclosing portion adapted to deliver gases from a respiratory device to a patient's airways. As shown in FIG. 1-2, the mask 10 includes a patient contacting side 12 and a non-patient contacting side 14. As best shown in FIGS. 1-10 to 1-12, a back panel 20 and a front panel 30 are joined to form a cavity 16 which receives the patient's nose. A seal member 40 is attached to the back panel 20 and engages the patient's face to form a seal therewith.

Each side of the mask 10 may be coupled to a cuff 50. The cuffs 50 are configured to be coupled to an air delivery tube to receive a supply of breathable, pressurized gas from the air delivery tube. It will be appreciated that the mask may be coupled to only one cuff. The cuff(s) may be sealed, if required, by a plug or seal device. The mask is preferably held on the patient's face by headgear.

The back panel 20 may be constructed and arranged to be positioned near or proximal to a patient's face. The back panel 20 has a generally triangular or trapezoidal shape. Although, alternative shapes may be possible, for example elliptical, circular, square etc. Preferably, the back panel 20 is shaped to provide a visual cue to the patient as to the orientation of the mask. For example, a triangular shape tends to indicate to the patient that the apex of the back panel 20 is to be positioned at the nasal bridge region and that the sides of the back panel are to be positioned along the patient's cheeks or sides of the nose.

The back panel 20 may have a generally concave shape across the patient's face (from left to right sides of the nose). Such configuration may more readily seal with a patient's face as it is anatomically matched to the shape of a human face.

The back panel 20 includes a main body 21, an upper flange 22 along an upper perimeter of the main body and a lower flange 24 along a lower perimeter of the main body. The upper flange 22 includes an upper engaging surface 23 and the lower flange 24 includes a lower engaging surface 25. The upper engaging surface 23 and the lower engaging surface 25 sealingly engage and are coupled to corresponding surfaces of the front panel 30 to form the mask 10, as will be described later. An opening 26 is formed in the main body 21 of the back panel 20 and is configured to receive the patient's nose and permit passage of breathable gas to the patient's airways. The opening 26 may have a generally triangular shape, or any other suitable configuration.

The main body 21 of the back panel 20 preferably has a curvature from the upper flange 22 to the lower flange 24, as shown in FIGS. 1-9 and 1-10. Such curvature, together with the front panel 30, creates a space which forms the cavity 16. A left side portion and a right side portion of the main body may include cuff connecting surfaces 28 which sealingly engage the cuffs 50. The main body 21 of the back panel 20 includes an engagement portion 21-1 which sealingly engages the seal member 40, as shown in FIGS. 1-11 and 1-13.

In an alternative arrangement, the main body 21 of the back panel 20 may be substantially flat or planar and may flex or conform to the curvature of the patient's face.

As best shown in FIG. 1-10, the upper flange 22 may be angled to form a central apex that is adapted to conform to the nasal bridge region of the patient's face. The lower flange 24 may be shaped to conform to the patient's top lip and lower portion of the nose. For example, as best shown on FIG. 1-9, the lower flange 24 may comprise at least two curves or undulations 27 having a central portion 29 forming a lower extent of the undulations 27. The central portion 29 may form a convex curvature adapted to accommodate the patient's septum or philtrum region.

The back panel 20 may be constructed of a textile. Such textile may be an air holding or sealed textile that may not permit gases to pass through its fibers. For example, the textile may be a composite material having a first layer of fabric and a second layer of polymer (i.e., a coated textile). The second layer of polymer may be a film, spray coat or other arrangement adapted to seal the first layer.

Preferably the fabric is soft and conformable as the back panel 20 may contact the patient's face. Accordingly, the fabric may be a soft textile, for example cotton, satin, micro fleece, nylon, polar fleece, velvet, corduroy, etc. Bedroom friendly materials on the outer surfaces help with patient compliance as these materials increase the comfort and desirability of the mask. This also gives the mask a non-medical appearance which may be more appealing to patients. The polymer may be, for example, polyurethane, polyester, silicone, nylon, etc.

In an example, the back panel 20 has a height (for example from central portion 29 to the apex of the upper flange 22) of about 45-80 mm (e.g., 50-70 mm, or about 60 mm, or about 65 mm).

In an example, the back panel 20 may have a width (for example from one end of the lower flange 24 to the other end of the lower flange) of about 80-120 mm (e.g., 90-110 mm, or about 100 mm, or about 96 mm).

In an example, the opening 26 has a height of about 20-50 mm (e.g., 35-60 mm, or about 35 mm, or about 40 mm).

In an example, the opening has a width of about 20-50 mm (e.g., 25-45 mm, or about 35 mm).

The front panel 30 is positioned on the non-patient contacting side of the mask 10. The front panel 30 generally forms a triangular or trapezoidal shape, although other suitable shapes such as elliptical, circular, square, etc may be used. Preferably, the front panel 30 has a shape similar to the shape of the back panel 20.

As best shown in FIGS. 1-9 and 1-10, the front panel 30 includes a main body 31, an upper flange 32 along an upper perimeter of the main body and a lower flange 34 along a lower perimeter of the main body. The upper flange 32 includes an upper engaging surface 33 and the lower flange 34 includes a lower engaging surface 35. The upper engaging surface 33 and the lower engaging surface 35 sealingly engage and are coupled to the upper and lower engaging surfaces 23, 25 of the back panel 20 to form the mask 10.

The main body 31 of the front panel 30 preferably has a curvature from the upper flange 32 to the lower flange 34, as shown in FIGS. 1-1, 1-10 and 1-11. The curvature helps create the space which forms the cavity 16 to accommodate the patient's nose. Side portions of the main body 31 may include cuff connecting surfaces 38 which sealingly engage the cuffs 50.

As best shown in FIG. 1-6, the upper flange 32 may be angled to form a central apex to conform to the nasal bridge region of the patient's face. The lower flange 34 may be shaped to conform to the patient's top lip and lower portion of the nose. For example, as best shown on FIG. 1-9, the lower flange 34 may comprise at least two curves or undulations 37 having a central portion 39 forming a lower extent of the undulations 37. The central portion 39 may form a convex curvature adapted to accommodate the patient's septum or philtrum region.

The front panel 30 may be constructed of a textile. The textile may be an air holding or sealed textile that may not permit gases to pass through its fibers. For example, the textile may be a composite material having a first layer of fabric and a second layer of polymer (i.e. a coated textile). The second layer of polymer may be a film, spray coat or other arrangement adapted to seal the first layer. In an alternative form, the front panel 30 may be constructed or formed from a clear or generally clear material including for example polycarbonate, polypropylene, or silicone, so that the patient's nose may be visible to a clinician.

The front panel 30 may include a vent portion. For example, a vent component (such as a grommet or insertable vent component) may be sealingly attached to front panel 30. The vent component may be substantially rigid or semi-rigid in order to maintain the patency of the vent holes and reduce vent noise. Alternatively, the fabric of the front panel 30 may be selectively sealed such that a portion of the fabric is not air tight, thereby acting as a vent.

In use, a seal member (e.g., a flap seal, in this example, made from textile and/or an elastomer) of thin material may have a self sealing action when positive air pressure is applied within the mask, which may stiffen the textile of the front panel 30, thereby creating a larger space to accommodate the patient's nose.

In an example, the front panel has a height of about 45-80 mm (e.g., 50-70 mm, or about 60 mm, or about 65 mm).

In an example, the front panel 30 has a width (for example from one end of the lower flange 34 to the other end of the lower flange) of about 80-120 mm (e.g., 90-110 mm, or about 100 mm, or about 96 mm).

In an example, the front panel 30 has a radius of curvature $\alpha$, as shown in FIG. 1-2, along the vertical axis of about 10-30 mm (e.g., 10-25 mm, or about 15 mm).

In an example, the front panel 30 has a radius of curvature $\beta$, as shown in FIG. 1-7, along the horizontal axis of about 10-30 mm (e.g., 10-25 mm, or about 15 mm).

Preferably, the fabric is visually appealing since the front panel 30 is most visible when the mask is in use. The fabric may be a soft textile without being visually bulky, for example nylon, cotton, linen, dazzle, silk etc. The polymer may be polyurethane, polyester, silicone, nylon etc.

The back panel 20 and the front panel 30 may be integrally formed. The back panel 20 and the front panel 30 may be sealingly engaged by welding, heat pressing, or other methods. Alternatively, the back panel 20 and the front panel 30 may be sealingly engaged by stitching or other suitable methods.

In an example, the upper flange 22 of the back panel 20 and upper flange 32 of the front panel 30 may be aligned. Likewise, the lower flange 24 of the back panel 20 and lower flange 34 of the front panel 30 are also aligned. The upper engaging surfaces 23, 33 of the back panel 20 and the front panel 30, as well as the lower engaging surfaces 25, 35 may be welded using radiofrequency or ultrasonic welding. A radiofrequency weld may create a more robust seal which may be preferable in creating an air tight cavity. Preferably, the weld may be three dimensional so as to ensure the shape of the mask 10 is three dimensional. In a further example, a radiofrequency weld may first be formed and a subsequent ultrasonic cut may be made. The ultrasonic cut may round or otherwise curve the edge of the textile in order to prevent facial marking and thereby increase patient comfort.

In an example, the upper and lower engaging surfaces 23, 25 of the back panel 20 and the upper and lower engaging surfaces 33, 35 of the front panel 30 have a width of about 1-10 mm (e.g., 2-6 mm).

Headgear may be attached or otherwise connected to the mask. Alternatively, headgear may be formed with or as a part of the front panel 30 and/or the back panel 20.

A rigidizer (or stiffening element) may be formed with or attached to the front panel 30 and/or the back panel 20. The rigidizer may provide structural stability and support for the mask 10. For example, the rigidizer may be a semi-rigid or a rigid component, such as a polymer shaft or frame. The rigidizer may be positioned at the nasal bridge region (so as to ensure seal at the nasal bridge region and/or sides of the patient's nose adjacent the nasal bridge region of the patient's face as the curvature of the face in this region is particularly difficult to seal against), the top lip region of the patient's face and/or the corners of the nose, for example. Furthermore, the rigidizer may interconnect the cuffs 50.

The seal member 40, as best shown in FIGS. 1-5 and 1-10, is adapted to sealingly engage with the patient's face. The seal member 40 includes a main body 41 and an opening 46 formed in the main body. The main body 41 includes an connecting portion 41-1 that sealingly engages or is otherwise attached to the engagement portion 21-1 of the back panel 20.

The seal member 40 may be constructed and arranged to be positioned proximal to and in sealing engagement with a patient's airways. The seal member 40 may have a generally triangular or trapezoidal shape. Alternative shapes may be possible, (e.g., elliptical, circular, square, etc.). Preferably, the seal member 40 is shaped to provide a visual cue to the patient as to the orientation of the mask. For example, a triangular shape tends to indicate to the patient that the apex of the seal member 40 is to be positioned near the nasal bridge region.

The opening 46 formed in the main body 41 of the seal member may have a triangular or tri-lobular shape, although other suitable shapes may be used.

The seal member 40 may be constructed of a polymer. Preferably, the polymer may have a low hardness so as to readily adapt and conform to the shape of the patient's face. For example, the polymer may be silicone, thermoplastic elastomer, polyurethane, etc., having a Type A or Shore A hardness of 5-20 and a thickness of about 0.3-2 mm (e.g., a Shore A hardness of 5-10 and a thickness of 0.3-2 mm). The polymer may be a low durometer e.g. Type 00 or Shore 00 hardness of 20-40.

In a further alternative, the seal member 40 may be constructed of a tacky or sticky material to better grip the patient's face and thereby form a more robust seal. Tackiness may be provided through surface finish, application of an adhesive or by virtue of the materials properties (e.g. low durometer silicone, e.g. silicone with a Type 00 or Shore 00 hardness of 5-20 is inherently tacky).

In a further alternative, the seal member 40 may be constructed of a textile. Alternatively, the seal member 40 may be constructed of a combination of materials such as a tacky material and a textile.

As mentioned above, the seal member 40 sealingly engages the back panel 20. The seal member 40 may be thermoformed, overmolded, glued, welded or otherwise connected to the back panel 20. Preferably, the connecting portion 41-1 of the seal member 40 and the engagement portion 21-1 of the back panel 20 overlap to ensure that the seal member 40 and the back panel 20 are sealingly engaged, so as to prevent a leak path. In an example, the overlap may be about 1-10 mm wide (e.g., 2-6 mm).

In an example, the seal member 40 has a height of about 30-60 mm (e.g., 40-60 mm, or about 55 mm, or about 45 mm).

In an example, the seal member 40 has a width of about 50-80 mm (e.g., 60-70 mm, or about 65 mm, or about 53 mm).

In an example, the seal member opening 46 has a height of about 15-35 mm (e.g., 20-30 mm, or about 25 mm, or about 30 mm).

In an example, the seal member opening 46 has a width of about 20-40 mm (e.g., 30-40 mm, or about 35 mm).

The mask system may include one or more cuffs 50 coupled to side portions of the mask 10, as best shown in FIGS. 1-5 and 1-9. The cuff may be a male cuff (i.e. protrude from the mask 10, or may be a female cuff, i.e. be contained within the bounds of the mask 10). In the illustrated example, the cuff 50 is a male cuff. Each cuff 50 includes a main body 51 and a flange 54. A hollow portion 52 is formed through the main body 51 and the flange 54 to permit the passage of breathable gas supplied by an air delivery tube. As shown in FIGS. 1-1 and 1-10, the flange 54 is configured to sealing engage the cuff connecting surfaces 28, 38 of the back panel 20 and the front panel 30, for example by gluing, heat forming or welding (e.g., radiofrequency, ultrasonic)

The cuff 50 may have a generally tubular shape, for example a shape having an elliptical cross section. Alternative shapes and cross sections may be used, such as circular, square, rectangle with rounded corners, ovoid, etc.

The flange 54 may also aid in positioning the air delivery tube. For example, the air delivery tube may slide over the cuff 50 until the air delivery tube reaches the flange 54 which may be arranged to indicate that the air delivery tube is correctly positioned.

The cuff 50 may be constructed of a polymer. Preferably, the polymer may be semi-rigid or rigid so as to ensure air delivered from the air delivery tube to the mask 10 is not restricted. The cuff 50 may be constructed of, for example, nylon, polypropylene, polycarbonate.

In an example, the cuff 50 has an internal width along its longest axis of about 15-25 mm (e.g., about 20 mm).

In an example, the cuff 50 has an internal width along its shortest axis of about 5-15 mm (e.g., about 8.5 mm).

In an example, the cuff 50 has a thickness of about 1-3 mm (e.g., about 2.5 mm, or about 1.5 mm).

A single air delivery tube may be connected to one cuff 50, while the other cuff 50 is sealed with a plug (not shown).

Alternatively, two air delivery tubes may be connected, respectively, to the two cuffs 50.

Headgear may be attached to the cuffs 50. The headgear may be formed as conduits to deliver breathable gas to the cuffs 50.

A vent may be provided in one or both of the cuffs or connecting portions 50. The vent may comprise a series of holes adapted to flush exhausted gases (e.g., $CO_2$) from the mask 10. Preferably, the cuff is substantially rigid or semi rigid in order to maintain patency of the vent holes and reduces vent noise.

The cuff may preferably be configured as a female cuff to reduce the size of the mask 10, enable easier connection with a tube and permit the tube or connector (the connector adapted to connect to the female cuff) to have a release button so that attachment and detachment is performed by the tube or connector rather than the cuff.

The cuff(s) could be incorporated into the headgear (e.g. form a part of a headgear rigidiser). The cuff(s) may also provide a connection point with a headgear or headgear connector.

2.0 Sealing Arrangement

In an example shown in FIGS. 2-1 and 2-2, a seal member 40-1 is coupled to a back panel 20-1 and both the seal member 40-1 and the back panel 20-1 include an opening to receive the patient's nose. The front panel is removed in these views for illustration purposes.

The back panel 20-1 may form a soft contact surface to interface with the patient's skin (e.g., fleece or Coolmax® finish). Thickened padded sections may be formed in the back panel 20-1 around high pressure areas, such as the nasal bridge region and the top of lip region, to enhance comfort. Further, the back panel 20-1 may also include rigid sections to provide support and/or shape to the back panel.

Headgear 60, including a strap 62, may be connected to the back panel 20-1. The headgear may be adjustable through a loop tab or other connecting structure and/or may be auto-adjusting through provision of elasticity in the strap 62.

The seal member 40-1 is configured as a thin elastic member and may be formed, for example, of textile, a polymer (e.g., silicone, polyurethane), or a combination thereof through, e.g., lamination or overmolding. The thin elastic seal member 40-1 is arranged to conform to the shape of the patient's face (e.g., nose). Forces exerted on the back panel 20-1, and in turn on the seal member 40-1, by the headgear 60 further cause the seal member 40-1 to conform to the shape of the patient's nose and/or face. The seal member is also activated by pressure of the breathable gas in the chamber forming portion (or cavity), and preferably the seal member may have a high level of flexibility to enable the seal member to more readily respond to system pressure inside the mask. When positive pressure is applied within the mask, there is a self sealing action of the seal member to engage and conform to the shape of the patient's nose to form a seal therewith.

The length seal member that is unsupported (i.e. does not have an underlying layer of back panel or other material), allows the seal member to move freely and flex more readily to conform to the shape of the patient's face.

In accordance with examples of the disclosed technology, the seal member may be positioned on the mask through attachment to the back panel or may be otherwise formed on the back panel or other suitable surface of the mask (or formed as part of the back panel or other portion of the mask). The seal member may include a number of configurations, and when employed with the back panel, the seal member and the back panel may be individually configured or together combined in a number of ways to form various structures or seal arrangements which interface with the patient's face to seal therewith and ensure that breathable gas is effectively delivered to the patient's airways.

For example, instead of a separate seal member, the seal member may be formed as part of the back panel. Further, support padding may be included in the mask to enhance comfort and/or to improve the quality of the seal around difficult areas to seal such as the crevices on the sides of the nose. Also, various parts of the mask may include rigidizing structures. In the following sections, several of such configurations or arrangements are described. It will be understood that any feature described in relation to one example, may be used or combined with another feature in a different example.

2.1 Separate Seal Member

Figures 1, 2, 3:
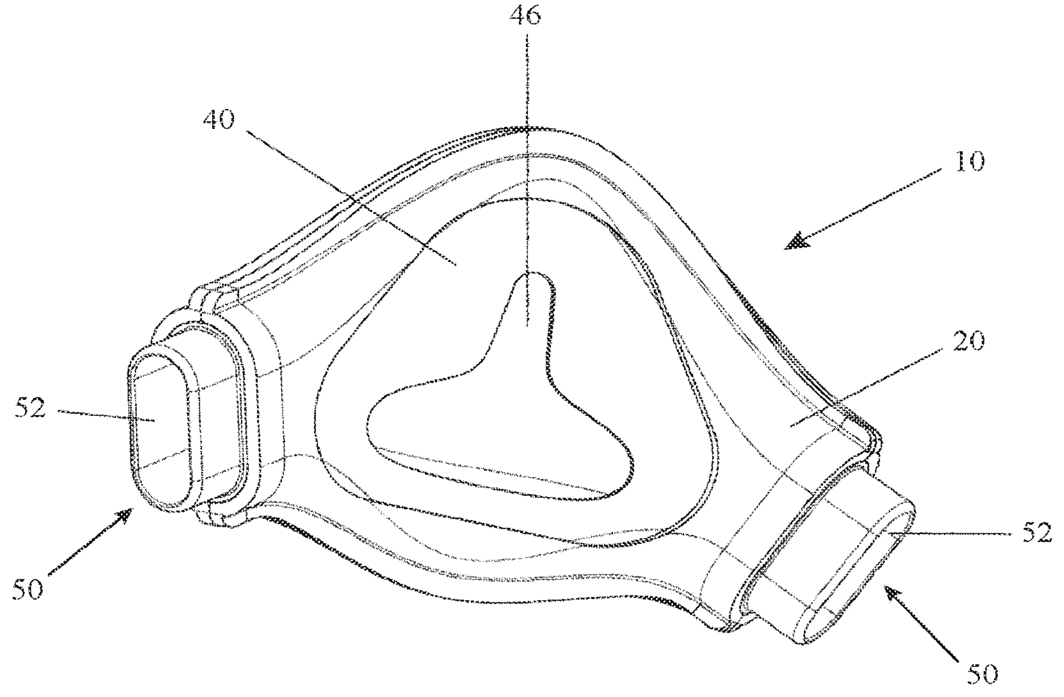
Figures 1, 3:
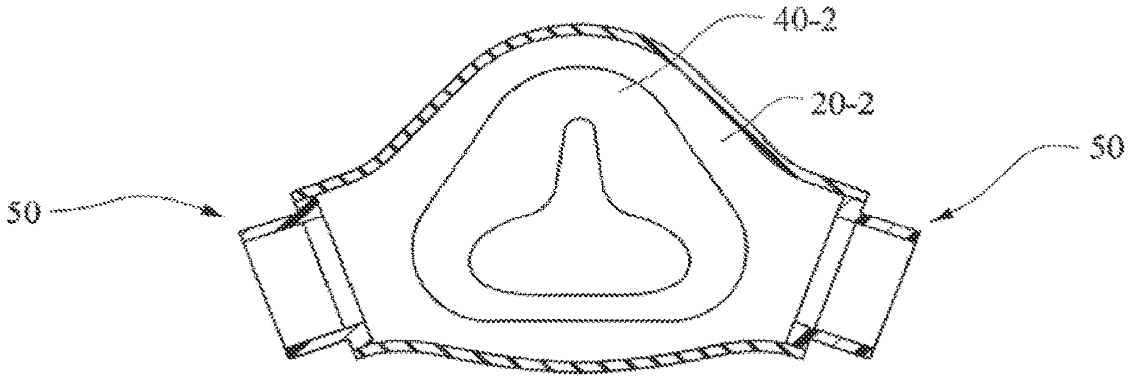
Figures 1A, 3:
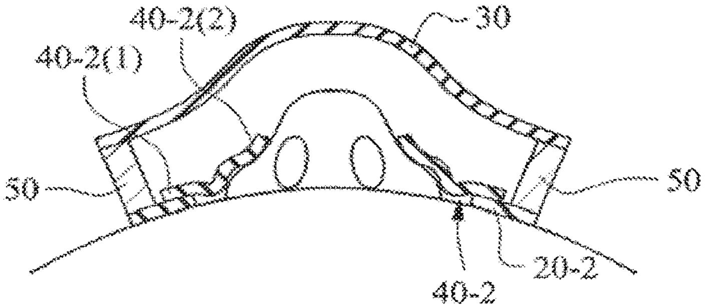
Figures 2, 3:
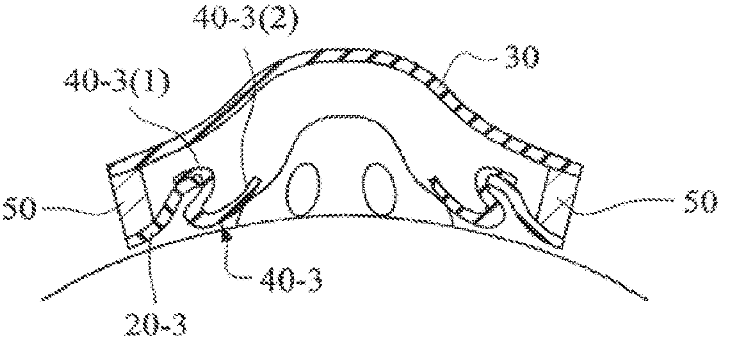
Figures 1, 4:
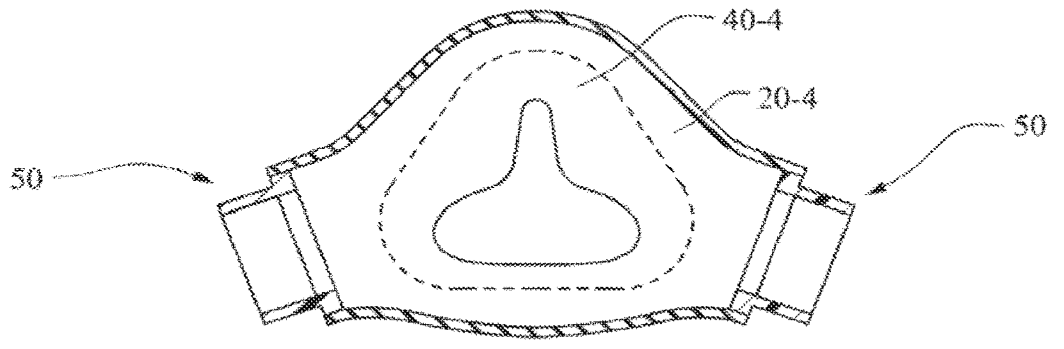
Figures 1A, 4:
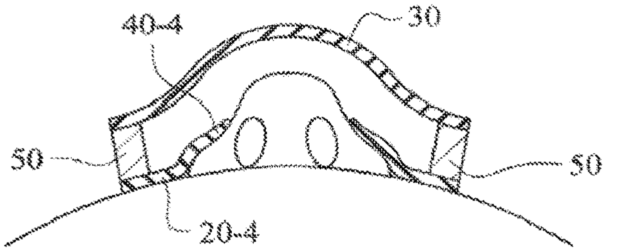

In the example shown in FIG. 3-1, a seal member 40-2 is coupled to a back panel 20-2. The seal member 40-2 may be welded or comolded with the back panel 20-2. As best shown in FIG. 3-1A, the seal member is flexible so as to conform to the patient's face and/or nose. The seal member includes a first end portion 40-2(1) connected to the back panel and a second end portion 40-2(2) to seal against the patient's face and/or nose. The seal member may be formed of silicone or polyurethane, for example, and may further include a single or double wall configuration.

In a further example shown in FIG. 3-2 and in contrast to the seal member 40-2, a seal member 40-3 has an S-like shape in cross-section having a first end portion 40-3(1) connected to the back panel 20-3 and a second end portion 40-3(2) positioned to seal against the patient's face and/or nose. The S-like shape of the seal member 40-3 causes the seal member to function as a spring. Such spring action will tend to cause the seal member to exert a spring force against the patient's face. The spring force may enable the seal member 40-3 to better conform to the curvature of the patient's face and/or nose, which may enhance the quality of the seal and comfort to the patient by allowing the pressure force on the face to be more gradual.

The first end portion 40-3(1) may be thickened to increase support, whereas the second end portion 403-(2) may be thinned down to increase flexibility of the seal member 40-3 which may enable to seal member to better conform to the curvature of the patient's face and/or nose.

2.2 Back Panel with Integral Seal Member

Figures 1, 2, 3, 4:
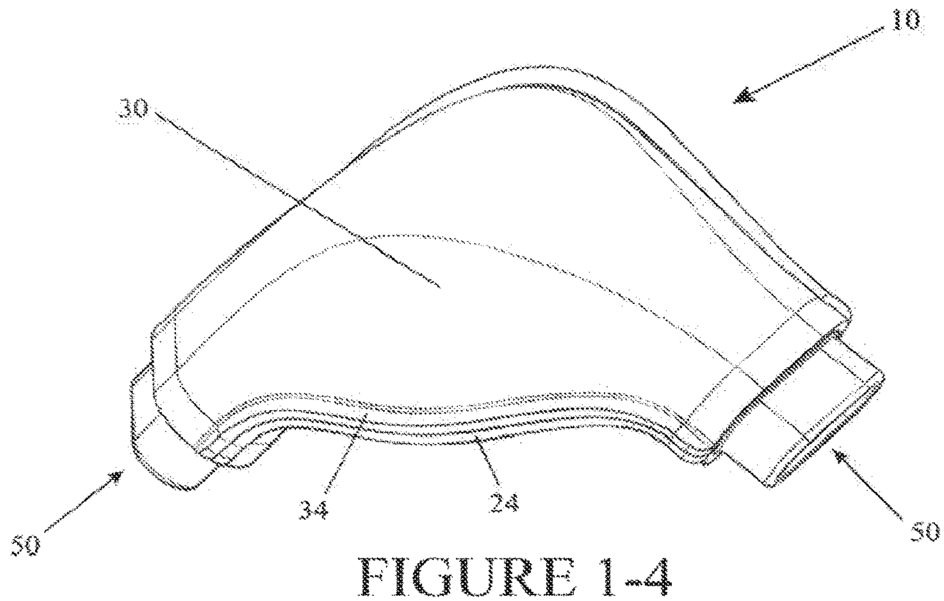

In an example, a seal member 40-4 may be formed as part of a back panel 20-4, as shown in FIG. 4-1. The textile portion forming the seal member 40-4 may be thinner than the back panel 20-4 to increase conformance to the patient's facial features. Such an arrangement may reduce manufacturing complexity, cost, and may make the mask more visually desirable.

2.3 Raised Sealing Arrangement

Referring to FIGS. 5-1 to 5-8B, a cushion may include a raised (i.e. protruding) section which may enhance comfort and improve the seal against the patient's face (especially in hard to seal areas).

Figures 1, 2, 3, 4, 5:
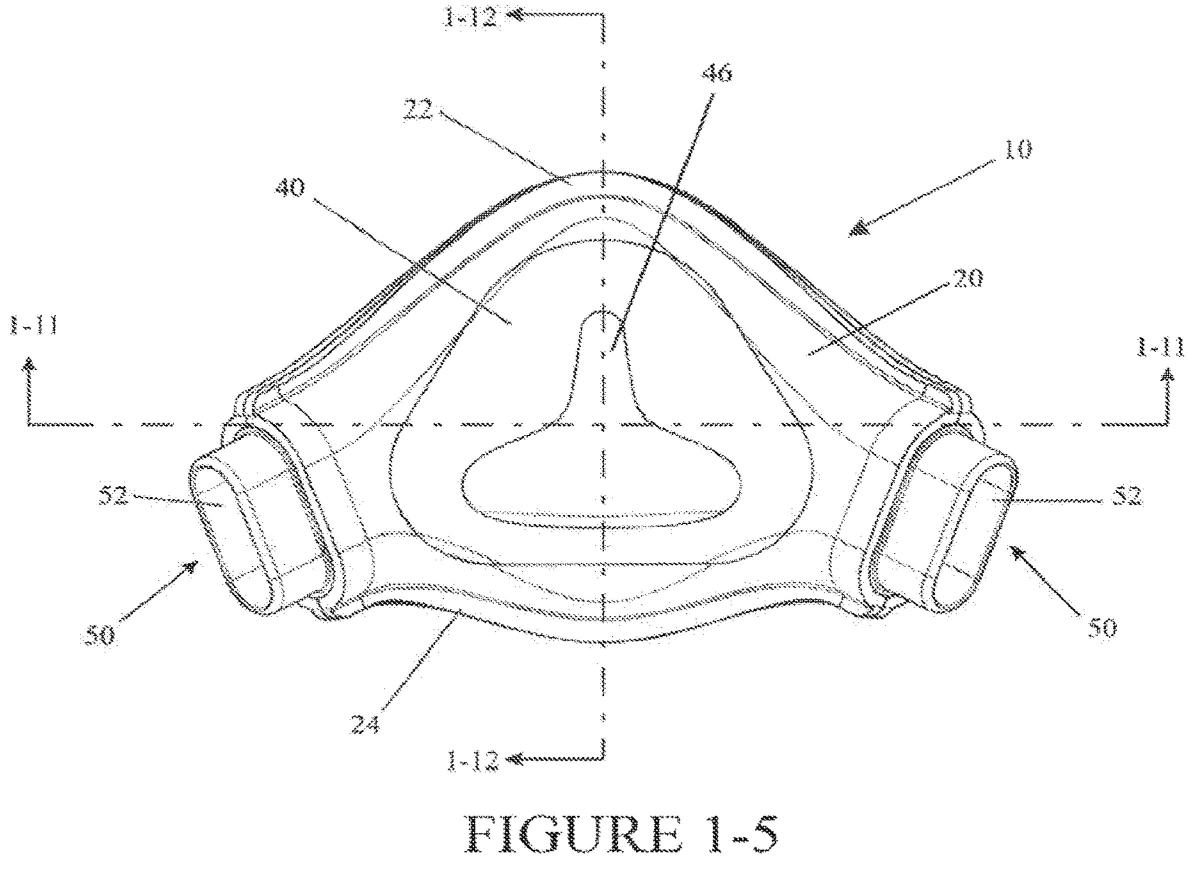

As shown in FIG. 5-1, a mask 10-1 includes a front panel 30, a back panel 20-5 coupled to the front panel, a raised section 90 disposed on the back panel 20-5, and a seal member 40-5 formed or positioned on the raised section 90. As best shown in FIG. 5-2, where the back panel 20-5 is removed from the front panel 30, the raised section 90 includes a cushion portion, padding or padding member 92 which may be formed of foam, for example. The foam may be silicone foam (e.g., a low density, low durometer and/or washable silicone foam). Other foams or cushion-providing material may also be used (e.g., polyurethane foam, open or closed celled foam, skinned or unskinned foam, gel, spacer fabric and/or pile material.

Figures 1, 5:
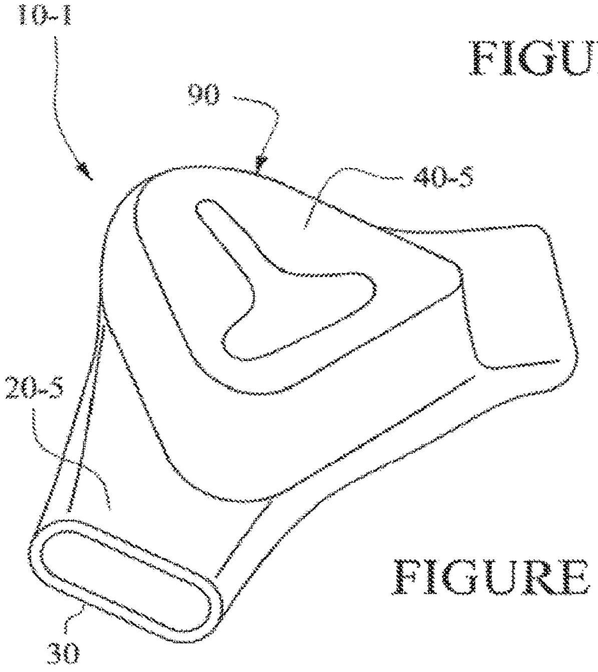
Figures 2, 5:
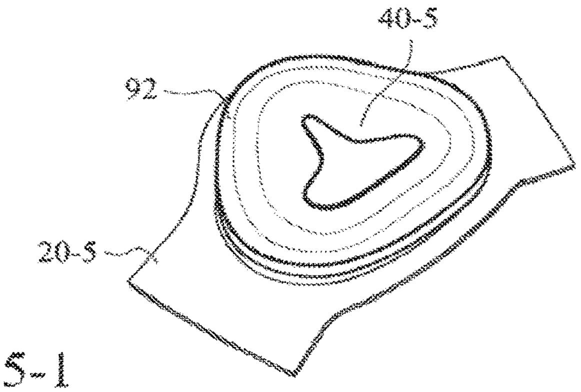
Figures 2A, 5:
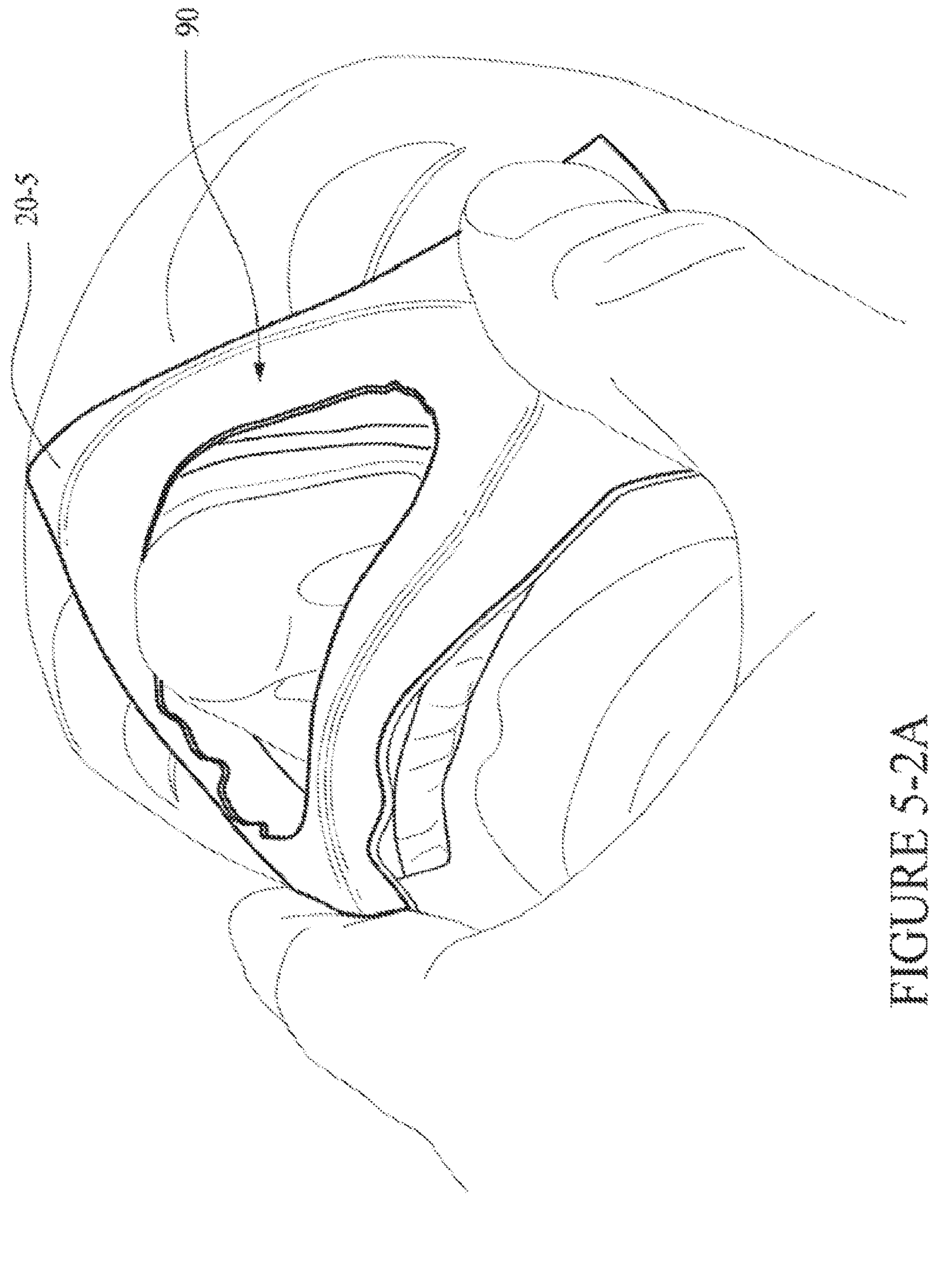
Figures 3, 5:
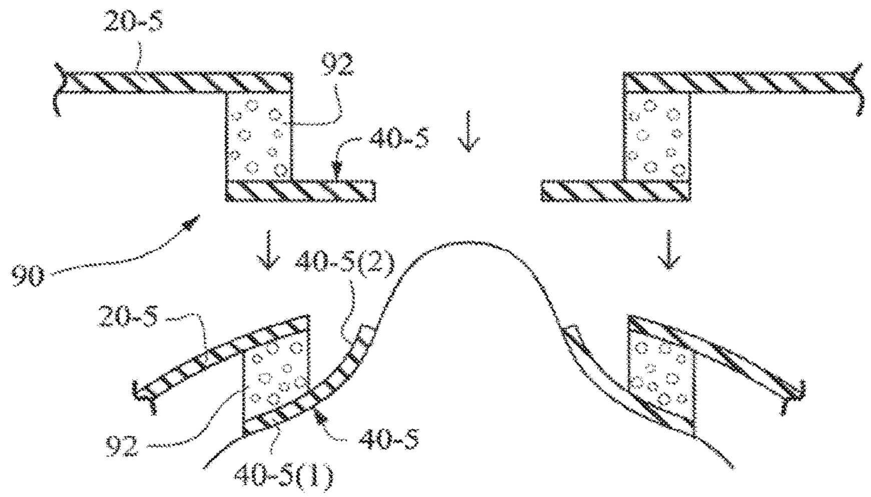
Figures 4, 5:
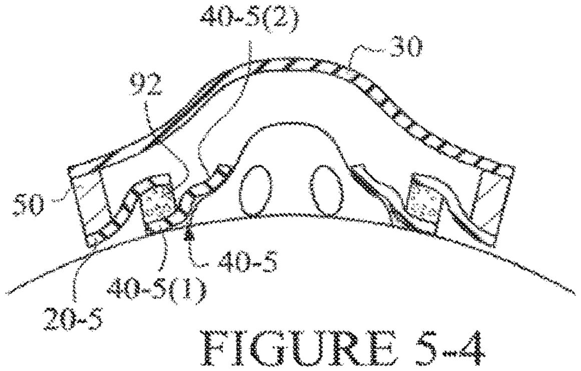
Figure 5:
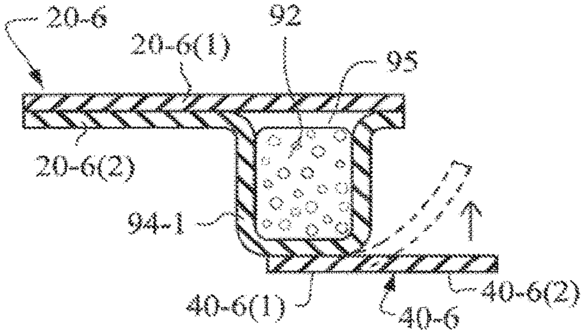
Figures 5, 6:
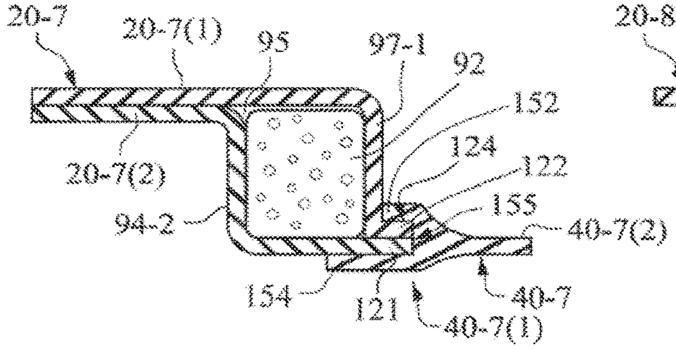
Figures 5, 6, 7:
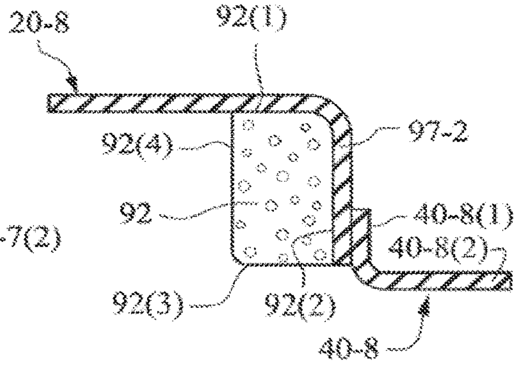

As illustrated in FIGS. 5-2A and 5-3, when the mask 10-1 is worn, the raised section 90 protrudes towards the patient's face and through compression of the padding 92 extends into hard-to-seal areas such as the crevices on the sides of the nose. In other words, the seal member 40-5 is better able to conform to curvatures on the patient's face as the padding provides a light evenly distributed force on the seal member 40-5. As such, the quality of the seal with the patient's face may be enhanced. Additionally, the padding 92 improves comfort to the patient as it provides a cushioning effect to pressure points (e.g., above the top lip and at the nasal bridge). In a further alternative, the cushion portion or padding 92 may be shaped to match the contours of the patient's face.

The padding 92 may be embodied in the mask 10-1 in various arrangements. In the example shown in FIGS. 5-3 and 5-4, the padding has a first end connected to the back panel 20-5 and a second end connected to a first end portion 40-5(1) of the seal member 40-5. A second end portion 40-5(2) of the seal member 40-5 extends radially inwardly from the padding 92.

In another example, a back panel may form an enclosure (or receiving cavity) to house the padding.

Particularly, as shown in FIG. 5-5, a back panel 20-6 includes an inner layer 20-6(1) and an outer layer 20-6(2). The inner layer 20-6(1) may be a coated textile layer (e.g., textile with polyurethane coating) to provide air tightness. The outer layer 20-6(2) may provide a soft outer surface to interface with the patient's skin. The outer layer 20-6(2) may part from the inner layer 20-6(1) to form a receiving portion 94-1 (e.g., a concave or U-shaped formation). The receiving portion 94-1 and the inner layer 20-6(1) together form a receiving cavity 95 which receives the padding 92. Further, a seal member 40-6 may have a first end portion 40-6(1) connected to the receiving portion 94-1 and a second end portion 40-6(2) extending radially inwardly from the receiving portion 94-1. The seal member 40-6 may be connected to the receiving portion 94-1 by injection molding, compression molding, gluing, ultrasonic welding or other techniques. The edges of the joins between the inner layer 20-6(1) and an outer layer 20-6(2) may be rounded by ultrasonic welding or another technique so as to maximize patient comfort and overall visual appearance of the mask. The arrangement shown in FIG. 5-5 may be advantageous as the padding is enclosed and therefore may remain cleaner; further, the overall device may appear neater and more visually appealing and may also be simpler to manufacture.

Figures 1, 2, 3, 4, 5, 6:
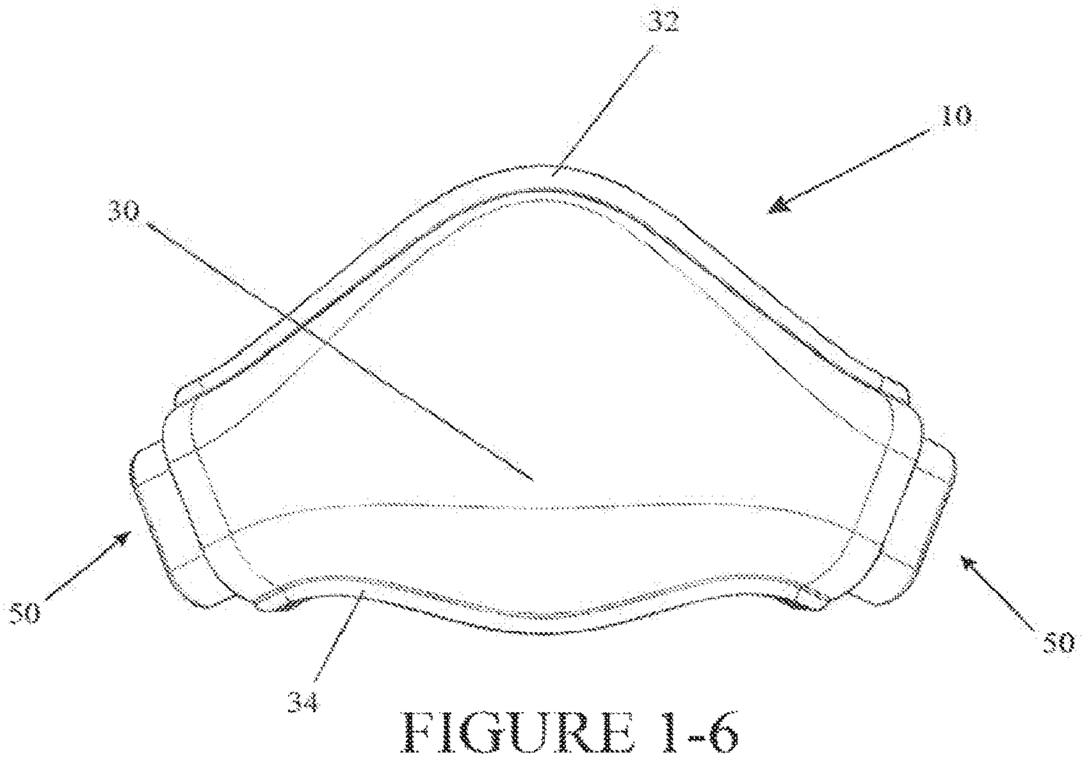

In a further example shown in FIG. 5-6, a back panel 20-7 includes an inner layer 20-7(1) and an outer layer 20-7(2). The inner layer 20-7(1) and the outer layer 20-7(2) may have the same compositions described above with reference to the back panel 20-6. The outer layer 20-7(2) parts from the inner layer 20-7(1) to form a receiving portion 94-2 (e.g., an L-shaped formation). Likewise, the inner layer 20-7(1) parts from the outer layer 20-7(2) to form a receiving portion 97-1 (e.g., an L-shaped formation). The receiving portions 94-2, 97-1 together form the receiving cavity 95 which receives the padding 92.

The outer layer 20-7(2) may extend beyond cavity 95 to form a connecting lip 121. The inner layer 20-7(1) may have a connecting lip 122 that is joined to the connecting lip 121 of the outer layer 20-7(2) to form a mounting structure 124 for a seal member 40-7. The seal member 40-7 includes a first end portion 40-7(1) which is connected to the mounting structure. The first end portion 40-7(1) comprises a first leg 152, a second leg 154 and a receiving space 155 therebetween. The receiving space 155 is configured to receive the mounting structure 124 to secure the seal member 40-7 to the back panel 20-7. The first leg 152 may have a length that enables the first leg 152 to abut against the inner layer 20-7(1) of the back panel 20-7, whereas the second leg 154 may have a length that is larger than the first leg 152 so that the second leg 154 extends along the outer layer 20-7(2) of the back panel 20-7 a sufficient distance to ensure that the seal member 40-7 is stably mounted to the back panel 20-7. This arrangement may be preferable since the foam is enclosed and thereby shielded or protected from dirt and other undesirable materials. The seal member 40-7 may be more securely attached to the back panel 20-7 since a greater surface area is in contact with the back panel, in addition to having multiple planes of contact with the back panel 20-7 and the edges of the joins between the inner layer 20-6(1) and an outer layer 20-6(2) (e.g., the mounting structure 124) may be utilized to attach the seal member 40-7 and thus support a portion of seal member 40-7.

In another example, the seal member 40-7 may be configured and connected to the back panel 20-7 in the same manner described above with reference to the seal member 40-6 and the back panel 20-6.

Figures 1, 2, 3, 4, 5, 6, 7:
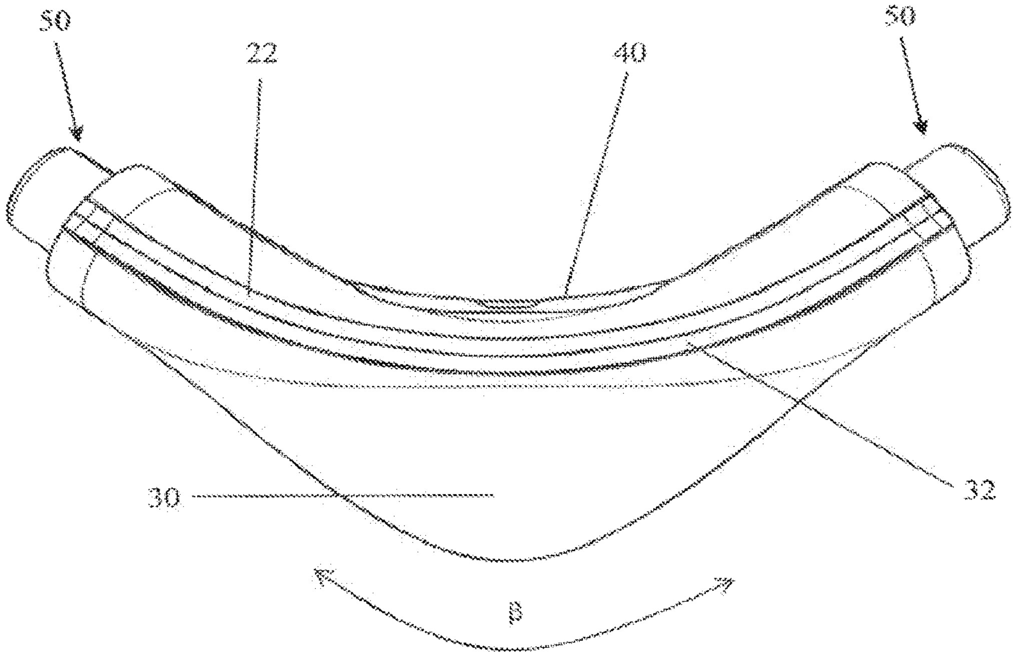

In another example, the padding 92 is molded, glued or otherwise connected to a back panel 20-8, as shown in FIG. 5-7. The back panel 20-8 forms a receiving portion 97-2 (e.g., an L-shaped formation). The padding 92 (e.g., silicone foam) is molded to the receiving portion 97-2 such that an upper surface 92(1) and a first side surface 92(2) of the padding 92 engage the back panel 20-8 and a lower surface 92(3) and a second side surface 92(4) are exposed from the back panel 20-8. This arrangement may be advantageous as fewer materials are required (i.e. no front panel) and the foam may contact the patient's face which may be comfortable for the patient to wear. Since the foam is exposed, it may act as an end of life indicator (i.e. once the foam gets dirty it will serve as an indicator to the patient to get a new mask).

Referring to FIGS. 5-8A and 5-8B, the sealing arrangement may be configured to accommodate anthropometric variance in nose depth. For instance, the sealing arrangement may be configured to comfortably fit both patients with nose bridges having a shallower depth as well as nose bridges having a larger depth. A patient having a shallower nose bridge depth d1 is represented in FIG. 5-8A and a patient having a larger nose bridge depth d2 is represented in FIG. 5-8B. In other words, d1 is smaller than d2.

Padding 92 may be connected to a back panel 20-9. The padding 92 in the upper lip region may be thicker than the padding in the nasal bridge region, as shown in FIGS. 5-8C and 5-8D. That is, the nose bridge region may have little to no padding and a longer membrane as compared to the upper lip region. This is because the seal at the nose bridge region is preferably a membrane or flap type seal, as this type of seal can more readily accommodate varying anthropometrics. In addition, the membrane type seal may extend towards and connect directly or adjacent to the front panel in order to maximize the space for the user's nose bridge. Preferably, at the sides of nose and upper lip region there is more foam and less membrane so as to allow a compression type seal (so that the foam can compress into the crevices and creases particularly in the corners of the nose to facilitate sealing in these areas). The foam may also be more comfortable in these regions. In another example, the foam may have the same depth around the perimeter of the seal portion to form a compression type seal all of the way around the patient's nose.

In the illustrated example of FIGS. 5-8A to 5-8D, A seal member 40-9 is further connected to the padding 92. The seal member 40-9 may have a U-shaped configuration at least in the nasal bridge region of the patient's face. A first end portion 40-9(1) of the seal member 40-9 is connected to the padding 92 and a second end portion 40-9(2) of the seal member 40-9 is arranged to engage the patient's face. The first and second end portions 40-9(1), 40-9(2) generally form the legs of the U-shaped seal member 40-9. Such configuration may enable the seal member 40-9 to extend to reach the face of a patient having a shallower nose depth. Additionally, the U-shaped configuration allows the seal member 40-9 to collapse and conform to the patient's face (i.e. the first and second end portions 40-9(1) and 40-9(2) are moved closer to one another) when positioned on a patient having a larger nose bridge depth. The seal member may have a preformed curvature such that the collapse is controlled.

The padding 92 functions to evenly distribute pressure against the seal member 40-9, thereby improving comfort to the patient. The U-shaped seal member 40-9 may be limited to regions of the seal member proximate the nose bridge region as this region tends to vary significantly from patient to patient. The seal member 40-9 may be substantially flat in other regions of the seal member that would be generally positioned at or near the patient's upper lip (FIGS. 5-8C and 5-8D), as this region tends to have less anthropometric variation.

2.4 Rigidizing Structures

In accordance with the disclosed technology, rigidizing structures may be incorporated into a mask to provide, for example, support, shape, form and/or strength to the mask, as well as to prevent distortion of the mask. In addition, a rigid element may interconnect two or more other rigid components to ease manufacturing and stabilize and position the rigid components relative to one another. The rigidizer may form a support band. The rigidizer may be flat and able to bend to a curvature or may be preformed in a curved manner. The rigidizer may be constructed and arranged to support a portion of the mask, as the mask itself may not be able to support its own weight or may not be able to support an application of force (e.g. tube drag force).

Referring to FIG. 6-1, a mask includes a rigidizer frame 70 layered on top of the back panel 20-2. The rigidizer frame 70 includes side portions 70(2) which extend along the sides of the mask adjacent the cuffs. In an example, the side portions 70(2) may be connected to the cuffs 50. An interconnecting portion 70(1) extends across the upper lip region of the patient and bridges or interconnects the side portions 70(2). The interconnecting portion 70(1) may cause the back panel 20-2 and/or the seal member 40-2 to more stably engage the patient's face in the upper lip region. This may enhance the seal with the patient's face. Further, by extending to both sides of the mask, the rigidizer frame 70 resists distortion of the mask which may result from over-pulling of the straps.

Referring to FIGS. 7-1 to 7-3, a rigidizer frame 72 is shown positioned on the back panel 20-2. The rigidizer frame 72 includes cheek portions 72(2) configured to rest adjacent the patient's cheeks, side of nose portions 72(3) extending from the cheek portions 72(2) partially across the patient's nose in the direction of the nasal bridge, and an interconnecting portion 72(1) extending across the upper lip region of the patient bridging or interconnecting the cheek portions 72(2). The interconnecting portion 72(1) functions similarly to the interconnecting portion 70(1) described above.

A gap may tend to form between the back panel 20-2 (and/or the seal member 40-2) and the patient's face in the portions extending between the patient's nasal bridge and cheeks. The side of nose portions 72(3) shown on the left and right sides of the mask, provide support and shape to the back panel 20-2 and seal member 40-2 in this region. The side of nose portions 72(3) may have a curvature 72(3)*a* similar to that of the patient's face (from the patient's cheeks to nasal bridge) which may force the back panel 20-2 and/or seal member 40-2 to conform to the curvature of the patient's face to reduce or prevent leakage. Slots 72(4) may be formed as part of the rigidizer frame 72 and may receive headgear straps or may be configured to connector to cuffs for example.

Figures 1, 2, 3, 4, 5, 6, 7, 8:
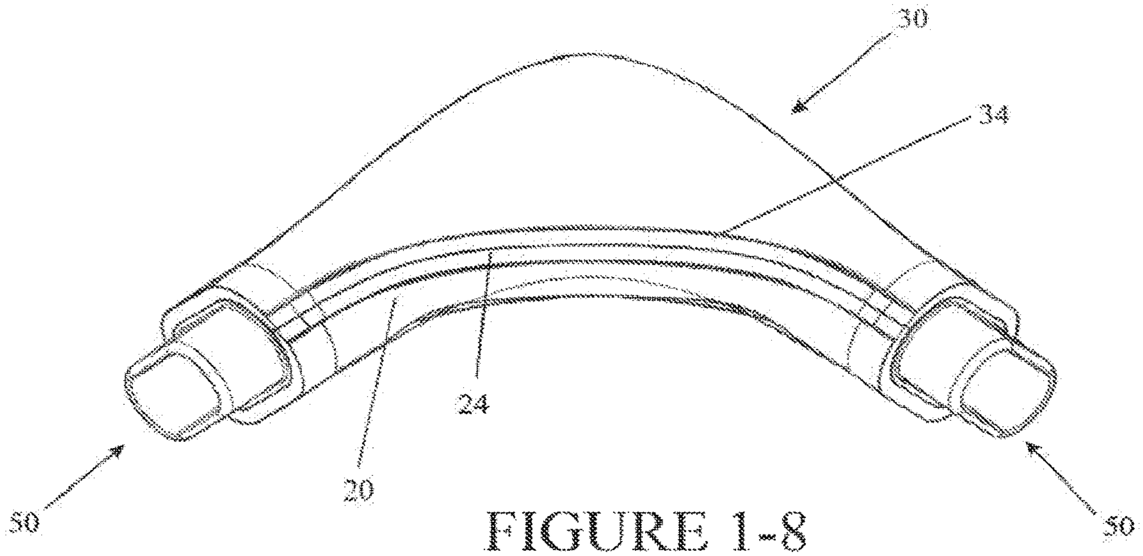

Turning to FIG. 8-1, in an example, a rigidizer frame 74 may extend from a cuff 50-1. The rigidizer from 74 may be a separate member connected to the cuff 50-1 or may be integrally formed with the cuff. In another example shown in FIG. 8-2, a rigidizer frame 76 may extend from a cuff 50-2 and additionally include an interconnecting portion 76(1) layered against the front panel 30 and bridging or interconnecting the cuffs 50-2 to provide shape, form and resist distortion which may result from over-pulling of the straps.

In another example, the first end portion 40-3(1) of the seal member 40-3 in FIG. 3-2 may be thickened to act as a rigidizer frame.

The rigidizer frames described above may be overmolded, glued or welded for example to the mask panels prior to assembly. They may also form separate removable components that are inserted into the mask after the mask is assembled.

The rigidizer frames may be rigid or semi-rigid. For example, the rigidizer frames may be made of flexible semi-rigid plastics such as polypropylene, nylon, polycarbonate, etc. Further, the masks may be rigidized through lamination of high-density foams with the textile panels (e.g., front and back panels). These laminated structures can also be thermoformed to add shape and strength (e.g., by varying he thickness of the laminated structure and/or by adding specific design features such as ribbing).

Rigidizing or strengthening of the mask can also be achieved through use of non-elastic textiles (e.g., in the front and back panels). The non-elastic textiles may form the mask or may be strategically added to the mask to achieve a desired rigidizing or strengthening effect. Such non-elastic textiles may prevent over-stretching in certain directions (e.g., across the upper lip region) which may cause distortion of the mask, or more particularly, the front panel, the back panel and/or the seal member.

In an example, the rigidizer frames may be used limitedly so as to preserve the lightweight, soft and comfortable feel of the textile mask. Further, the use of rigidizer frames over sensitive areas such as the nasal bridge and upper lip areas may be avoided to improve patient comfort by reducing pressure loading in these areas.

In a further alternative, the rigidizer frames may be positioned to overlay the nose bridge, upper lip or other sensitive regions; however, they may be constructed and arranged to avoid contact with the patient's sensitive facial regions. That is, the rigidizer frame may be elevated, raised or curved away from the patient's face, thereby avoiding contacting sensitive regions while still functioning to stabilize and/or strengthen the mask and/or support the shape of the mask.

2.5 Mask Configured to Fit Wide Range of Nose Sizes

Figures 1, 2, 3, 4, 5, 6, 7, 8, 9:
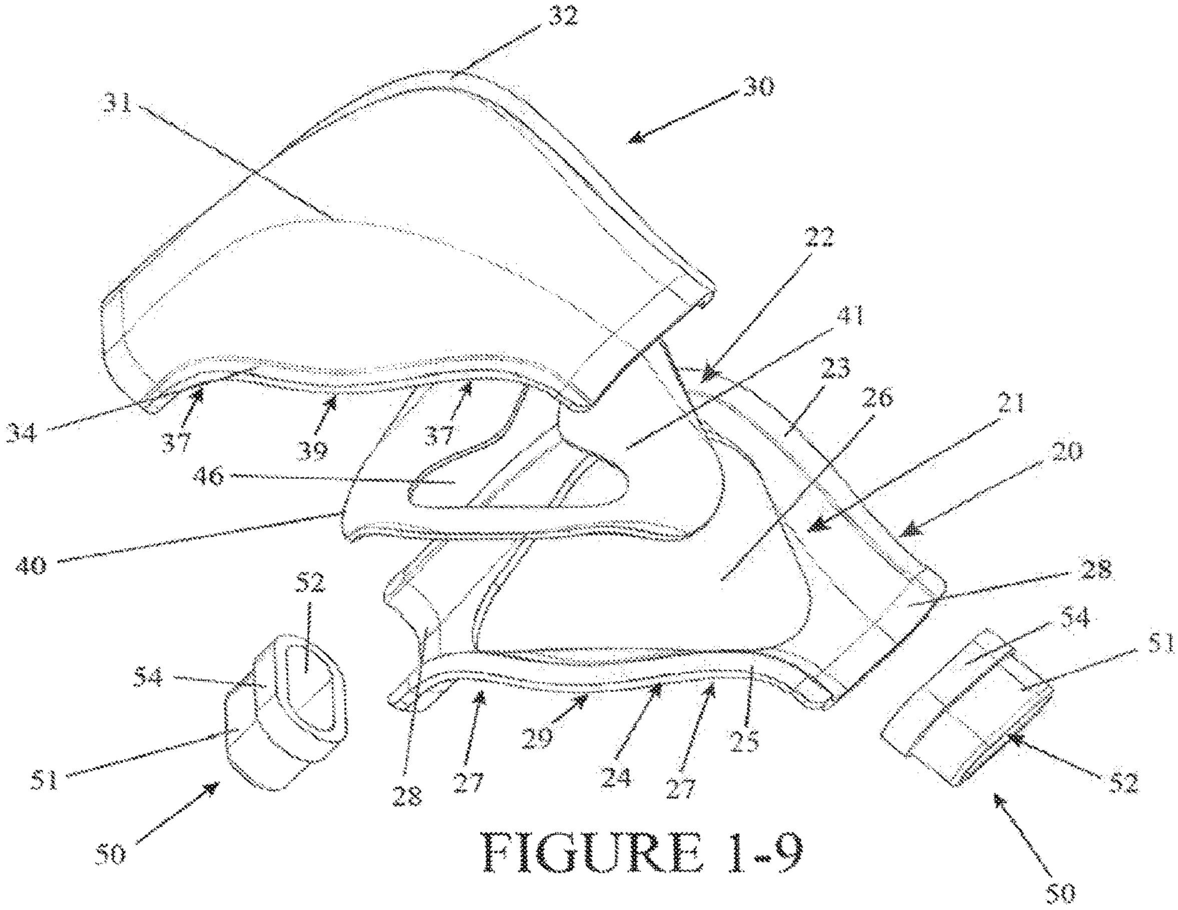

As shown in FIG. 9, the width d5 of the opening in the back panel 20-1 is designed to accommodate a majority of nose sizes so as to fit a majority of the user population with one mask size. The width d5 is wide enough to accommodate the width d4 of a wide nose while the seal member 40-1 extends radially inwardly enough from the back panel 20-1 such that the width d1 of the seal member 40-1 opening in its unstretched state in sufficient to create a good seal against a narrow nose (having a width d2).

Further, the seal membrane is preferably made of a thin high-stretch member (e.g., textile, silicone, or polyurethane membrane) so as to stretch (to a width d3) to receive the width d4 of a wide nose without occlusion.

The back panel 20-1 functions to hold the seal member 40-1 in shape and to assist pulling the seal member 40-1 down onto the patient's face.

2.6 Multi-Layer Seal Member

Figures 1, 2, 3, 4, 5, 6, 7, 8, 9, 10:
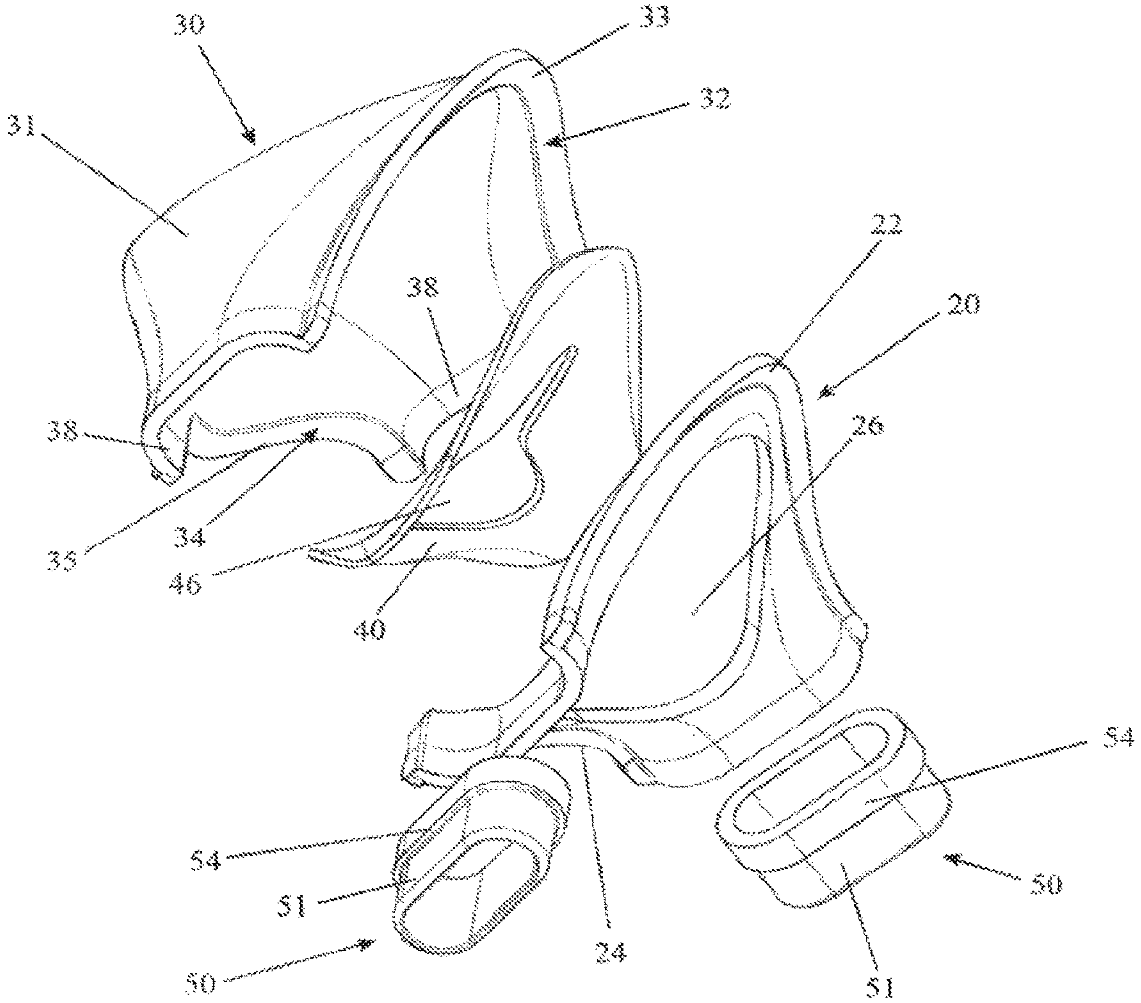

Referring to FIG. 10-1, a mask system 100 may include a mask 110 having a multi-layer seal member 140. The mask system 100 includes headgear 160 and an air delivery tube 180 to supply breathable gas to the mask 110. The headgear includes a strap 162 connected to the mask 110 (e.g., the back panel and/or front panel). The strap 162 may be continuous or may include two straps having an adjustable connection. In either arrangement, the strap 162 has a single vector V1 (The vector for only one side of the mask is shown).

The mask 110 includes a back panel 120 having the seal member 140 connected thereto. The mask may also include a front panel (not shown). The mask forms a cavity to receive the patient's nose to deliver the breathable gas to the patient's airways. The seal member 140 is arranged to seal against the patient's face and/or nose when the patient's nose is received in the cavity. The seal member 140 includes a base layer 141 connected to the back panel 120, an interfacing layer 145 to contact the patient's face, and a cushioning layer or cushion portion 143 disposed between the base layer 141 and the interfacing layer 145, as shown in FIG. 10-2.

Figures 1, 2, 3, 4, 5, 6, 7, 8, 9, 10, 11:
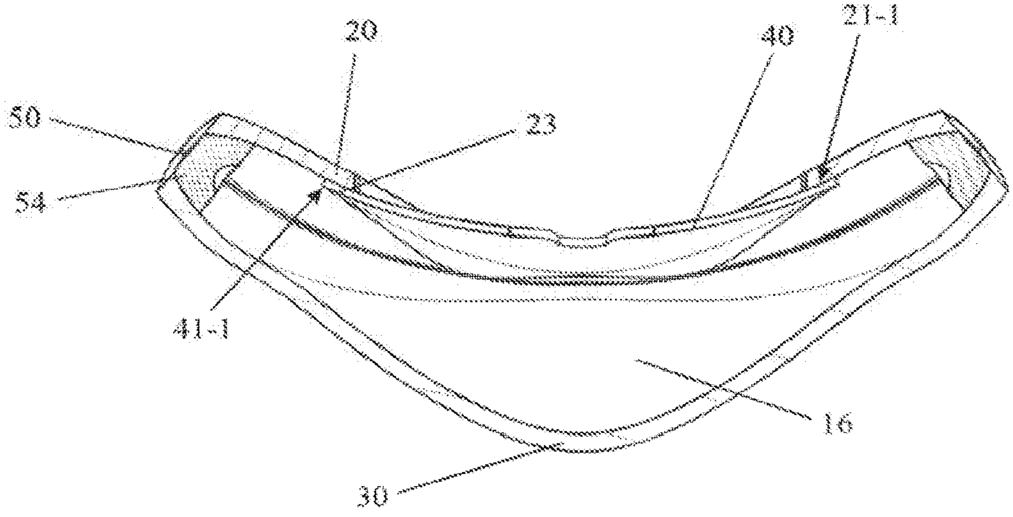

Referring to FIGS. 11-1 and 11-2, the base layer 141 has a generally triangular shape; however, other shapes may be used. An opening 141(1) is formed in the base layer 141 to receive the patient's nose. The opening 141(1) may also have a generally triangular shape, although other shapes may be used. The opening 141(1) is intended to frame the patient's nose.

The width d1 of the opening 141(1) is made smaller than the average/standard anthropometric measurement to require the base layer 141 to be stretched (by tension from the strap 162) in order to receive the patient's nose. The height d2 of the opening 141(1) is sized such that the upper portion of the base layer 141 rests on the lower end of the nasal bridge, as shown in FIG. 11-3, which prevents the mask from obstructing the patient's vision. Width d1 may be about 25-60 mm in length, for example about 30 mm-45 mm, for example about 40 mm Height d2 may be about 15-50 mm in length, for example about 20 mm-40 mm, for example about 30 mm.

Upon receiving a tensile force from the strap 162, the seal member 140 is pulled into sealing engagement with the patient's face. The base layer 141, in particular, functions to cause the seal member 140 to achieve a seal in the upper lip and nasal bridge regions. As shown in FIGS. 11-3 and 11-4, an upper lip sealing area 141*a* spans the upper lip of the patient and extends to the corners of the nose. A nasal bridge sealing area 141*b* is located at a lower end of the nasal bridge.

The base layer 141 may be made from a high stretch, air impermeable material such as thermoplastic polyurethane (TPU) film. The base layer 141 may be also be made from a dense stretchable fabric such as Nylon Lycra. Other suitable materials may also be used. The stretchability and elasticity of the base layer 141 cause the base layer 141 to press against the patient's face when the tensile force is applied. This action pushes the interfacing layer 145 against the patient's face to achieve a seal in the upper lip sealing area 141*a* and the nasal bridge sealing area 141*b*.

The cushioning layer 143 preferably has a perimeter geometry that is identical to that of the base layer 141. The cushioning layer 143 has a raised (or thicker) profile and is intended to provide cushioning to the seal member 140. The opening 143(1) in the cushioning layer 143 has a width d3 and a height d4 that correspond generally to the width d1 and the height d2 of the opening 141(1) in the base layer 141.

Figures 1, 2, 3, 4, 5, 6, 7, 8, 9, 10, 11, 12:
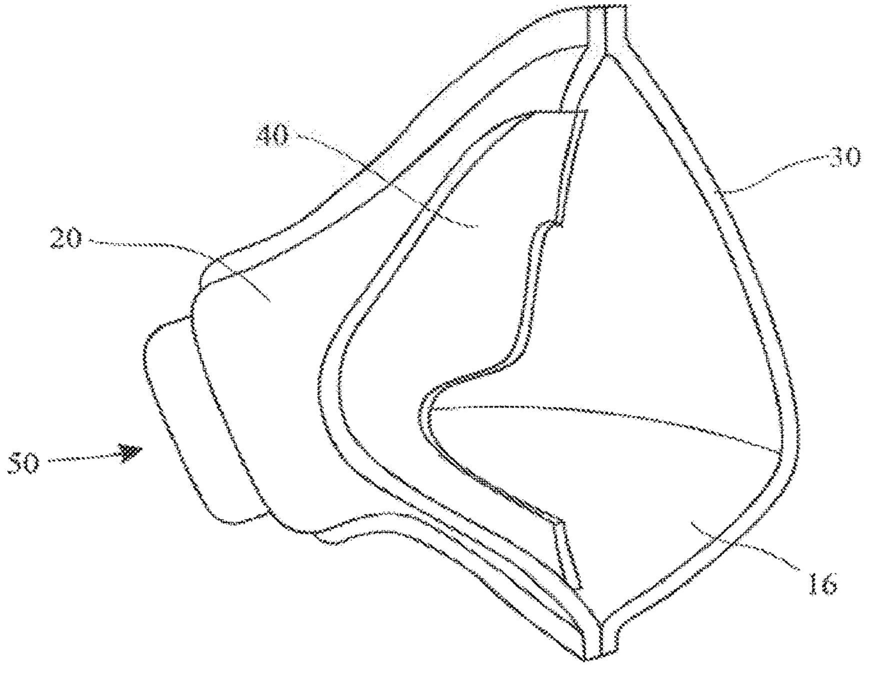

As the seal member 140 is pulled in tension across the nasal bridge, the portion of the seal member spanning the lateral parts of the nose tends to elevate from the patient's face forming gaps 177 (or potential leak path) between the seal member 140 and the patient's face (e.g., the lateral parts of the nose), as illustrated in FIG. 12-3. The cushioning layer 143 functions to provide "mass" against the lateral parts of the nose to fill the gaps 177 while also providing padding over the nasal bridge, as shown in FIG. 12-4.

The cushioning layer 143 may include foam, spacer fabric, plush fabrics, pile fabrics, fibers and/or gel which may be laminated to the interfacing layer 145. The addition of padding to the seal member 140 may assist with sealing against the patient's face (e.g., by filling gaps along lateral parts of the nose). Padding may also improve comfort to the patient, especially in the nasal bridge region, as well as adding aesthetic value to the mask. Preferable material properties of the cushioning layer 143 include the ability to conform to the patient's face as well as having the ability to add bulk/mass to the seal member 140.

Figures 1, 2, 3, 4, 5, 6, 7, 8, 9, 10, 11, 12, 13:
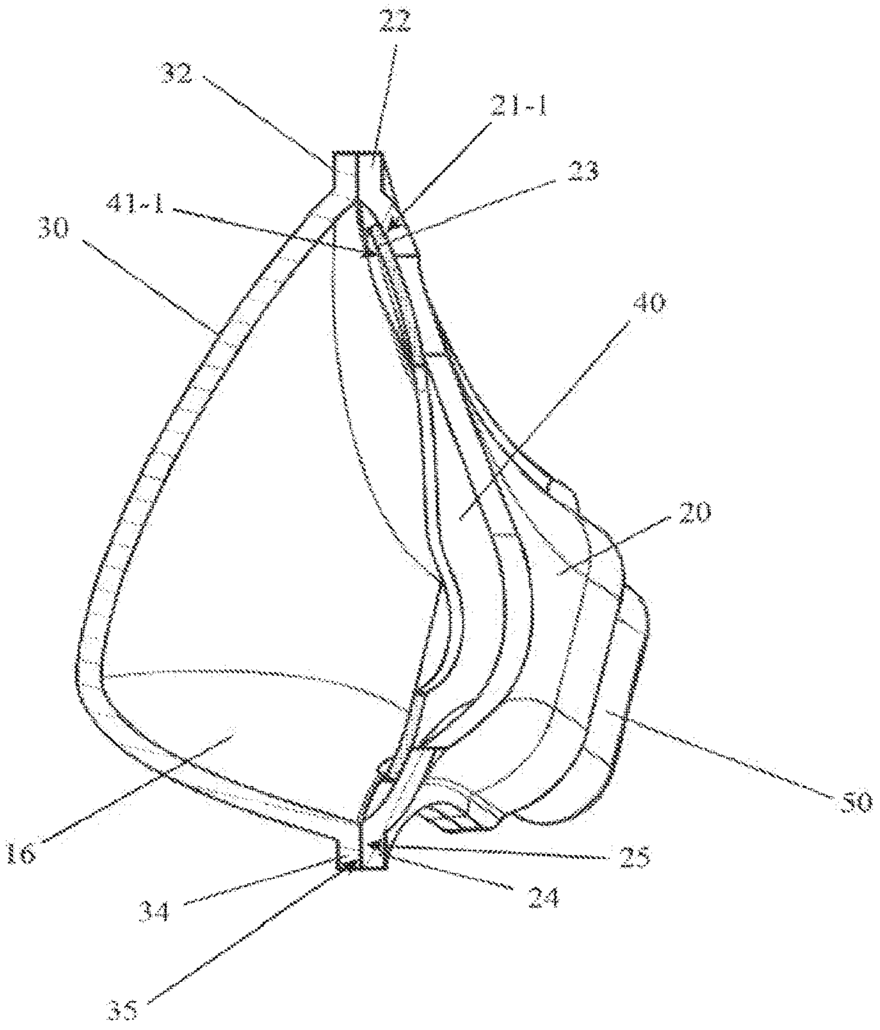
Figures 1, 2:
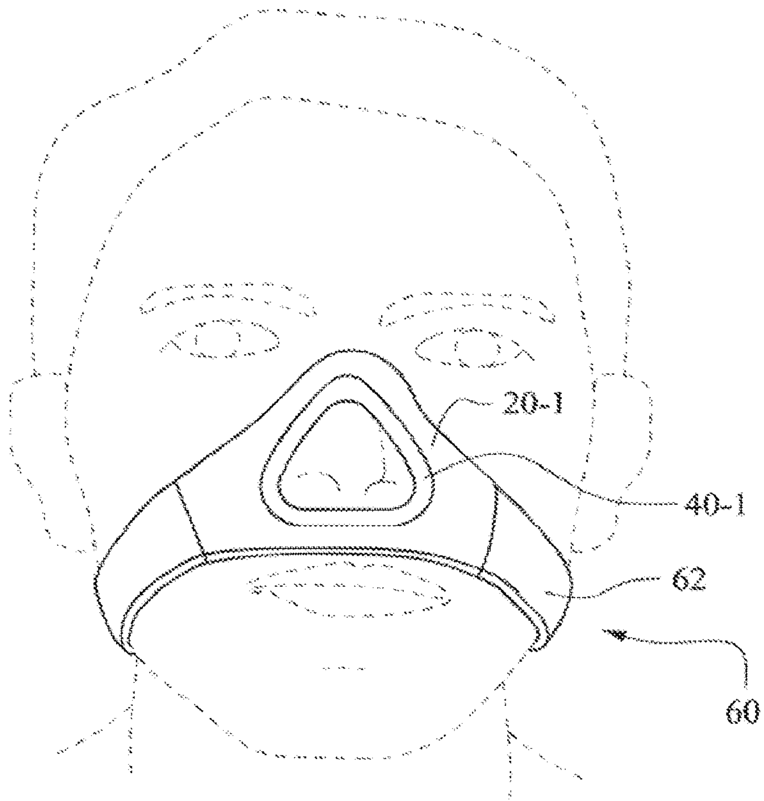
Figure 2:
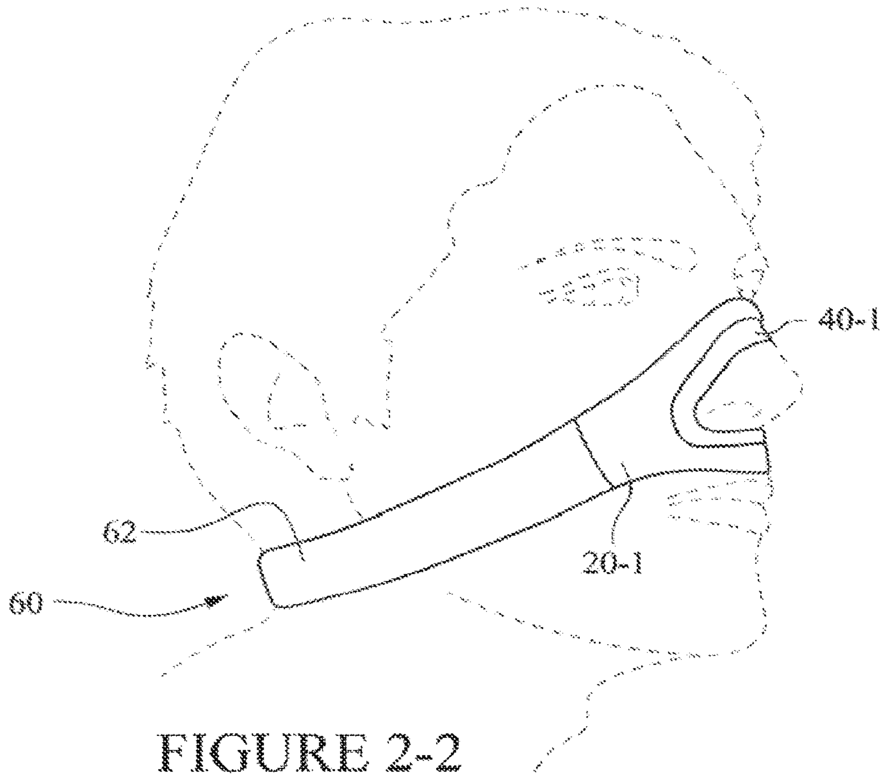

The interfacing layer 145 is arranged to contact the patient's face. The interfacing layer 145 includes an opening 145(1) to receive the patient's nose, as shown in FIGS. 13-1 and 13-2. The opening 145(1) has a generally inverted T shape and includes a central cutout 145(1)*a* having a generally triangular shape, an upper slit 145(1)*b* extending vertically from an upper portion of the central cutout, and lower slits 145(1)*c*, 145(1)*d* extending from left and right lower sides of the central cutout 145(1)*a*. It is noted that the opening 145(1) may have other shapes.

The width d5 of the opening 145(1) may be larger than the width d1 of the opening 141(1) in the base layer 141. This arrangement may assist in pressing the cushion into sealing engagement with the corners of the patient's nose. That is, the base layer may provide support and additional force to press and stretch into the crevices positioned at the sides of the patient's nose. Width d5 may be about 1-5 mm less than width d1. Height d6 of the opening 145(1) may be equal to or less than and the height d2 of the opening 141(1) in the base layer 141.

The opening 145(1) in the interfacing layer 145 forms two flaps 176, 178. As the patient's nose enters the cavity formed in the mask 110, the flaps 176, 178 fold and conform to the lateral parts of the patient's nose to achieve a seal. As shown in FIGS. 13-3 and 13-4, each flap 176, 178 respectively seals against the patient's face in a side of nose sealing area 176*a*, 178*a* along the lateral parts of the nose. The tensile force applied by the strap 162 causes the interfacing layer 145 to be pulled in tension across the upper lip and the nasal bridge to achieve a seal in the upper lip sealing area 141*a* and the nasal bridge sealing area 141*b*.

The interfacing layer 145 may be made from a comforting textile. Preferable material properties for the interfacing layer material include minimal stretchability, air impermeability, conformability to the patient's face, and/or the ability to provide a comforting interface with the patient's face. The minimal stretch of the interfacing layer 145 provides a limiting wall that anchors the seal around the nostrils.

The interfacing layer 145 preferably includes silicone which may aid the seal member 140 in achieving a robust seal against the patient's face. Silicone provides an appropriate level of friction and compliance that is advantageous in improving the seal over the lateral parts of the nose. Use of silicone may also enhance overall mask stability. Alternative materials include thermoplastic elastomers (TPE), polyurethane (PU) coated textiles, non-coated textiles.

The base layer 141, cushioning layer 143 and interfacing layer 145 may be joined by radiofrequency welding, ultrasonic welding, stitching, seam tape, glue, heat stake, overmolding or other air tight sealing methods. Alternatively, the join may not be air tight and instead may permit venting through the seam.

Figure 14:
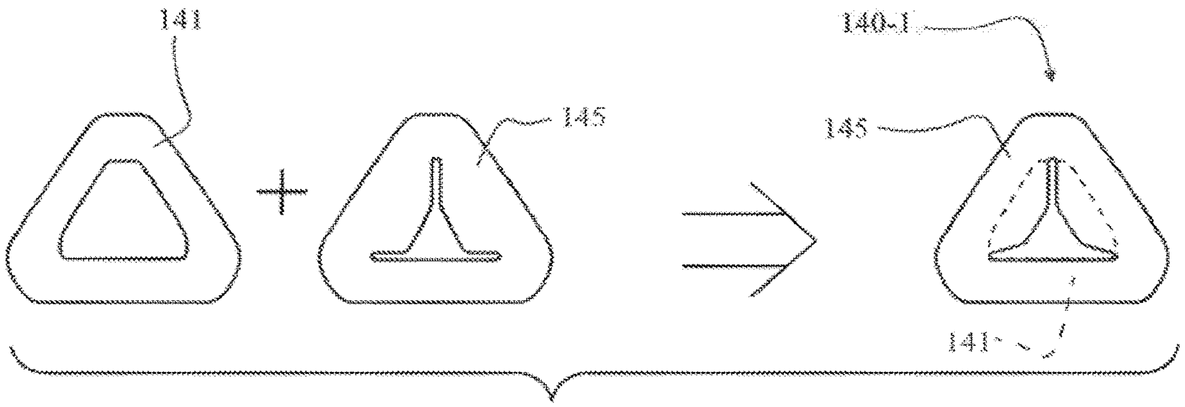
FIG. 14 shows the layers of a seal member according to an example of the disclosed technology.

In another example, the base layer 141 and the interfacing layer 145 may be used without the cushioning layer 143 to form a seal member 140-1, as shown in FIG. 14.

The interfacing layer 145 may be joined to the base layer 141 by stitching or thermoforming, for example. The base layer 141 shape frames the patient's nose and provides a limiting wall about which the interfacing layer 145 folds.

2.7 Continuous Surface Seal Member

Figures 1, 15:
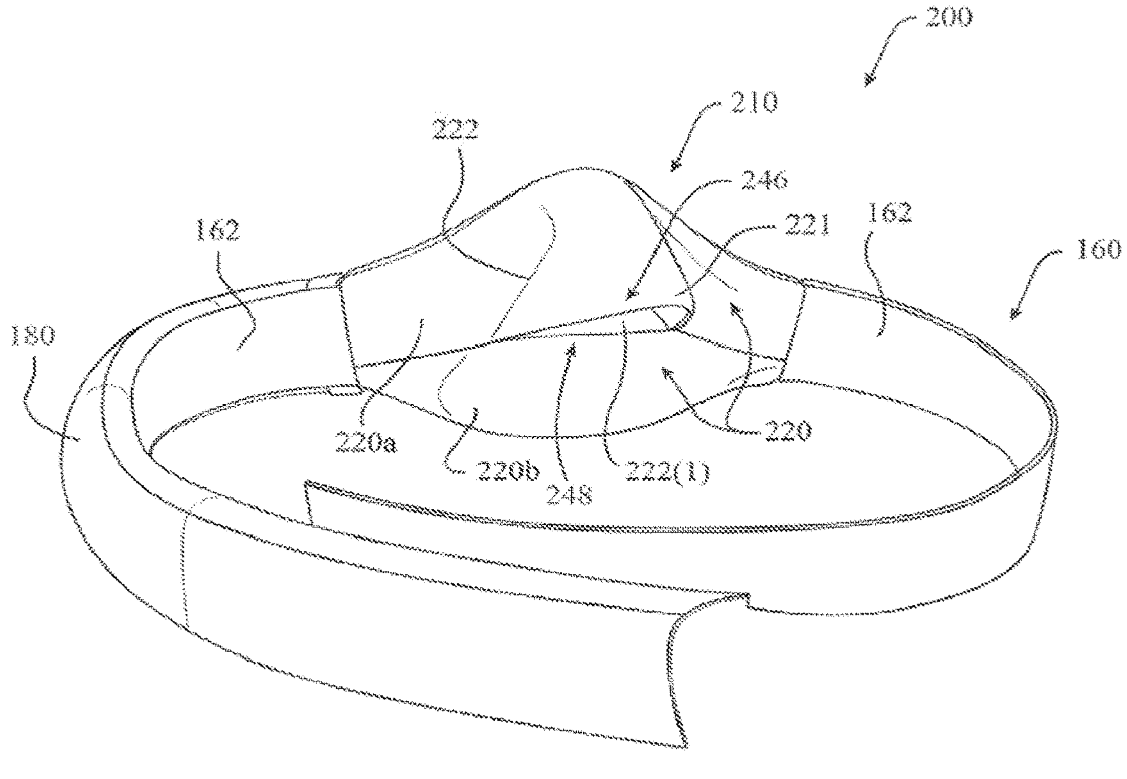
Figures 2, 15:
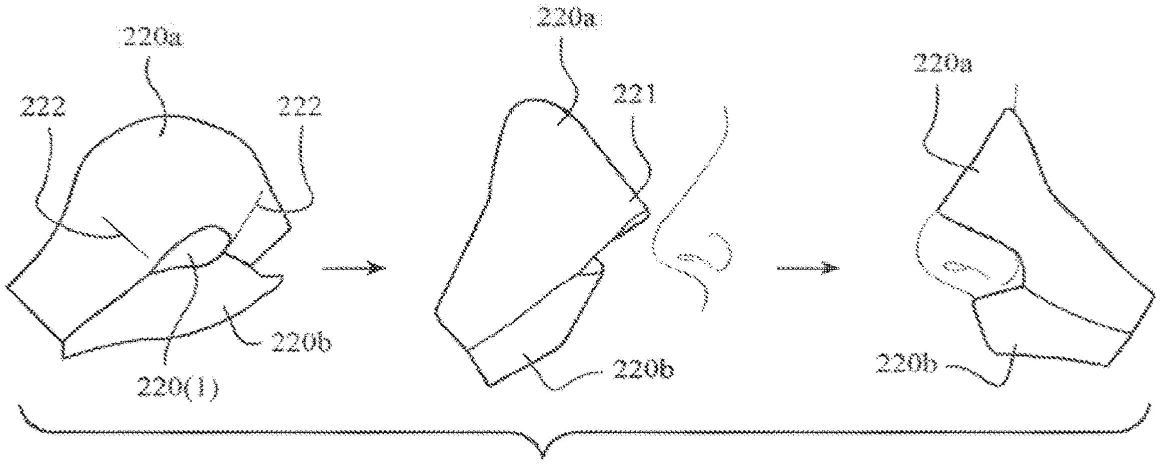
Figures 3, 15:
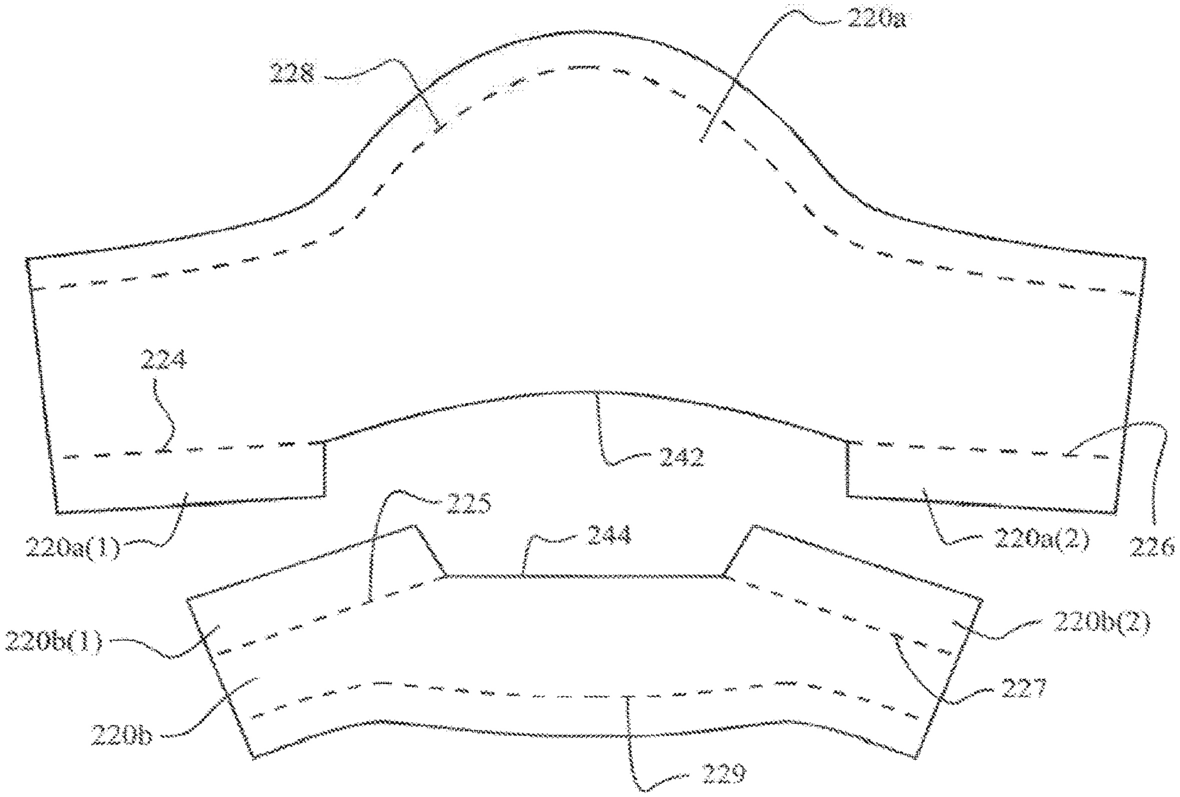
Figures 5, 15:
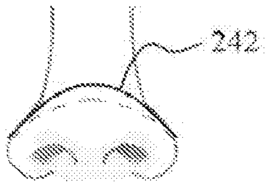
Figures 4, 15:
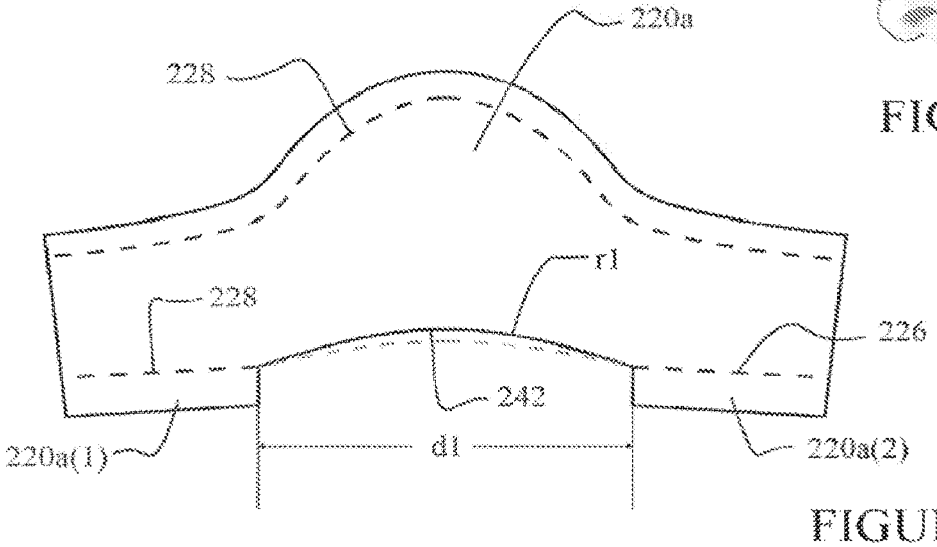
Figures 6, 15:
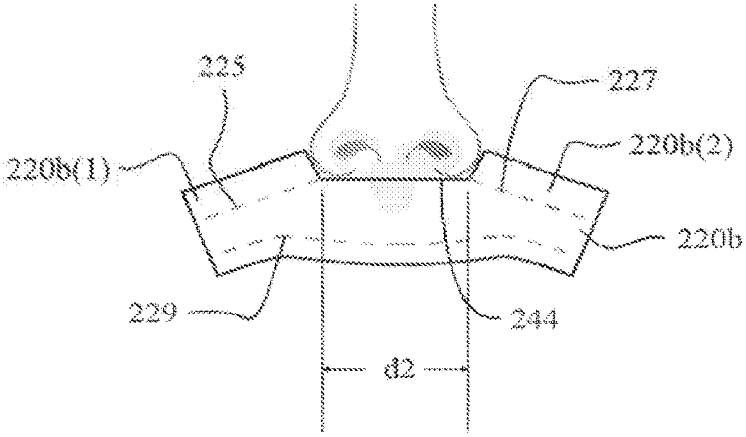
Figures 7, 15:
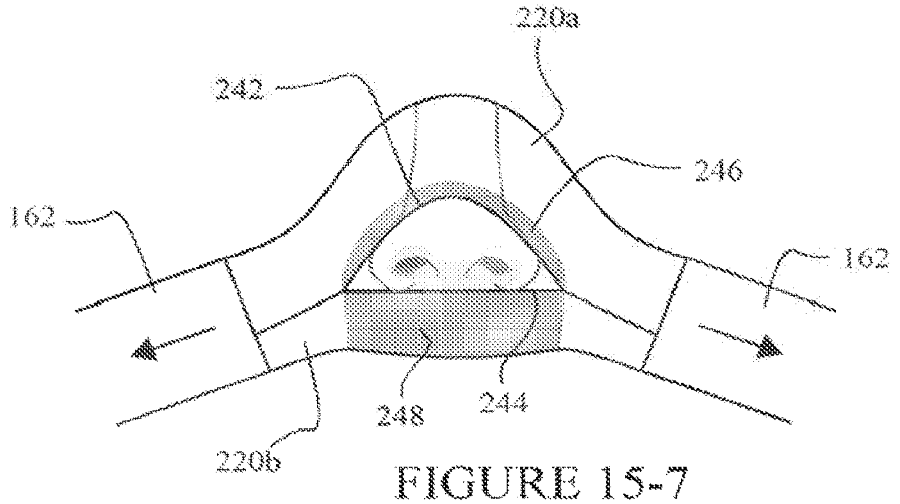

Referring to FIG. 15-1, a mask system 200 includes a mask 210 having a continuous surface that seals over the patient's nose. Particularly, the mask 210 includes a back panel 220 having an upper panel 220*a* and a lower panel 220*b*. An opening 222(1) is formed between the upper panel 220*a* and the lower panel 220*b*. The opening 222(1) receives the patient's nose as it is inserted into the cavity formed in the mask 210. The mask 210 may include a front panel (not shown).

The upper and lower panels 220*a*, 220*b* may be formed from a coated textile (e.g. a PU coated textile, over-molded textile). Preferably, the upper and lower panels 220, 220*b* form a thin air tight fabric.

The upper panel 220*a* has two folds or darts 222 (only one is shown) which cause the upper panel to form a curved portion extending around the opening 222(1) having a peak 221 that protrudes outwardly away from the mask 210, that is, the upper panel 220*a* forms a curved portion adapted to engage the patient's nose. As shown in FIG. 15-2, the mask 210 is positioned on the patient's face by engaging the peak 221 against the patient's nose. As the patient's nose enters the mask, it forces the upper panel 220*a* to extend into the cavity of the mask. Since the upper panel 220*a* is constructed to protrude outwardly as described above, once the patient's nose causes the upper panel 220*a* to turn inside out, the same forces causing the upper panel 220*a* to protrude outwardly now urge the upper panel around the patient's face, thereby enhancing conformance with the patient's facial features.

Referring to FIG. 15-3, the upper panel 220*a* may be connected to the lower panel 220*b* by joining the tabs 220*a*(1), 220*a*(2) of the upper panel with the tabs 220*b*(1), 220*b*(2) of the lower panel and stitching the tabs along the seam lines 224, 225 and 226, 227. The seam line 228 may represent a seam for joining the upper panel 220*a* to another mask part (e.g., a front panel). Likewise, the seam line 229 may represent a seam for joining the lower panel 220*b* to another mask part (e.g., a front panel).

The upper panel 220*a* includes an upper seal portion 246 which seals across the patient's nose, as shown in FIG. 15-7. The upper seal portion 246 extends from a portion of the nose between the nasal bridge and the top of the nose down across the flaring parts of the nose (i.e., external nares) to the corners of the nose. As shown in FIG. 15-6, the lower panel 220*b* includes a lower seal portion 248 which seals across the patient's upper lip. Upon receiving tension from the strap 162, the lower seal portion 248 seals along the upper lip region. The upper seal portion then conforms to the patient's nose as it enters the mask. As the breathable gas is delivered, the upper seal portion 246 and the lower seal portion 248 may be further engaged with the patient's face.

Turning to FIG. 15-4, the upper panel includes a lower boundary 242 extending between the tab 220*a*(1) and the tab 220*a*(2). The width d1 between the tab 220*a*(1) and the tab 220*a*(2) corresponds to the excess portion of the upper panel 220*a* formed around the opening 222(1) shown in FIG. 15-1. This excess portion is used to seal across the patient's nose, as best shown in FIG. 15-7. The width d1 should be undersized (e.g., with respect to average/standard anthropometric measurement) so that the upper panel 220*a* (e.g., the upper seal portion 246) has to be stretched around the patient's nose. Width d1 may be about 50-90 mm, for example about 60-75 mm, for example about 70 mm. This arrangement functions to reduce the likelihood of folds and creases in the upper seal portion which tend to create leak paths. Therefore, the material forming the upper panel may have some flexibility or stretch characteristic.

The lower boundary 242 may have a radius of curvature r1. The radius of curvature r1 determines the location of the lower boundary 242 with respect to the tip of the patient's nose (i.e. nose tip), as shown in FIG. 15-5. In an example, the radius r1 may be about 60-90 mm. For example, radius r1 may be about 65-80 mm. For example, radius r1 may be about 75 mm.

Referring to FIG. 15-6, the lower panel 220*b* includes an upper boundary 244 extending between the tab 220*b*(1) and the tab 220*b*(2). The width d2 between the tab 220*b*(1) and the tab 220*b*(2) corresponds to the width of the opening 222(1). Width d2 may be about 20-50 mm, for example about 30-45 mm, for example about 38 mm. The width d2 may be undersized (e.g., by 0.5-2.5 mm) from the average/standard anthropometric measurement in order to cause the lower panel 220*b* to be stretched to receive the patient's nose. Upper boundary 244 is adapted to form a lower perimeter surface of the sealing portion and is shaped to conform to the patient's septum and/or philtrum.

The seams 225, 227 provide foundation, stiffness and/or shape to the upper seal portion 246. The seams 225, 227 may also be angled to affect the angle and/or orientation of the portion of the upper panel 220*a* extending around the opening 222(1).

3.0 Mask Assembly

Figures 1, 16:
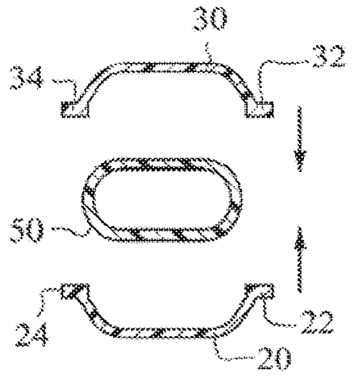
Figures 2, 16:
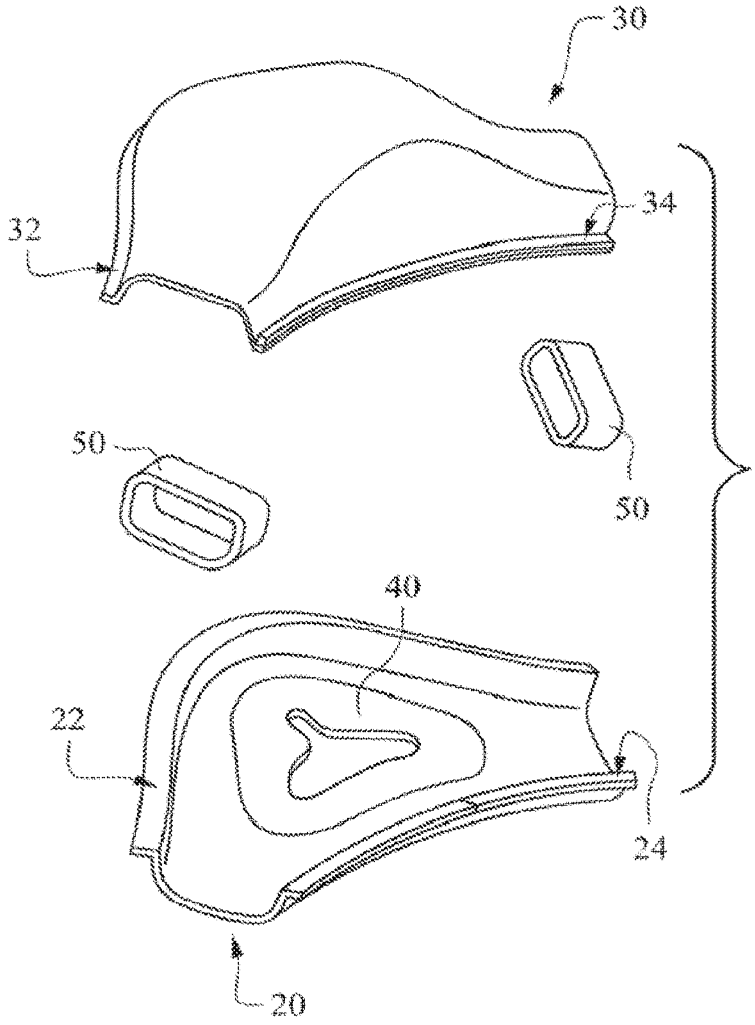
Figures 3, 16:
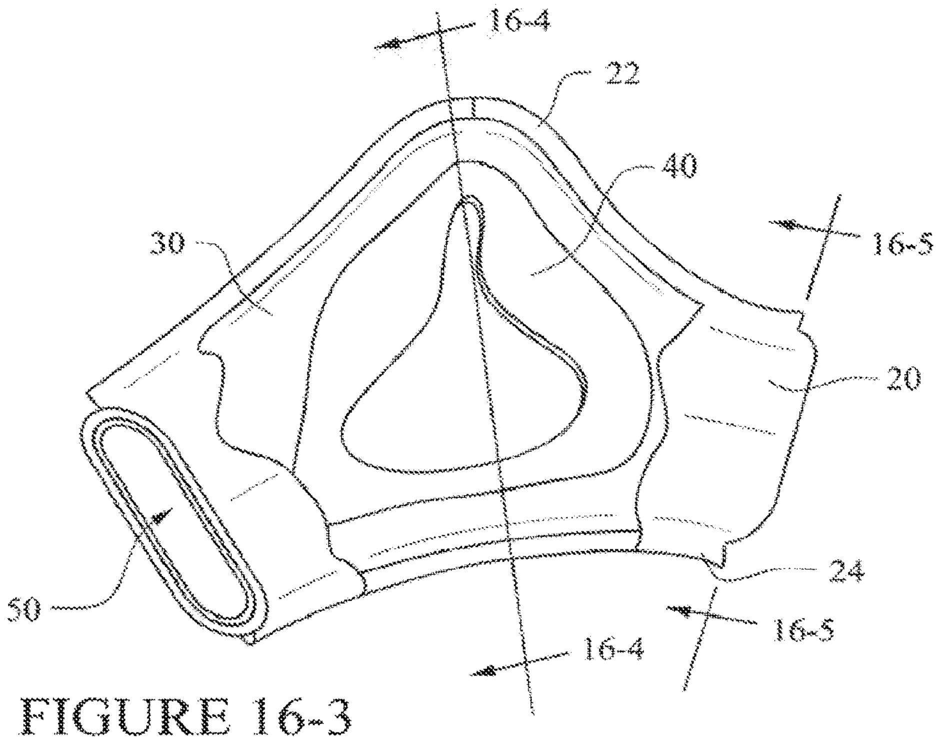
Figures 4, 16:
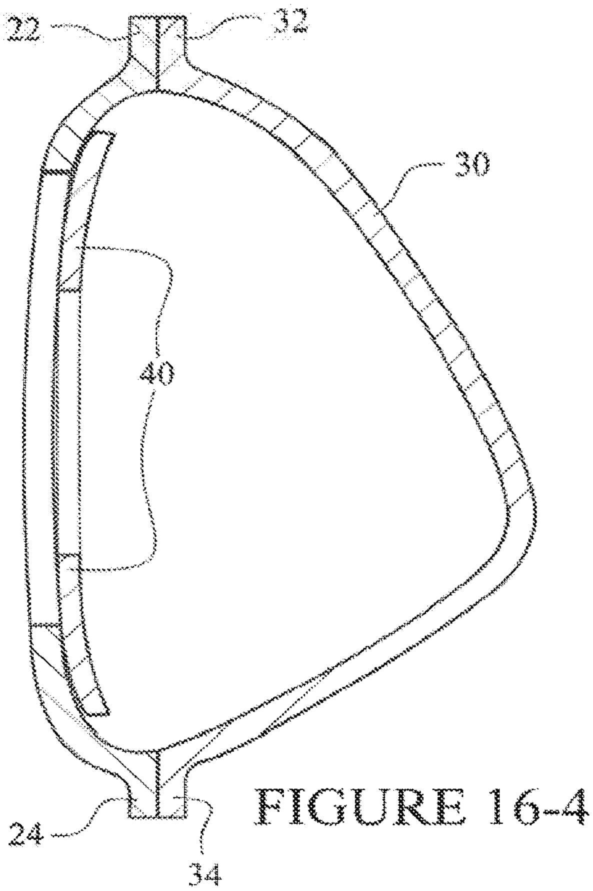
Figures 5, 16:
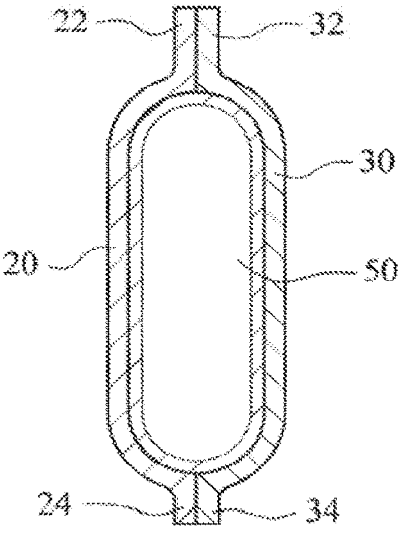

Referring to FIGS. 16-1 to 16-5, textile (e.g., fabric) mask parts (e.g., panels, seal member, cuffs) may be welded (e.g., radiofrequency, ultrasonic) together to form a mask. In addition to welding, mask parts may be glued, stitched and/or overmolded to join the parts. In order to deliver respiratory therapy, the textile panels should be airtight. Further, the stitching and welds should have minimal leakage. Accordingly, textiles having a tight weave and/or a coated textile (e.g., a polyurethane or silicone coated textile) may be used.

Referring to FIGS. 16-1 and 16-2, the upper 22 and lower 24 flanges of the back panel 20 and the upper 32 and lower 34 flanges of the front panel 30 may be clamped together and welded to connect the parts. The cuffs 50 may be positioned between the back panel 20 and the front panel 30 and welded in place.

The back panel 20 and the front panel 30 are preferably made of textile and may be thermoformed to obtain their shape. The seal member 40 may be welded or thermoformed onto the back panel 20.

The front panel 30 and the back panel 20 may be locally rigidized or softened (e.g., by altering the weight of the textile, laminating different density foams to the textile panels, and/or including semi-rigid frames).

As shown in FIGS. 16-3 and 16-5, the two cuffs 50 may be inserted into each end of the mask to allow connection with two air delivery tubes.

In an example, the front panel 30 and the back panel 20 may be welded while positioned inside out and then reversed after completion of welding to hide the weld seam.

Figures 1, 17:
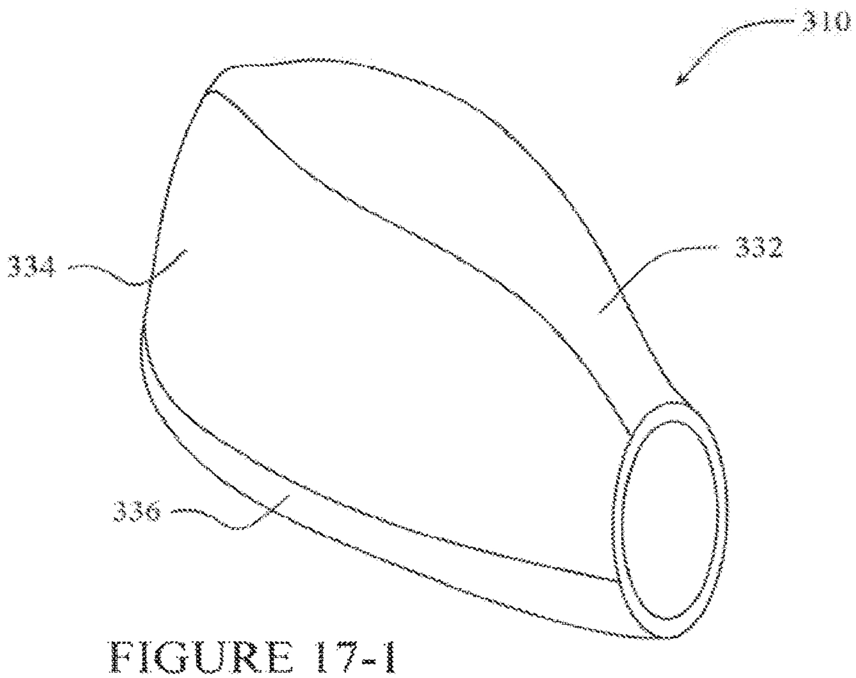
Figures 2, 17:
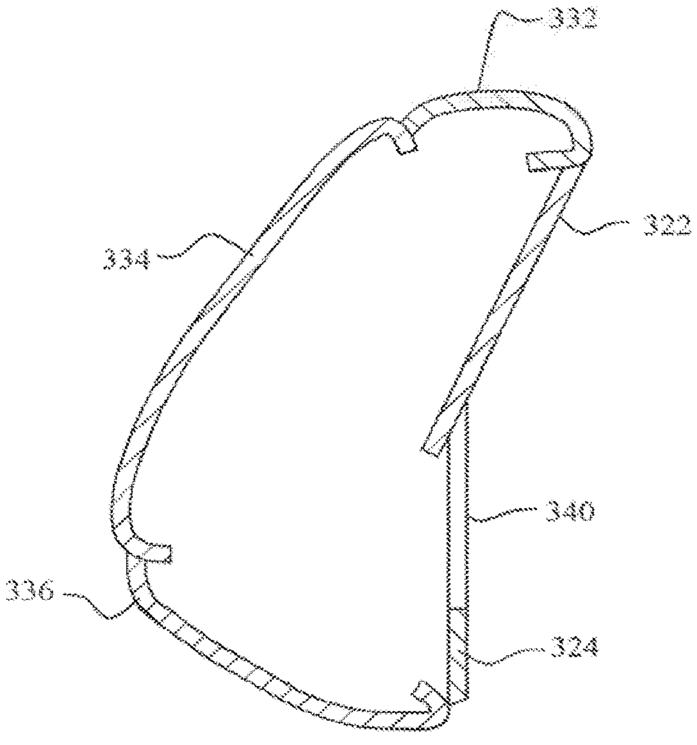
Figures 3, 17:
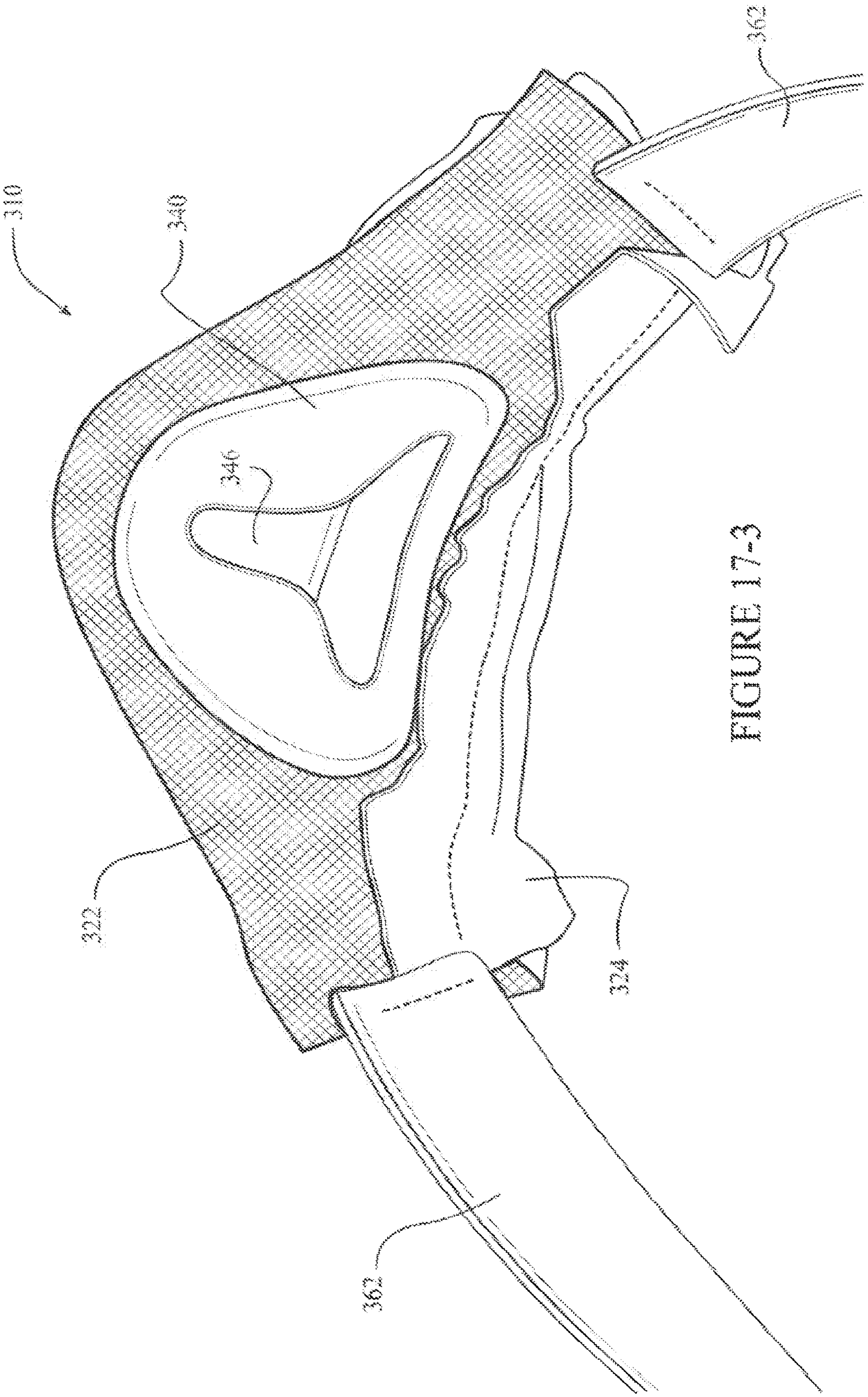
Figures 4, 17:
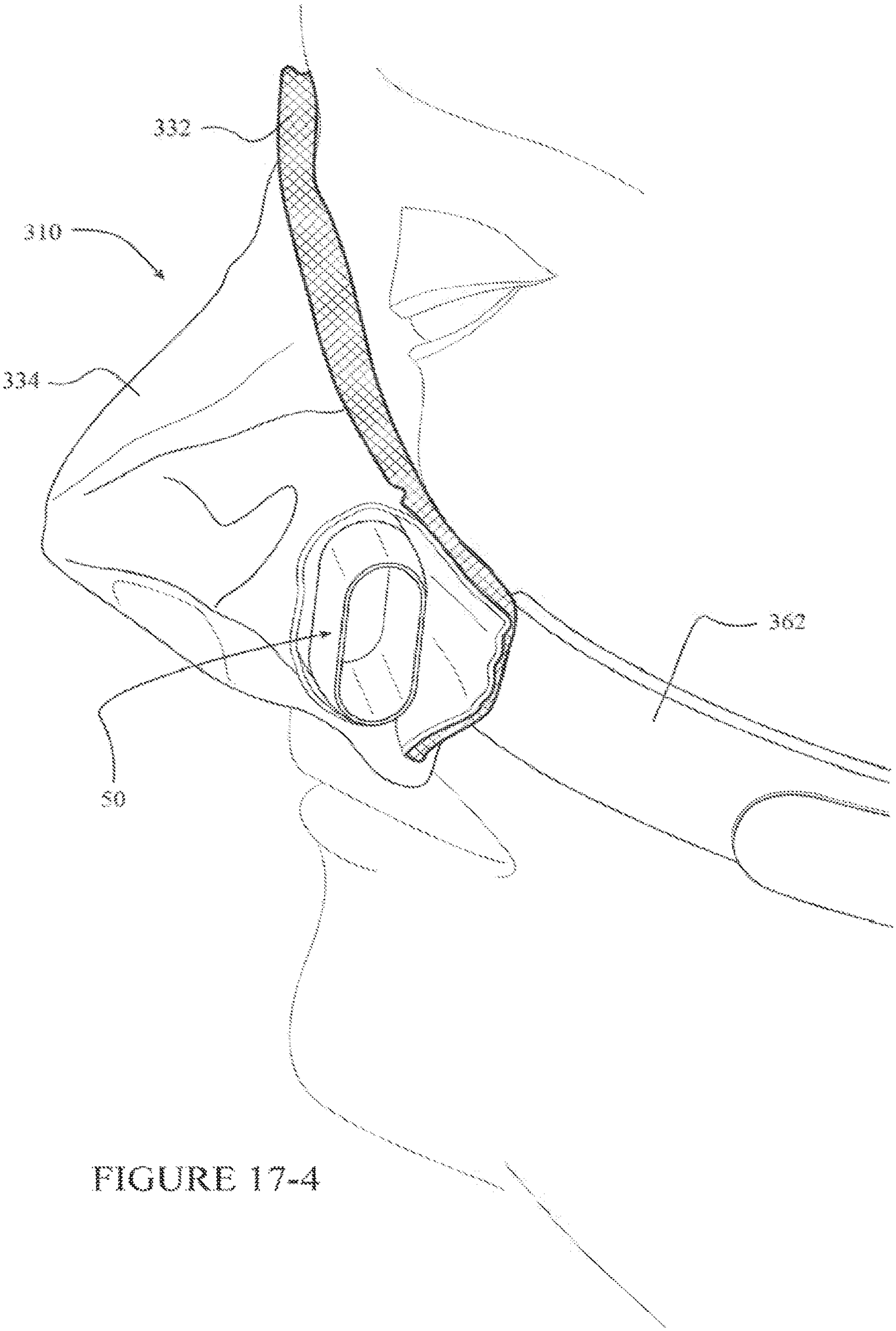
Figures 5, 17:
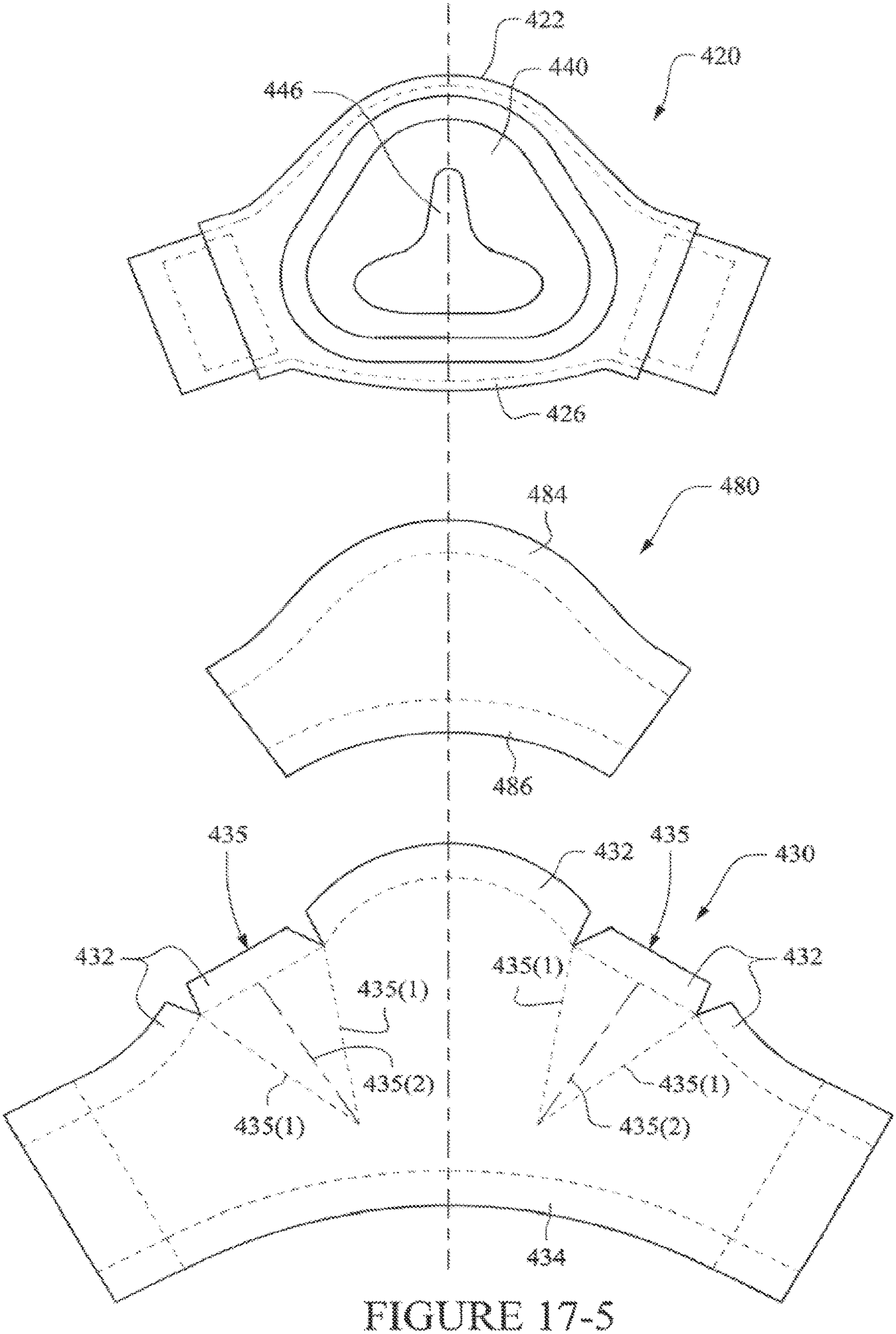

Although several examples described herein refer to a front panel and a back panel, it will be understood that masks in accordance with the disclosed technology may be constructed from any number of textile panels. For example, the mask 310 shown in FIGS. 17-1 to 17-4 is constructed on five textile panels. First 322 and second 324 panels extend over a back portion of the mask. The first panel has a seal member 340 formed thereon. The seal member 340 has an opening 346 to receive the patient's nose. Third 332, fourth 334, and fifth 336 panels are connected to one another and extend over a front portion of the mask. The third panel 332 connects to the first panel 322 and the fifth panel 336 connects to the second panel 324, as shown in FIG. 17-2. In the illustrated example, the panels 322, 324, 332, 334, 336 are stitched together. Some or all of the panels may have different material properties (e.g. panel 322 may be soft and comfortable as it may provide most of the interface with the patient's face). Panel 322 may be, for example, cloth, terry toweling, felt, or other soft fabric. Panel 324 may be a moisture wicking fabric as it is positioned proximate to the patient's nose and may absorb humidified exhaled air. Panel 334 may be made from a relatively stiff fabric as this panel may need to support the shape of the mask (e.g. a spacer fabric or reinforced woven). Panels 332 and 336 may be relatively flexible as these panels may need to conform to different patient's anthropometry (e.g. linen).

Cuffs 50 may extend from sides of the mask 310 and straps 362 may be connected to the mask, as shown in FIGS. 17-3 and 17-4.

In another example shown in FIG. 17-5, a back panel 420, a bottom panel 480, and a front panel 430 may be joined (e.g., by stitching) to form a mask. The back panel 420 includes a seal member 440 thereon having an opening 446. The back panel 420 further includes an upper tab 422 and a lower tab 426.

The bottom panel 480 may be positioned proximate to the patient's upper lip on the non-face contacting side of the mask. The bottom panel 480 includes an upper tab 484 and a lower tab 486. The front panel 430 may be positioned proximate the patient's nose bridge region on the non-face contacting side of the mask. The front panel includes an upper tab 432 and a lower tab 434. The front panel 430 may also include darts 435 or seams located on either side of a central, nose bridge engaging portion. The darts 435 may be sewn (e.g., along stitch lines 435(1) in a fold (e.g., along center line 435(2)) in order to give the front panel and hence the mask a three dimensional shape.

According to the present example, the darts 435 are first formed in the front panel 430. The dart center line 435(2) can be marked with dart stitch lines 435(1) positioned on both sides of the dart center line. The dart stitch line 435(1) is folded over the dart center line 435(2) and a stitch or other connection means is formed along the dart stitch lines to create a fold in the front panel. These folds create a three dimensional shape to bend the textile of the front panel so that the front panel is shaped to conform to curvature of face.

After the darts 435 have been formed in the front panel 430, the front panel can be stitched or otherwise connected to the bottom panel 480 by joining the upper tab 484 of the bottom panel 480 to the lower tab 434 of the front panel 430. The front 430 and bottom 480 panels may then be stitched or otherwise connected to the back panel. For example, the upper tab 422 of the back panel 420 may be joined to the upper tab 432 of the front panel 430, and the lower tab 426 of the back panel 420 may be joined to the lower tab 486 of the bottom panel 480.

4.0 Headgear

Headgear is used to effectively position the mask on the patient's face during treatment. The headgear may be adjustable to enable a single mask system to fit a wide range of people. Additionally, patients often feel the need to adjust their headgear on a daily basis.

Headgear adjustments can be broken down in to macro adjustments and micro adjustments. Macro adjustments refer to the larger adjustments that relate to the overall size of the mask (e.g., small size, medium size, large size). These adjustments are usually performed only once (e.g., during first time setup). Alternatively, the mask systems may be offered in 2 to 3 different size groups to eliminate the need for macro adjustment.

After the initial setup, only smaller (micro) adjustments are needed in response to leaks and/or face/neck movements for example. Micro adjustments refer to the smaller adjustments that might occur on a daily basis. These adjustments typically may be made to reduce leaks, accommodate for pressure sores on the patient's face, to adjust for neck movement in the standing vs. lying positions and/or to adjust for strap location on the patient's head which tends to vary from night to night.

The provision of elasticity in the headgear straps may cause the headgear to make micro adjustments automatically. Elastic straps hold a certain degree of "tolerance" for certain movements, such as neck flexing and head turning. In other words, the use of elastic straps may account for enough anthropometric variance within a certain size group that the headgear may be self-fitting and not require any fine adjustments.

Figures 1, 18:
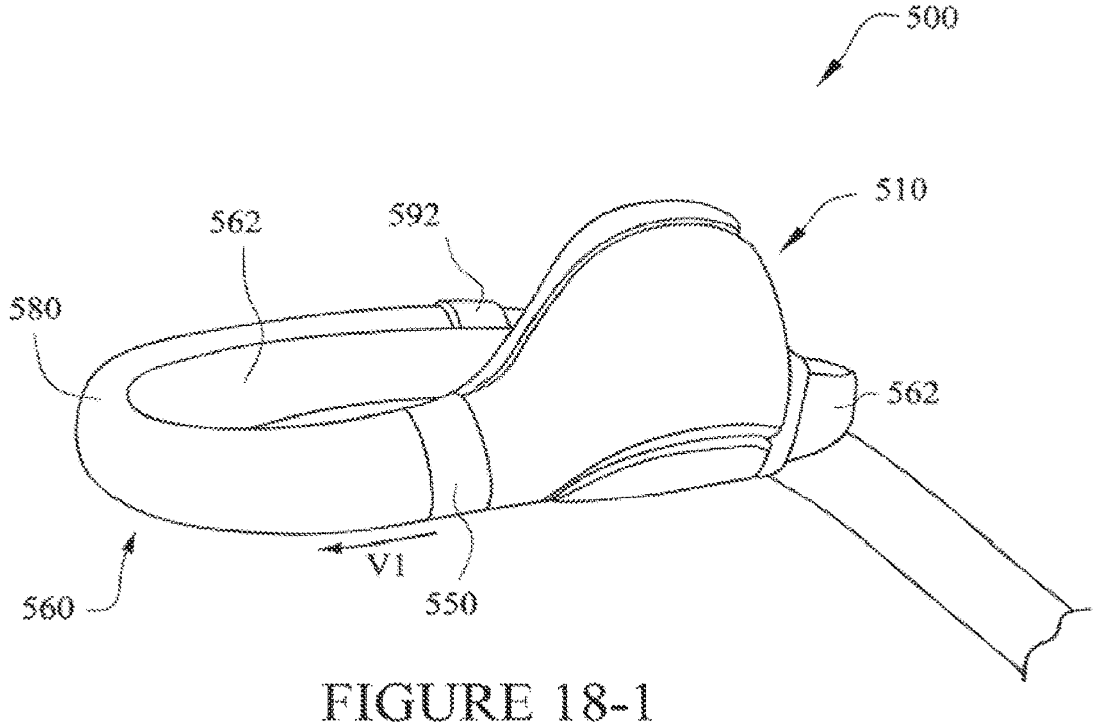
Figures 2, 18:
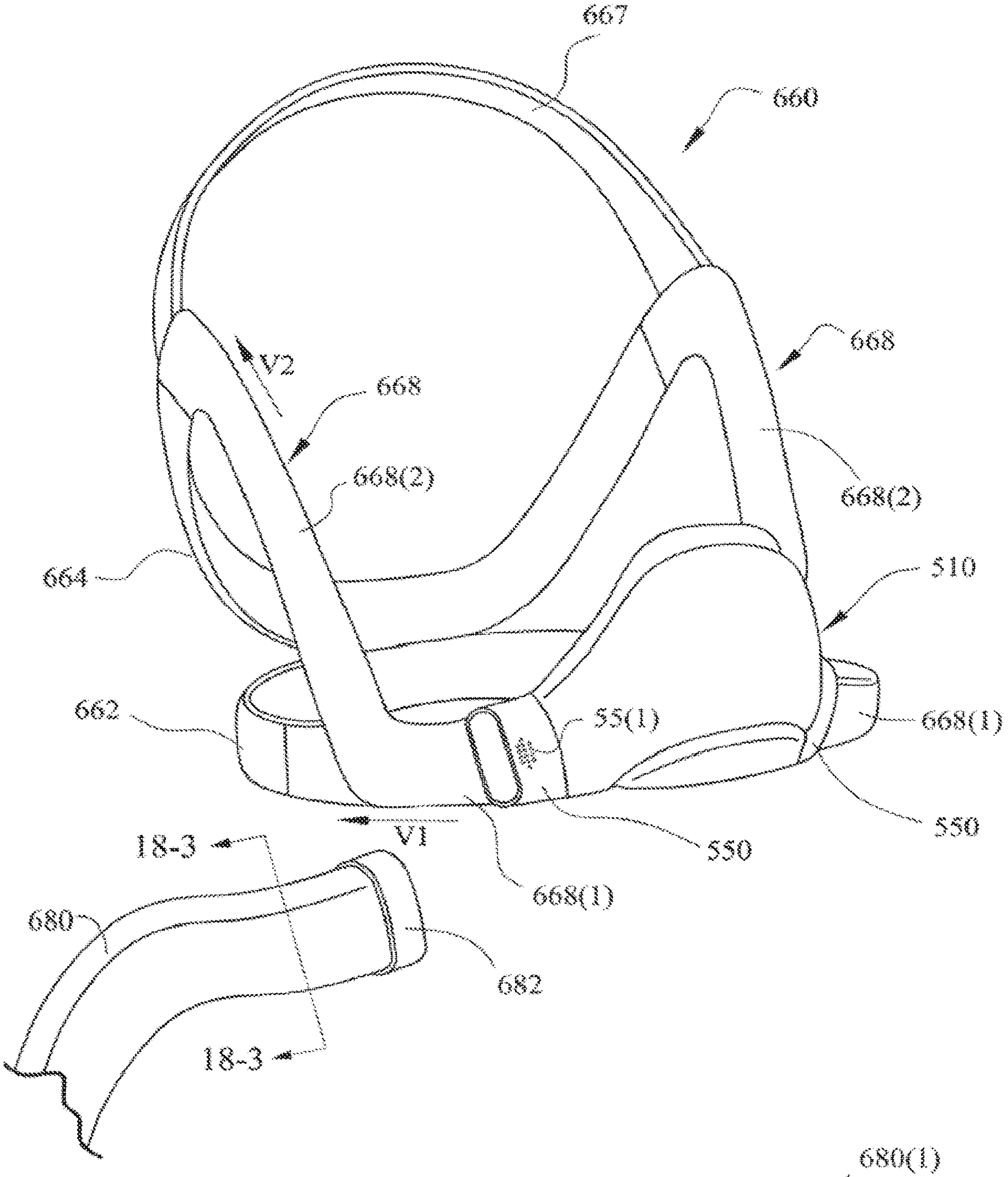
Figures 3, 18:
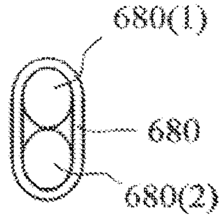

In an example shown in FIG. 18-1, a mask system 500 includes a mask having headgear 560 connected thereto. The headgear 560 includes a single strap (e.g., an elastic strap). The bottom strap is configured to extend along the patient's face (e.g., along the jaw bone) below the ears and around a rear portion of the patient's neck. A cuff 550 is connected to a side of the mask and connects to an air delivery tube 580. A tube anchor or anchor member 592 is attached to the strap 562 and receives the tube 580. The tube anchor is configured to provide a tube management system. The tube anchor may facilitate use of a textile mask as the tube anchor may absorb some of the weight of the tube. Since the textile mask is light (as compared to other masks such as plastic masks), the weight of the tube may adversely affect the mask. In addition, a single strap (as shown) is preferred as it is less obtrusive; however, this arrangement provides less support to the textile mask as compared to some other mask systems. Hence, the weight of the tube may tend to pull the textile mask away from the patient's face. The tube anchor may absorb part of the tube's weight and hence enable the textile mask to seal.

The provision of a single strap 562 keeps to a minimum the number of straps and connection points for the headgear. This arrangement reduces clutter and obstruction of the patient's vision, and also enhances ease of use. The strap 562 has a single vector V1 which exerts a tensile force on the mask as referred to in the examples described above.

Turning to FIGS. 18-2 and 18-3, a headgear 660 is shown. The headgear has a single side connection point on each side of the mask 510. The single side connection point is advantageous because it minimizes visual bulk and is easier for the patient to attach (as compared to multiple side attachment points). The headgear 660 includes a side strap 668 having a lower portion 668(1) connected to the mask 510 and an upper portion 668(2) extending upwardly from the lower portion. The lower portion 668(1) is adapted to be positioned along the patient's cheek or below the patient's cheek bone, in order to avoid obstructing the patient's eyes. The upper portion 668(2) is adapted to be positioned along the sides of the patient's face, extending between the patient's eyes and ears. An elastic bottom strap 662 is connected to the lower portion 668(1) of the side strap 668 and is configured to extend along the patient's face (e.g. along the jaw bone) below the ears and around a rear portion of the patient's neck. The elasticity in the bottom strap 662 adjusts automatically to accommodate for neck movements such as lowering or raising the head.

The upper portion 668(2) of the side strap 668 extends from the lower portion 668(1) of the side strap 668 upwardly at an angle. The side strap 668 may be rigidized to provide an upward vector to the mask 510. The side strap 668 may be shaped to conform to the shape of the patient's head or may be flexible enough to conform to the shape of the patient's head. In the illustrated example, the side strap has a first vector V1 corresponding to the lower portion 668(1) and a second vector V2 corresponding to the upper portion 668(2).

The headgear 660 further includes an elastic back strap 664 connected to the upper portion 668(2) of the side strap 668 and extending downwardly around the patient's head. The back strap 664 may abut against or be joined to the bottom strap 662 to form a double strap portion at a rear portion of the patient's head. Further, a top strap 667 is connected to left and right upper portions 668(2) of the side straps 668 and extends over the top of the patient's head. The top strap 667 may apply an upward force to the side straps 668 thereby providing an upward vector to the mask.

An air delivery tube 680 may be connected to a cuff 550 via a tube connection 682 disposed at an end of the air delivery tube 680. The cuff 550 may comprise vent holes 55(1) to exhaust expired gases. The cuff 550 may include 1-100 vent holes, for example about 10-30 vent holes, for example about 20-50 vent holes, for example about 3-20 vent holes, for example about 40-70 vent holes, for example about 50-80 vent holes. As shown in FIG. 18-3, the air delivery tube 680 may comprise two channels or lumens 680(1), 680(2). Alternatively, the air delivery tube 680 may comprise a single lumen in order to increase manufacturing efficiency and reduce impedance (as compared to a double lumen tube).

Figures 4A, 18:
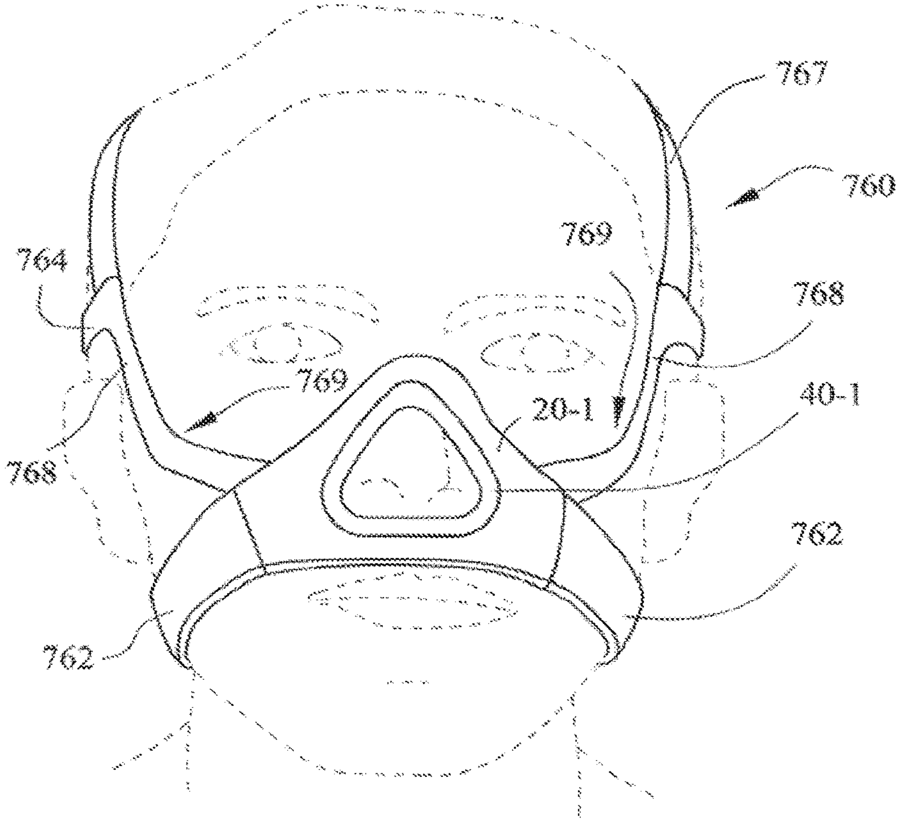
Figures 4B, 18:
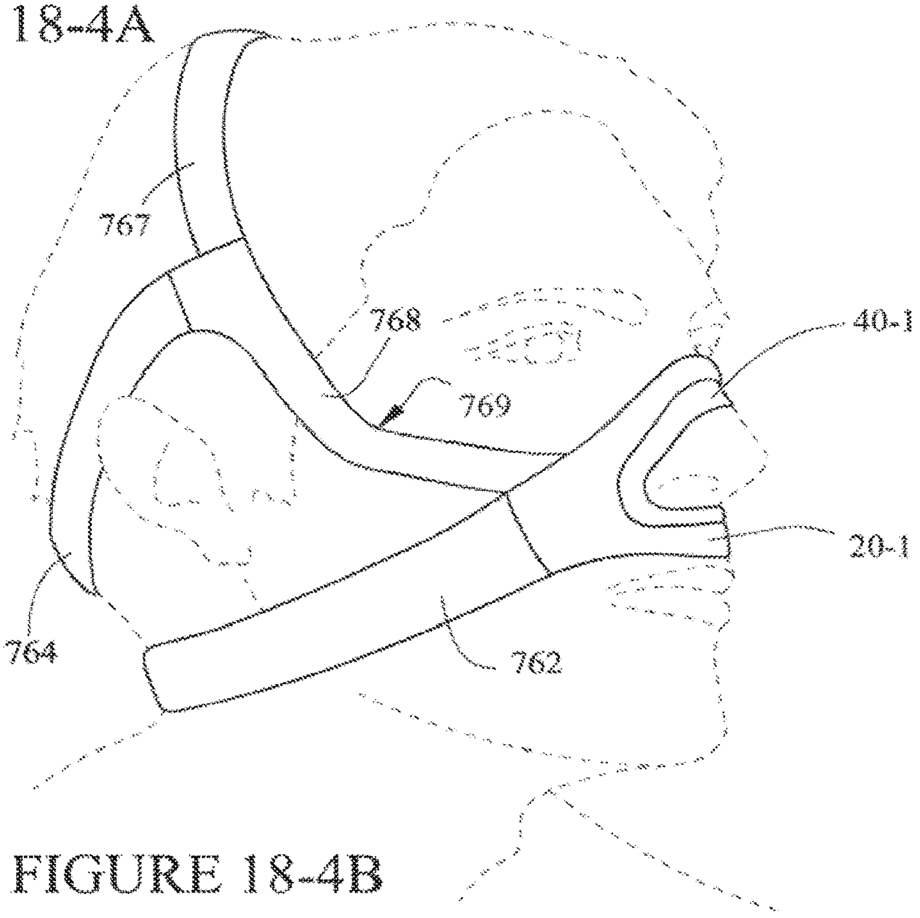
Figures 5, 18:
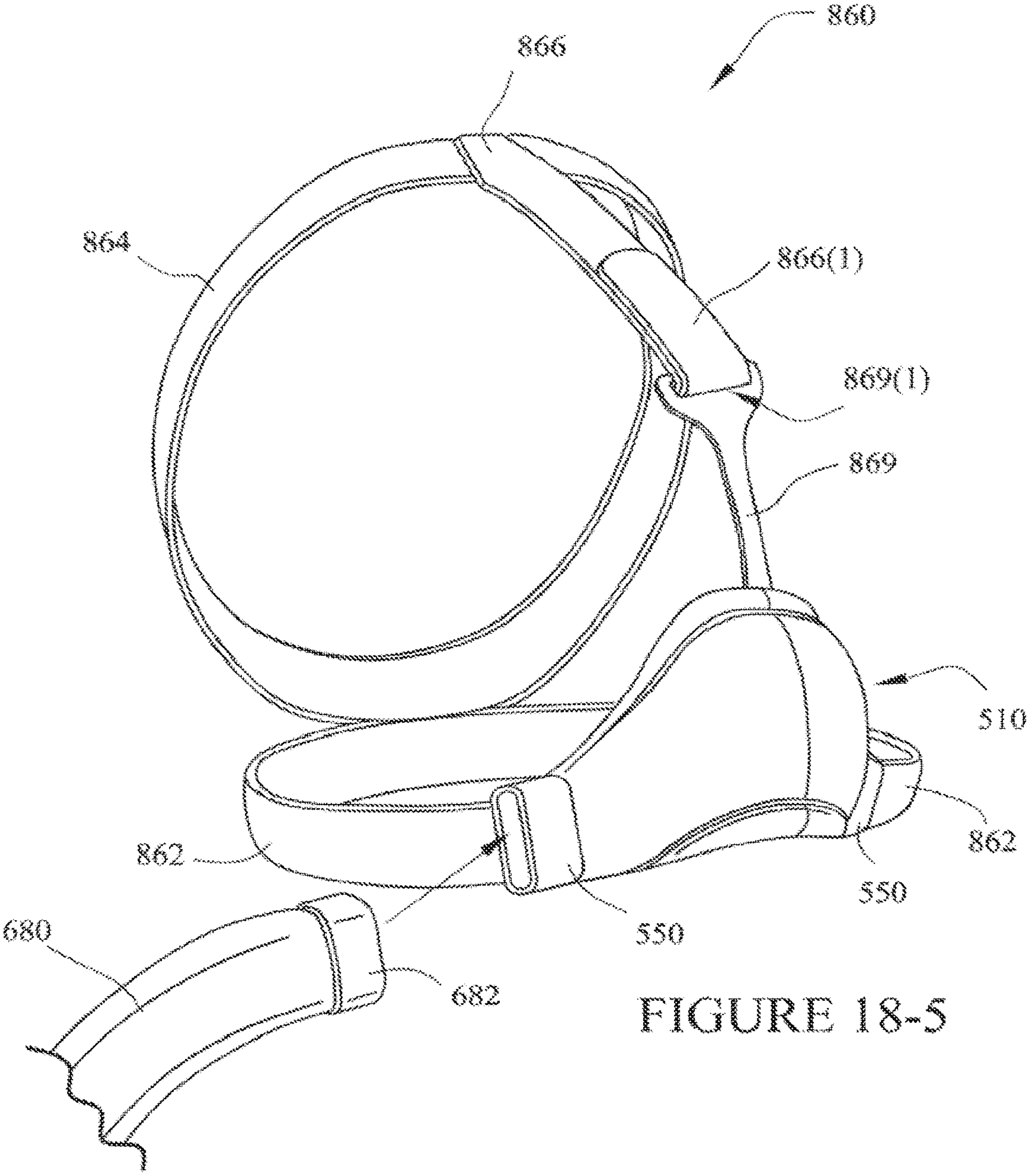

Referring to FIGS. 18-4A and 18-4B, headgear 760 is shown. The headgear 760 includes an elastic bottom strap 762 extending along the patient's face (e.g., along the jaw bone) below the ears and around a rear portion of the patient's neck and connecting to side portions of the mask (e.g., back panel 20-1). As mentioned above, the elastic bottom strap 762 can adjust automatically to accommodate for neck movements such as lowering or raising the head which may cause the length of the bottom strap 762 to change.

In an alternative example, the straps may not be elastic or may be a combination of elastic and non-elastic, thus incorporating an adjustment mechanism (e.g. hook and loop material). Hence, the strap may have macro adjustment through the adjustment mechanism and micro adjustment through the elastic portion of the strap.

Side straps 768 connect to side portions of the mask (e.g., back panel 20-1). In another example, the side straps may connect to the bottom strap 762, or even partially to both the mask and the bottom strap. The side straps 768 have a curve 769 or bend which allows the side straps 768 to extend in a manner that avoids obstruction to the patient's vision. The side straps 768 may include a first portion on one side of the curve 769 and a second portion on the other side of the curve, and the second portion may extend relatively more upwardly than the first portion. (i.e. following substantially along patient's cheek bones then tracing up between patient's eye and ear). The side straps 768 may be rigidized to add support and/or an upward vector to the cushion. Side and top straps may be optional i.e. the patient can selectively attach these straps if required.

A top strap 767 is connected to respective side straps 768 and extends over the top of the patient's head. The top strap 767 may apply an upward force to the side straps 768 thereby providing the upward vector to the mask (which may assist with preventing the tube weight from pulling the mask away from the patient's face).

Further, a back strap 764 is connected to respective side straps 768 and extends around the patient's head (e.g., around the occiput).

Turning to FIG. 18-5, headgear having a three-point connection to a mask is shown. The headgear includes an elastic bottom strap 862 extending along the patient's face (e.g., along the jaw bone) below the ears and around a rear portion of the patient's neck and connecting to side portions of the mask (e.g., back panel 20-1), as mentioned above. An upper connector 869 provides the third point of connection with the mask 510 and extends from an upper portion of the mask to connect to a front strap 866.

The upper connector 869 may be relatively light and flexible and may be constructed of a plastic such as nylon, polypropylene or polycarbonate. Alternatively, the upper connector 869 may be constructed of a fabric or textile. The upper connector 869 may also be constructed of a combination of materials such as a fabric with a plastic rigidizer. The upper connector 869 could be elastic or non-elastic. Ideally, the upper connector 869 is thin to avoid the patient's eyes and line of sight. Preferably, the upper connector 869 may be padded or selectively padded to avoid marking the patient's forehead or region of the face.

A crown strap 864 forms a loop intended to encircle the crown the of the patient's head. A lower extent of the crown strap 864 may be joined with the bottom strap 862 to provide form to the headgear 860 when it is not worn, and further to more reliably locate the headgear on the patient's head.

A front strap 866 extends from an upper portion of the crown strap 864 and connects to the upper connector 869. For example, the upper connector 869 may have a slot 869(1) through which the front strap 866 is looped. The front strap 866 further includes an attachment portion 886(1) (e.g., hook or loop material) configured to fold back onto and attach to the front strap 866 (which for example may be configured with the mating portion of the hook or loop material).

Figures 6A, 18:
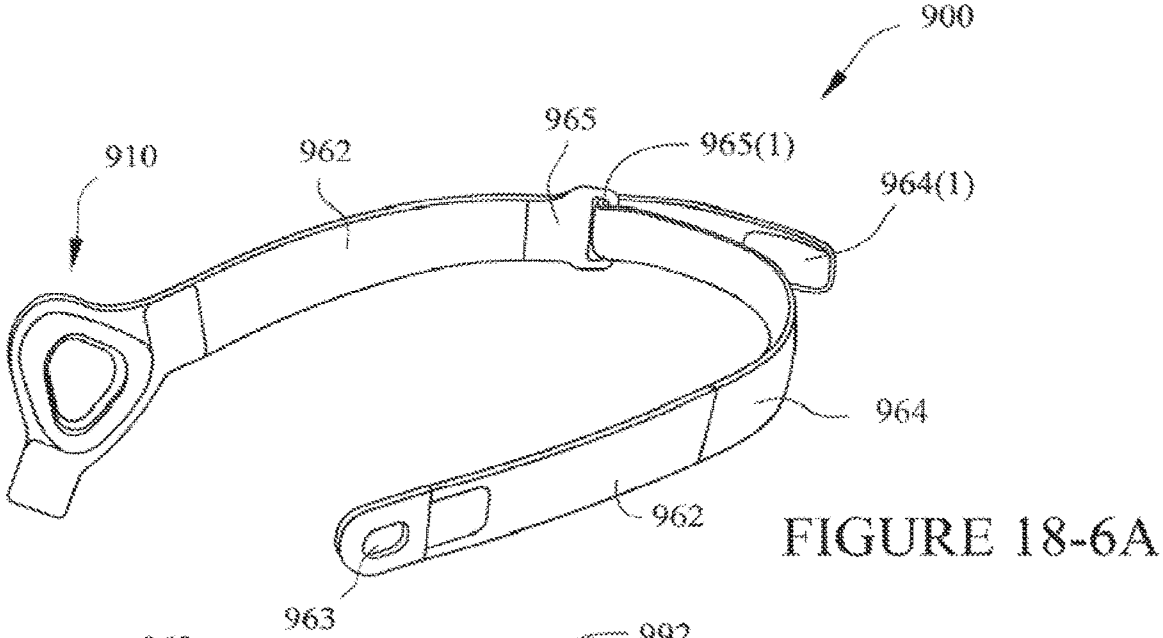
Figures 6B, 18:
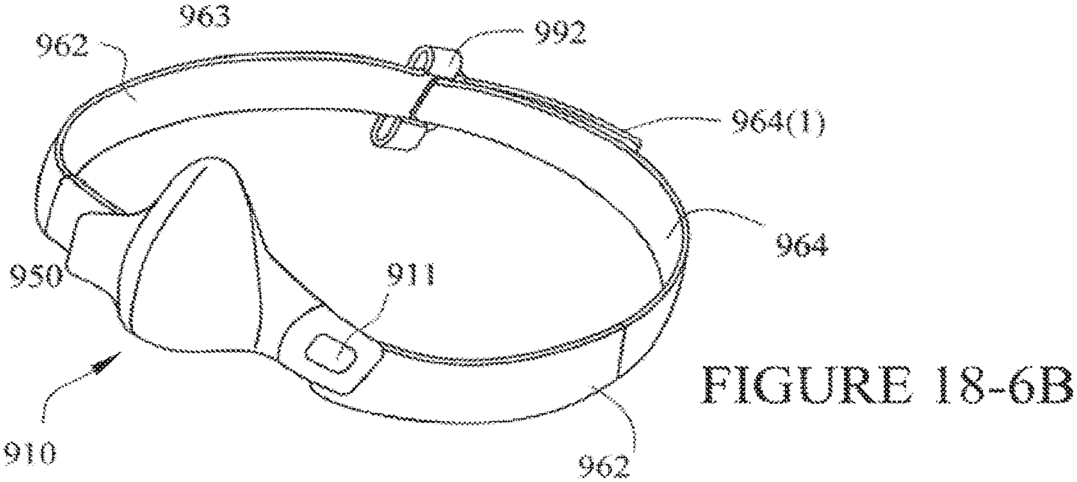
Figures 6C, 18:
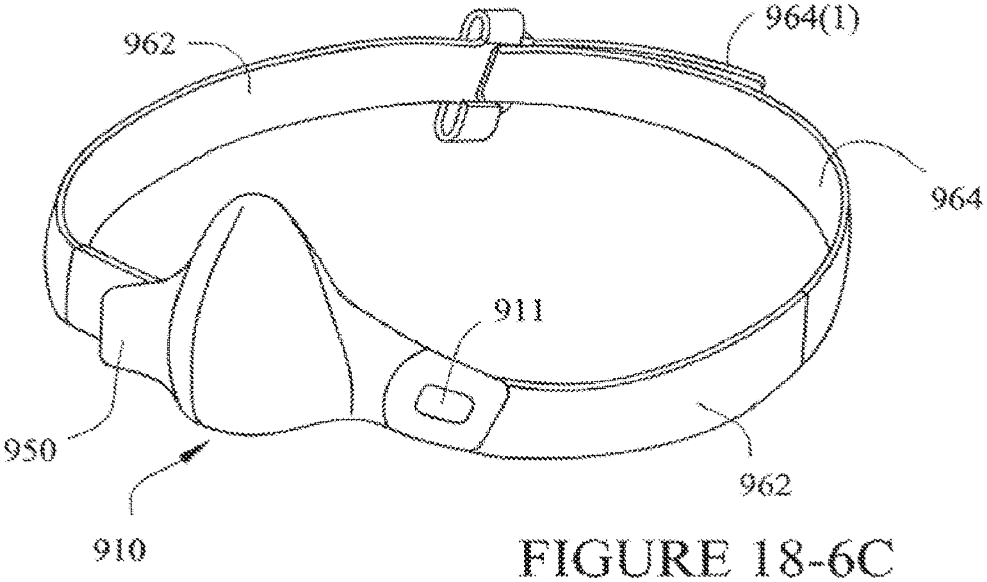
Figures 6D, 18:
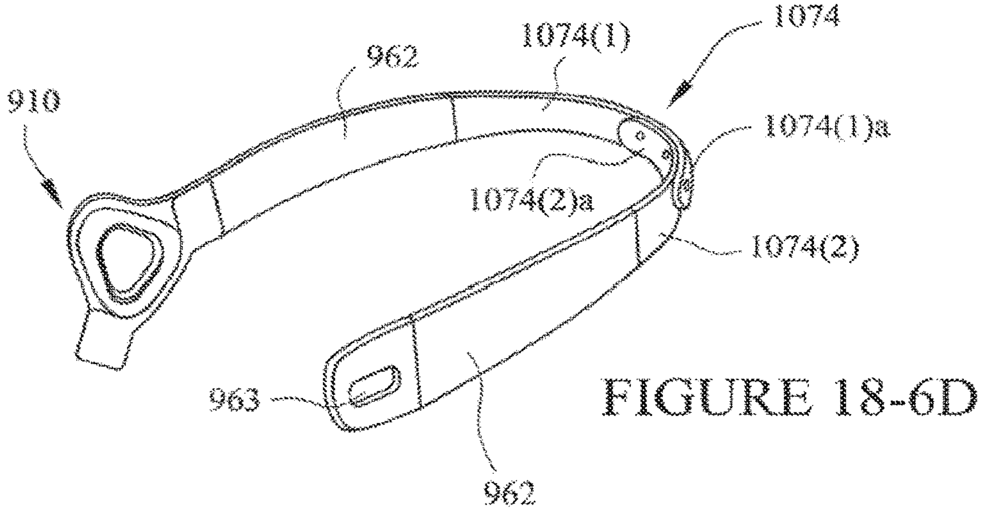
Figures 6E, 18:
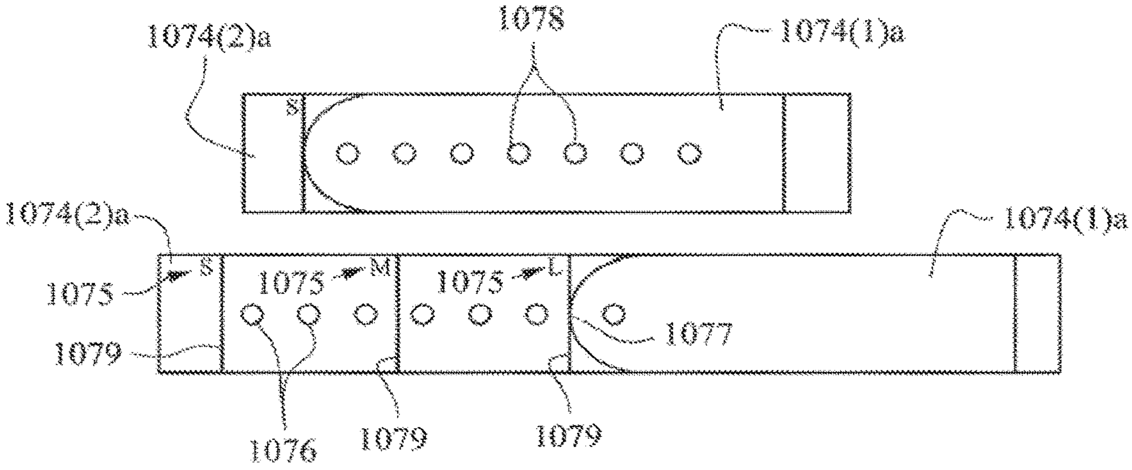
Figures 7A, 18:
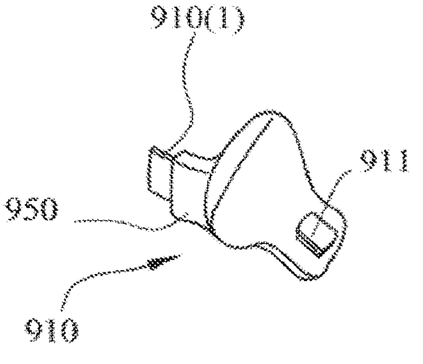
Figures 7B, 18:
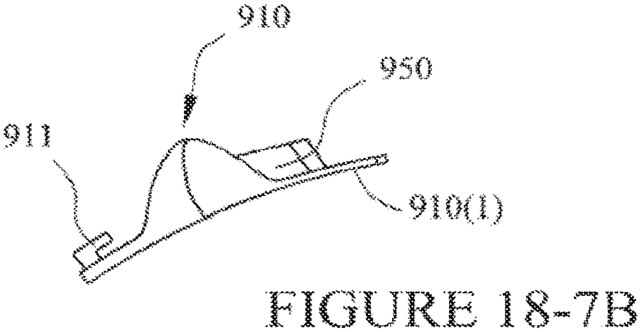

Referring to FIGS. 18-6A to 18-7B, a mask system 900 includes a mask 910 connected to a bottom strap 962. As best shown in FIGS. 18-7A and 18-7B, one end of the mask 910 includes a cushion tab 910(1) which may be connected directly (e.g., sewn) to the bottom strap 962. A cuff 950 is positioned adjacent the cushion tab 910(1) and configured to connect to an air delivery tube. The other side of the mask 910 may include a connector 911 (e.g., a raised L-shaped tab) configured to be received in a connecting member 963 (e.g., an opening) formed in the bottom strap 962.

The bottom strap 962 (i.e., a front portion of the bottom strap) is elastic to provide for micro adjustments. The bottom strap 962 may have a rear portion 964 including an adjustable connection that provides for macro adjustments. The rear portion 964 may be elastic, non-elastic or have a different (e.g., lower) elasticity as compared to the bottom strap 962. In an example, a connector 965 including a slot 965(1) is connected to a first side of the bottom strap 962. The rear portion 964 is connected to the second side of the bottom strap 962 and is looped through the slot 965(1). The rear portion 964 further includes an attachment portion 964(1) (e.g., hook or loop material) to allow the length of the rear portion 964 to be adjusted.

In another example, only one side of the bottom strap 962 may be elastic and the other side may have an adjustable connection, as shown in FIG. 18-6C.

In another example shown in FIGS. 18-6D and 18-6E, a rear portion 1074 of the bottom strap 962 may include a first portion 1074(1) connected to a first side of the bottom strap 962 and a second portion 1074(2) connected to a second side of the bottom strap 962. The first portion 1074(1) may include an attachment portion 1074(1)*a* having holes 1076 formed therein to receive plugs 1078 formed on an attachment portion 1074(2)*a* of the second portion 1074(2).

As shown in FIG. 18-6E, the first and second portions 1074(1), 1074(2) may have visual clues and/or markers corresponding to headgear sizes. In an example, the attachment portion 1074(1)*a* may have an edge 1077 configured to be aligned with a visual marker (e.g., a line, groove, embossment, etc.) that is associated with a visual clue 1075 (e.g., the letters S, M, L, or other indicators of small, medium, large) of the size of the headgear. For instance, when the edge 1077 is aligned with the visual marker 1079 associated with (or positioned next to) the visual clue 1075 "L," the patient will understand that the headgear has been adjusted to its "large" size.

As shown in FIG. 18-6B, a tube anchor 992 may be attached to the bottom strap 962 to hold an air delivery tube. The tube anchor 992 wraps around the tube to maintain the tube in position relative to the headgear. The tube anchor 992 could be a loop made from, for example, elastic, plastic or other materials. The loop may be stitched, welded, molded or otherwise formed into a continuous loop. The loop may be selectively openable or may be stretchable to receive the tube.

It may be preferable to position the tube anchor 992 at the rear of the patient's head. In this location, the tube may be positioned perpendicular to a flow generator and thus have less tube drag. In addition, if the tube anchor is positioned at the nape of the patient's neck, it may be more comfortable for the patient and may be less likely to dislodge as it is protected in the curved portion of the patient's neck underneath the occiput.

5.0 Swivel Elbow

In an example, a mask system may include an air delivery conduit 1180 that is rotatable with respect to the mask 1110. The air delivery conduit may be connected to the mask via an elbow 1118. The elbow has a first leg and a second leg having an angle (e.g., a 90° angle) therebetween. The first leg of the elbow 1118 is connected to a connector portion 1180(1) of the air delivery conduit 1180. The second leg of the elbow 1118 is connected to an annular elbow connection 1115 of the mask 1110. The elbow 1118 and the annular elbow connection 1115 have a mating arrangement that allows the elbow to swivel with respect to the annular connection 1115. A suitable elbow is described in US Provisional Patent Application U.S. 61/648,807, filed 18 May 2012, which is incorporated herein by reference in its entirety Annular elbow connection 1115 may be connected or form part of an internal mask rigidized section (e.g. rigidized frame) so as to avoid exerting force on the textile portion of the mask. The rigidizer may also be connected to the cuffs and the headgear therefore transferring the weight of the tube and forces applied to the tube to the headgear. This may assist in stabilizing the mask in position. Alternatively, the annular elbow connection 1115 may be attached to an unsupported section of the textile mask thereby allowing the mask to flex and move freely when a force is applied to the tube. That is, because the textile is flexible, it can readily adapt its shape depending on the forces applied to it via the tube, and hence may decouple tube drag forces from the sealing portion of the mask.

6.0 Tube Management

As the patient moves during the night, forces (e.g., drag) exerted on the air delivery tube (or tube) may be transferred to the mask in a manner that disrupts the seal with the patient's face. Thus minimizing tube drag may ensure that a good seal is maintained and in turn enhance the effectiveness of treatment.

In an example, tube drag forces may be minimized or prevented by anchoring the tube on the patient's body (e.g., at the back of the head on the headgear) so as to support part of the weight of the tube. This arrangement leaves only a short portion of the tube to hang between the mask and the anchor point which substantially reduces the amount of tube weight that is supported by the mask.

To facilitate routing the tube behind the patient's head to connect with a tube anchor attached to the headgear, the tube may be connected to the mask at a side portion of the mask. This arrangement reduces the apparent bulk (size) of the mask system making it less obtrusive and more aesthetically appealing. The side connection also provides the shortest distance from the mask to the anchor point, thereby minimizing obstruction to the patient caused by the size of the mask system as well as minimizing the risk of tube drag.

Figures 1, 19:
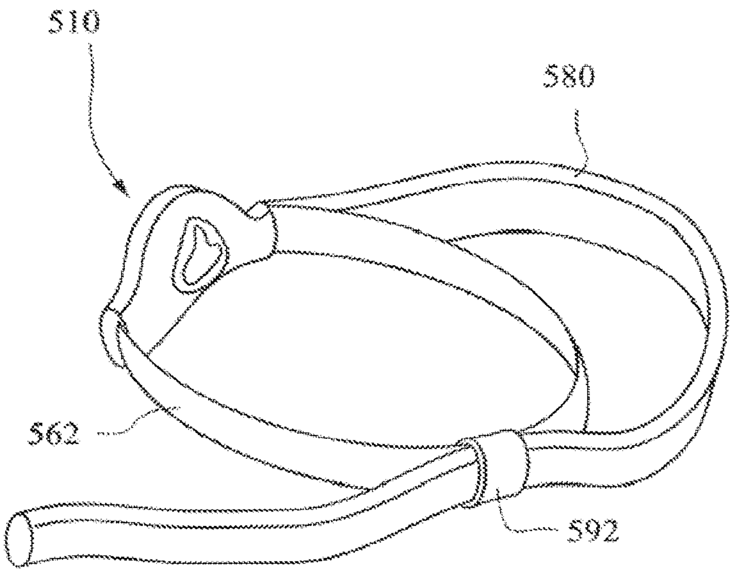
Figures 2, 19:
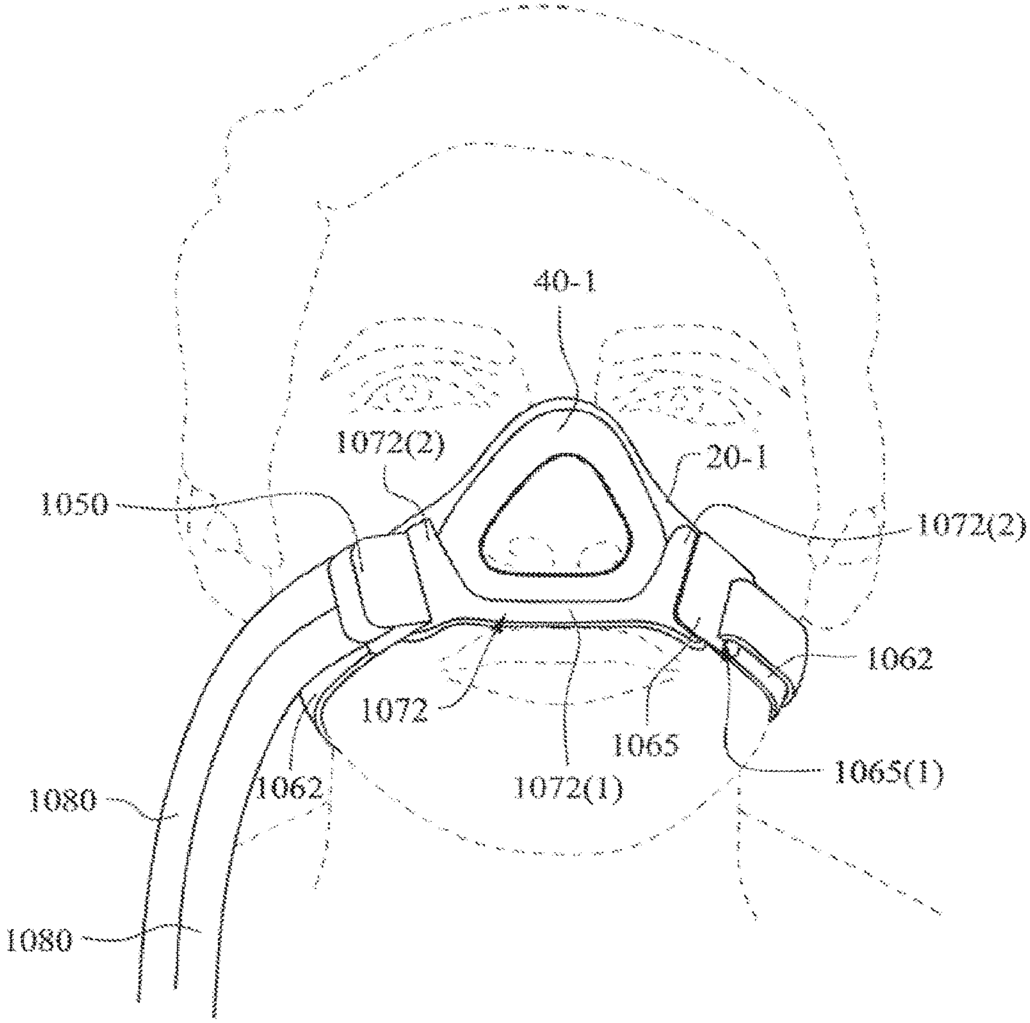
Figures 3, 19:
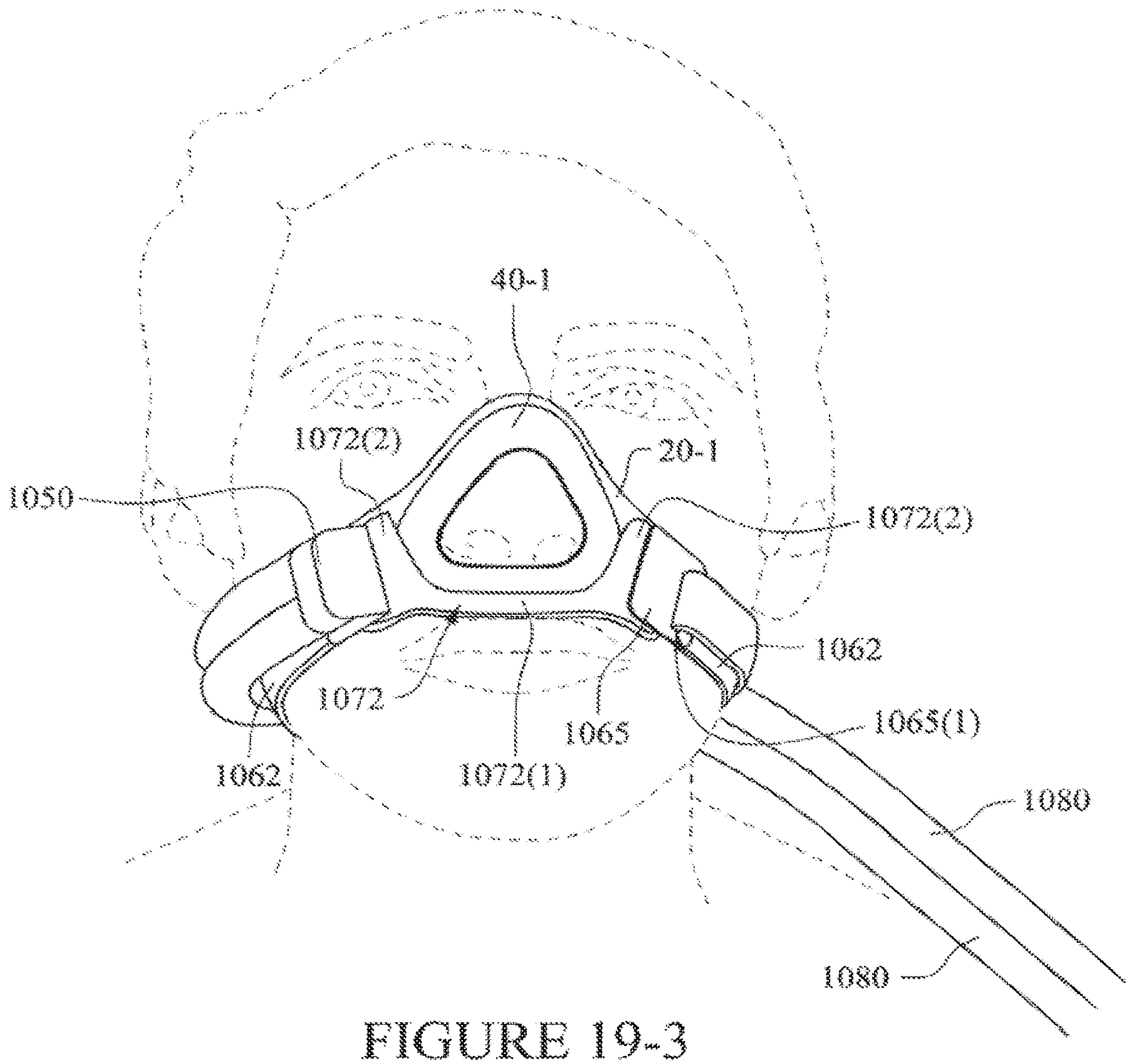
Figures 4, 19:
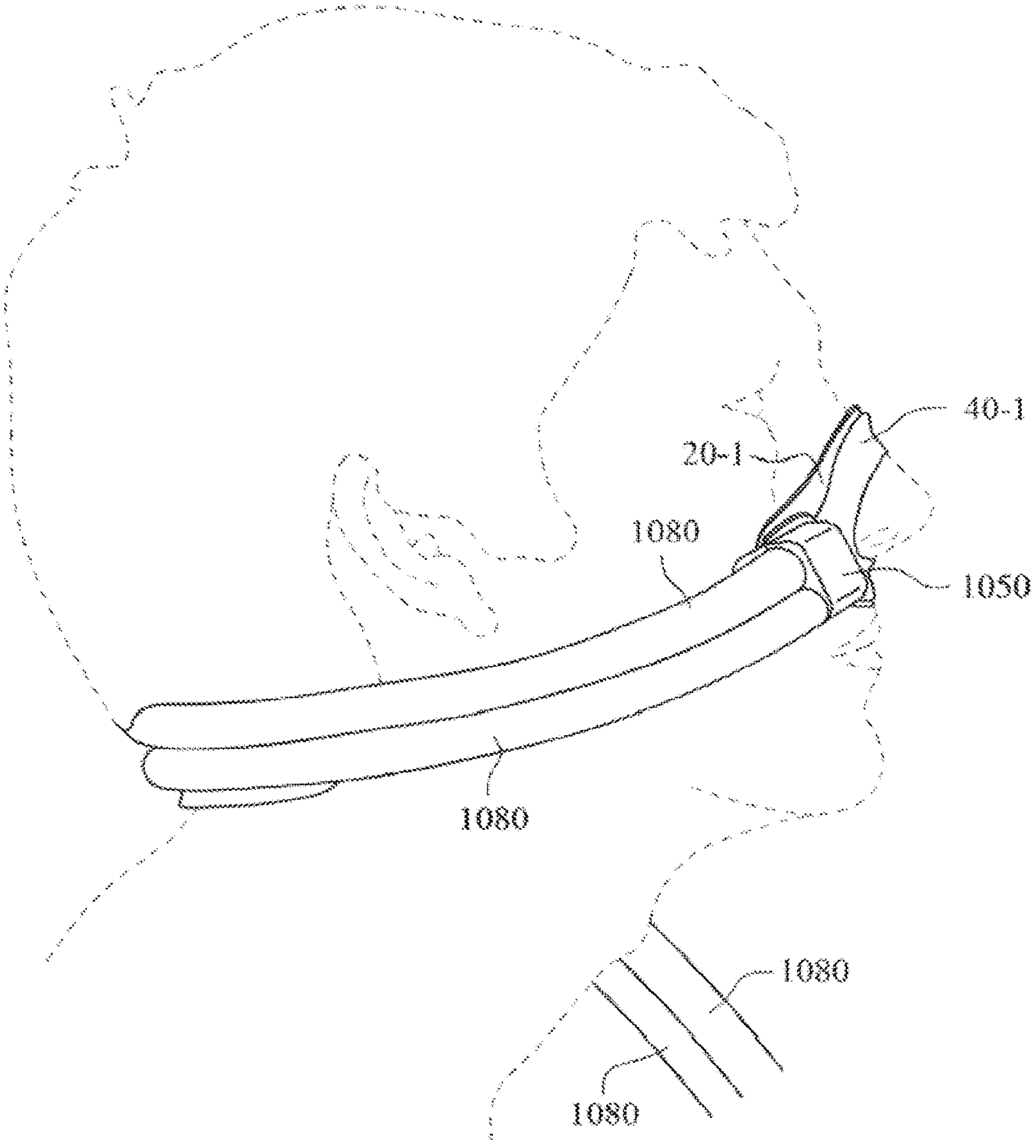
Figures 5, 19:
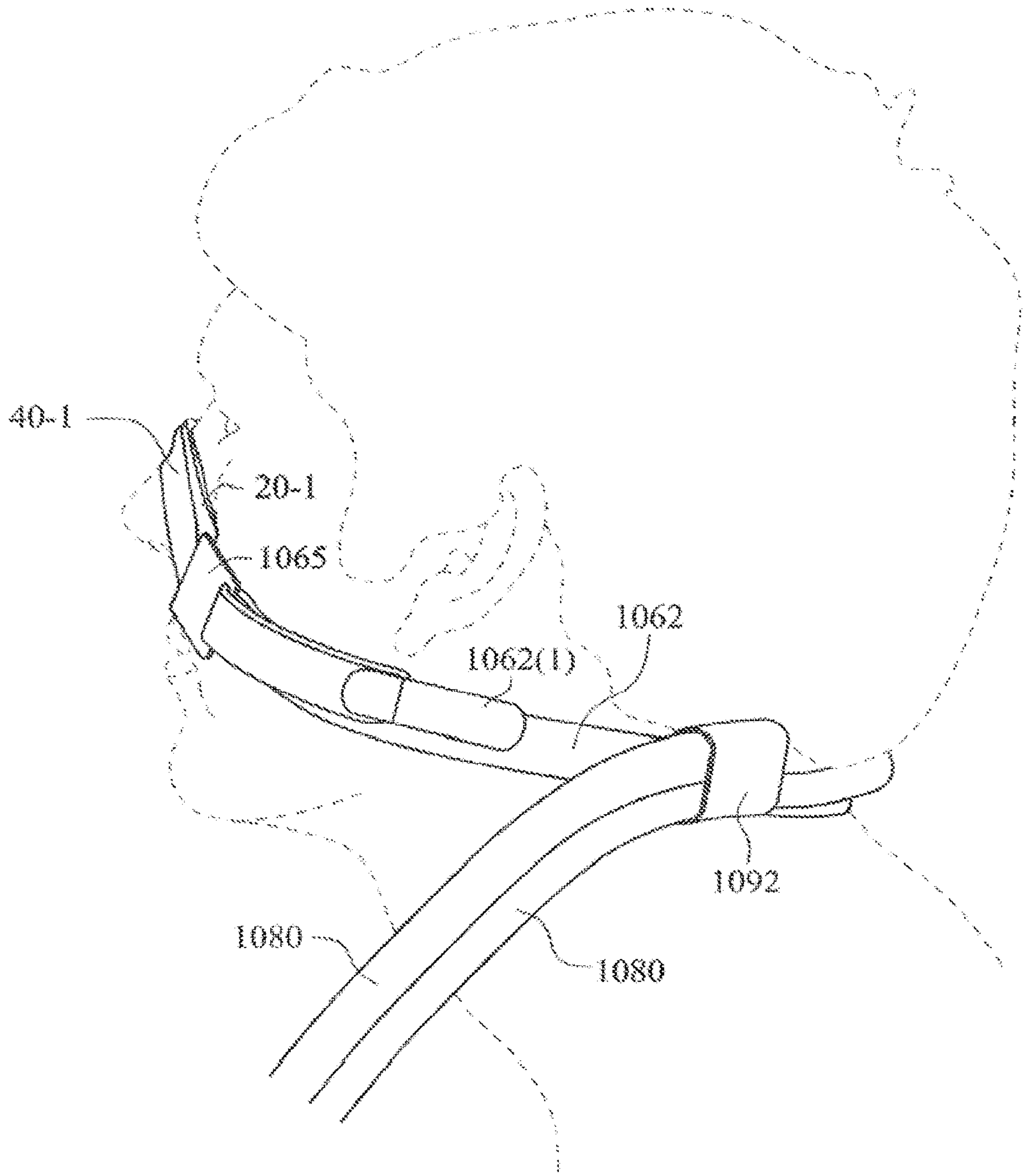
Figure 20:
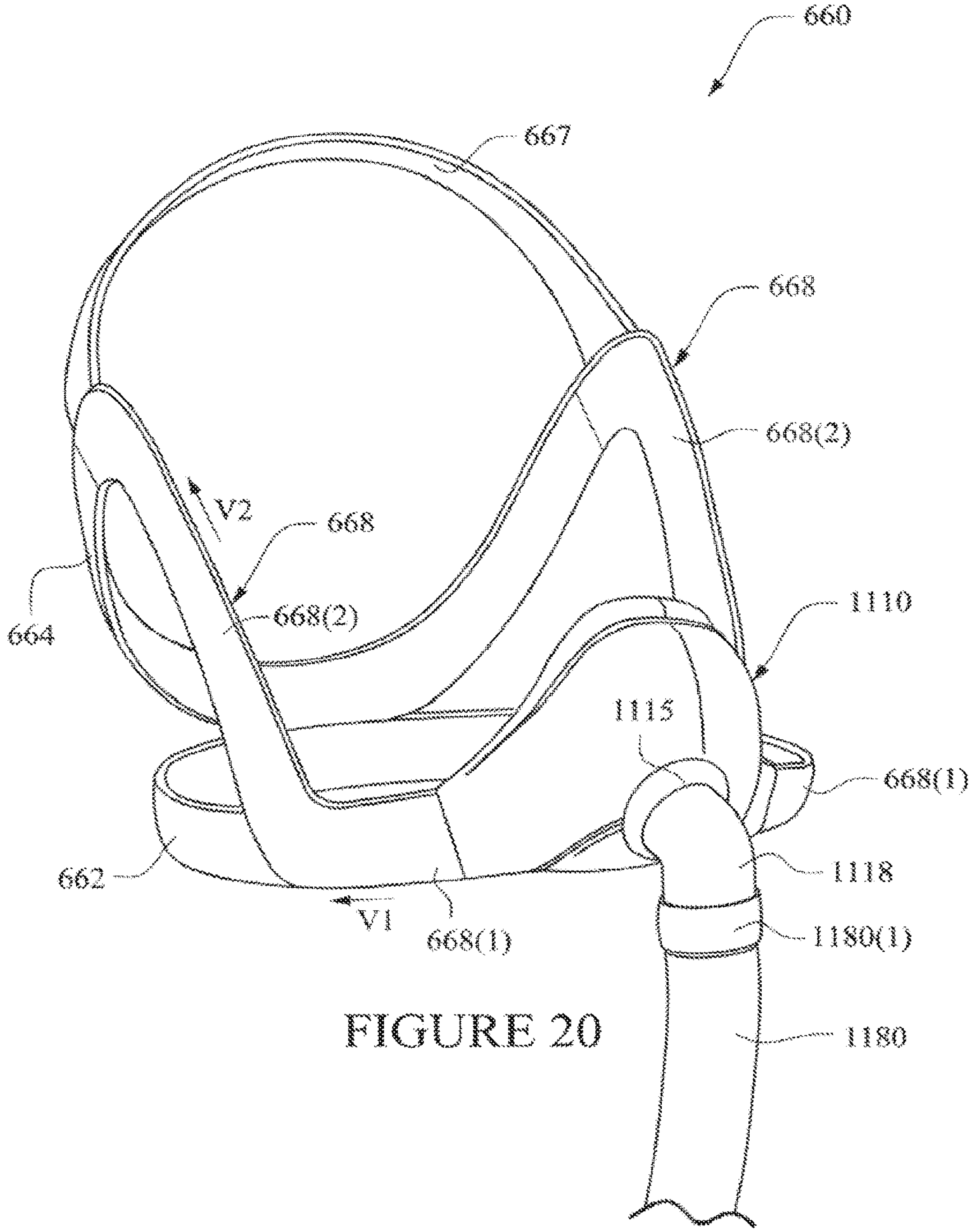
FIG. 20 is a perspective view of a mask system according to an example of the disclose technology.

In the illustrated example of FIGS. 19-1 to 19-5, to facilitate supporting the tube with an anchor attached to the headgear, it is preferable to route the tube along the same line as the bottom strap (e.g., along the jaw bone). By this arrangement, it is likely that the patient's head will rest on the tube. To enhance comfort to a patient having part of their body lying over the tube, a tube having a flat profile may be used to provide a flat or even surface for the patient to rest against. A flat tube routed over a headgear strap may reduce the visual bulk of covering and disguising the tube against the strap and/or create a simpler design by streamlining the components.

Alternatively, in another example, the tube may run freely down beside the mouth and away from the mask (flexing in the major and/or minor tube axis directions in relation to the tube cross section).

In any case, a more compliant or flexible tube may allow for the greatest flexibility in tube orientation.

Referring to FIGS. 19-2 to 19-5, a mask system utilizing a tube anchor attached to the headgear is shown. The mask system includes a back panel 20-1 having a rigidizer frame 1072 layered thereon. The rigidizer frame includes an interconnecting portion 1072(1) and cheek portions 1072(2) attached to opposite ends of the interconnecting portion.

A bottom strap 1062 is connected to side portions of the mask (e.g., the back panel 20-1 or rigidizer frame 1072) and extends along the patient's face (e.g., along the jaw bone) below the ears and around a rear portion of the patient's neck. One side of the mask may include a connector 1065 (e.g., attached to the back panel 20-1) having a slot 1065(1) formed therein. The bottom strap 1062 may be routed through the slot 1065(1) and folded back onto itself to adjust tension in the bottom strap 1062. The bottom strap 1062 may include an attachment portion 1062(1) (e.g., hook or loop material) to secure to the bottom strap.

A cuff 1050 is attached to a side portion of the mask (e.g., the back panel 20-1 or rigidizer frame 1072) and provides a connection point for the air delivery tube 1080. In the illustrated example, the mask system may include two air delivery tubes 1080 connected to the cuff 1050 in a side-by-side arrangement.

As best shown in FIG. 19-5, a tube anchor 1092 is attached to the bottom strap 1062 at (or towards) the back (or a rear) of the patient's head (e.g., below the occiput, adjacent the nape, or below the ear). In the illustrated example, the tube anchor 1092 forms a loop to receive the air delivery tube therein. The air delivery tubes 1080 are feed through the tube anchor 1092 which aids in supporting the weight of the air delivery tubes 1080. It may be preferred to position the tube connection at the back of the patient's head to increase the patient's range of motion and prevent the tube being pulled to the side.

In the illustrated example, the mask (e.g., the back panel 20-1 and front panel (removed for illustration purposes) is made of textile. Further, the mask is held on the patient's face with only a single strap 1062. As the textile mask of the illustrated example may be less rigid that other mask systems (e.g., those having plastic frames), provision of the tube anchor 1092 to aid in supporting the weight of the air delivery tube may enhance performance of the textile mask system.

It will be understood that the tube anchor may be positioned at other locations along the bottom strap 1062. Further, it may be possible to provide the tube anchor on other headgear straps such as those shown and described in FIGS. 18-2 to 18-5 for example.

6.1 Air Delivery Tube

Figures 1A, 21:
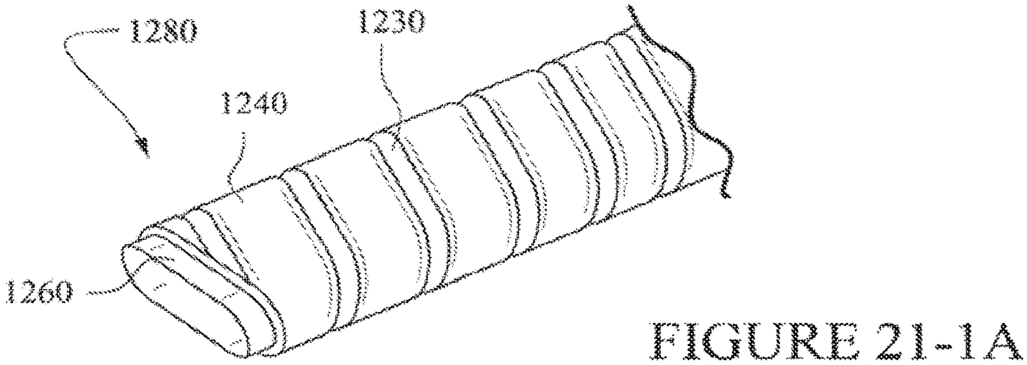
Figures 1B, 21:
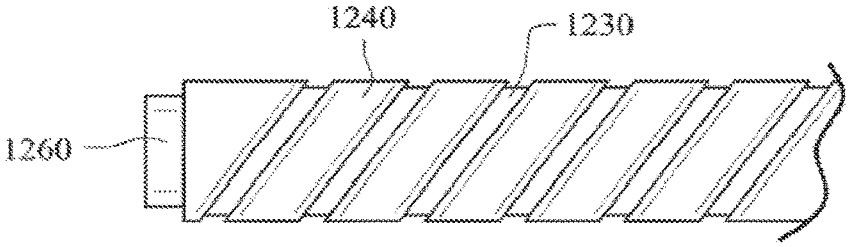
Figures 2, 21:
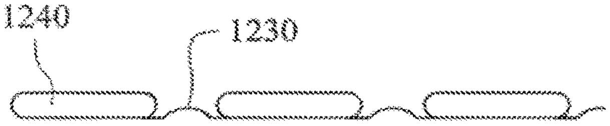

Referring to FIGS. 21-1A to 21-2, an air delivery tube 1280 having a support structure provided thereon is shown. The support structure may provide shape, form and occlusion resistance to the tube. Tubes, some having support structures, are described in PCT Application PCT/AU2012/000667, filed Jun. 8, 2012, which is incorporated herein by reference in its entirety. The tubes described in PCT/AU2012/000667 may be implemented into any of the examples described in this application.

In the example shown in FIG. 21-1A to 21-2, a tube having a tube wall 1230 and a support structure 1240 provided to the tube wall 1230 is shown. The tube has a capsule or race track-shaped cross-section; although other shapes may be used. (e.g., oval, rectangular having rounded edges, a structure having four sides (i.e. two opposing sides that are substantially longer than the other two opposing sides). The tube wall 1230 may comprise a flexible tape. The support structure 1240 wraps around the tube wall 1230 in the manner of a helix. The support structure 1240 (e.g., ribs) is relatively wide as compared to the exposed tube wall 1230 sections. A tube cuff 1260 may be provided at ends of the tube to connect to a cuff disposed on the mask and/or a flow generator.

The relatively wide support structure 1240 may be desirable for tube in sections close to the patient's face, since the wider support structure provides fewer strips of material which may mark the patient's face. It may also be more comfortable for the patient to lie on a tube with a flatter profile as compared to a round profile.

For example, in the arrangement shown in FIGS. 19-1 to 19-5, the tube arrangement shown in FIG. 21-1A may extend only from the mask around the patient's neck to the tube anchor 1092; thus, this section of the tube is not required to bend in a severe manner and may be suitable for this section. The width of the support structure 1240 may be reduced in tube sections further away from the patient's face to increase flexibility of the tube.

Figures 3A, 21:
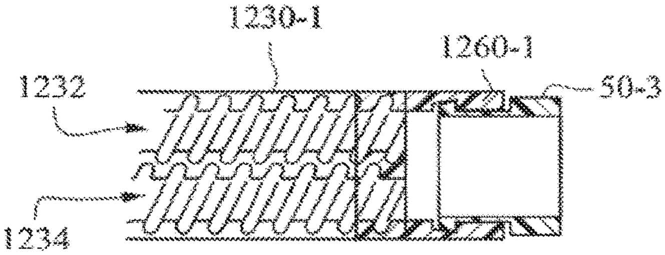
Figures 3B, 21:
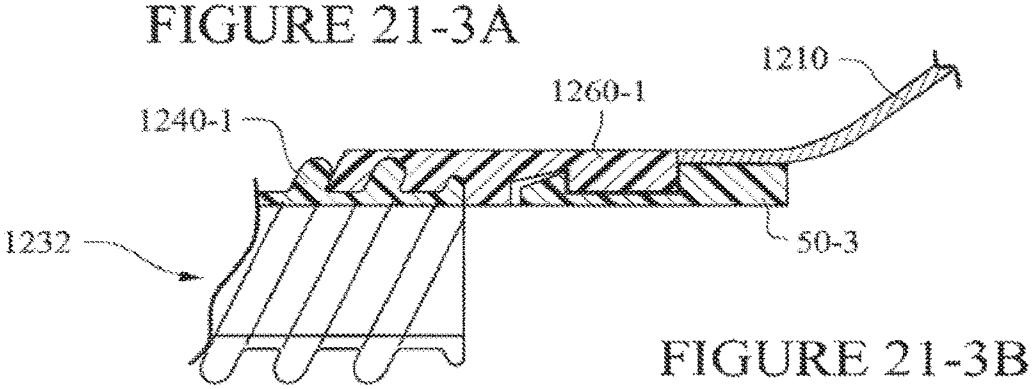
Figures 4, 21:
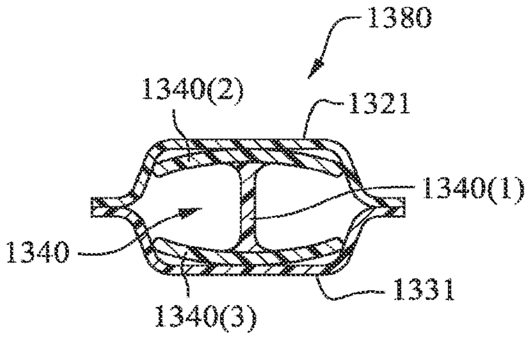

Turning to FIGS. 21-3A and 21-3B, a tube wall 1230-1 encloses two channels 1232, 1234 which are configured to allow passage of breathable gas therein. A support structure 1240-1 (e.g., ribs) is provided to the tube wall 1230-1. A tube cuff 1260-1 may engage the support structure 1240-1 and extend therefrom for connection to a cuff 50-3 which is attached to a mask 1210. The tube cuff 1260-1 and the cuff 50-3 may form a dovetail connection for example, or any other suitable connection. Tube wall 1230-1 may be an optional component. Tube wall 1230-1 may be, for example, fabric or a plastic extrusion. The tube cuff 1260-1 may be over-molded onto the tube wall 1230-1.

Referring to FIG. 21-4, an air delivery tube 1380 includes first and second tube covers 1321, 1331 that cooperate to form the tube. The tube covers 1321, 1331 may include an inner layer of a film laminate (e.g., polyurethane or medical grade film) and an outer layer of a textile or fabric (e.g., synthetic or specified fabric). A rigid, or semi-rigid support substrate 1340 may be inserted into the tube to provide crush resistance and form. In the illustrated example, the support substrate 1340 includes a central base 1340(1) and upper and lower generally curved arms 1340(2), 1340(3) extending from respective sides of the base.

Figures 5A, 21:
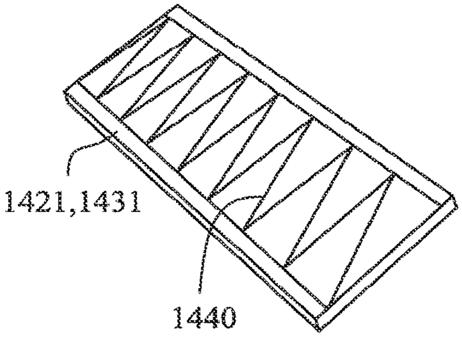
Figures 5B, 21:
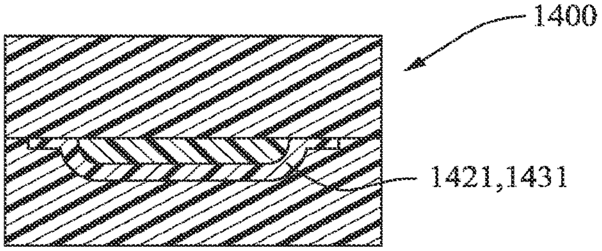
Figures 5C, 21:
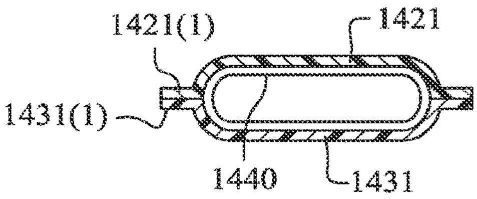
Figures 5D, 21:
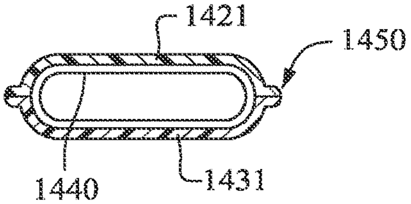
Figures 6A, 21:
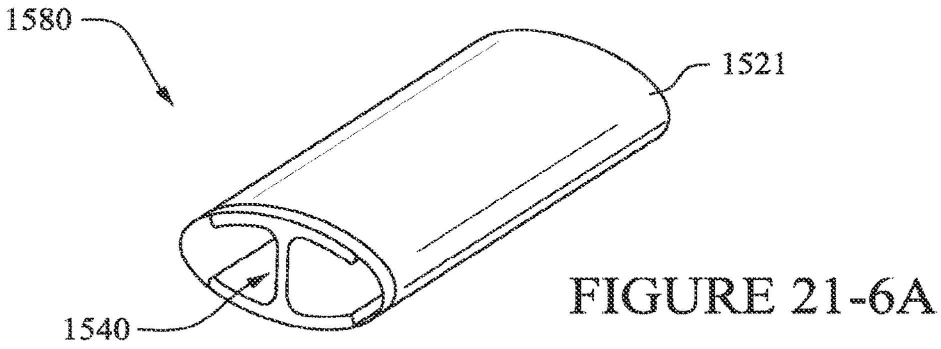
Figures 6B, 21:
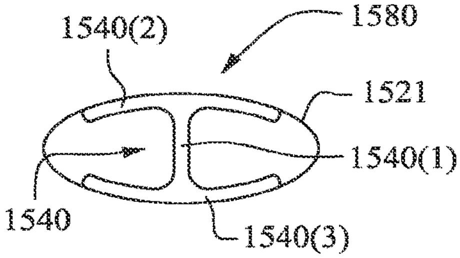
Figures 6C, 21:
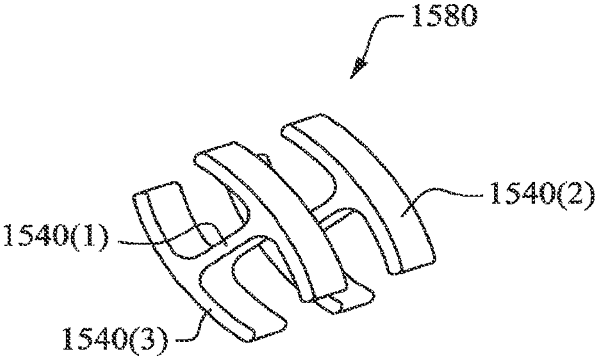
Figures 7A, 21:
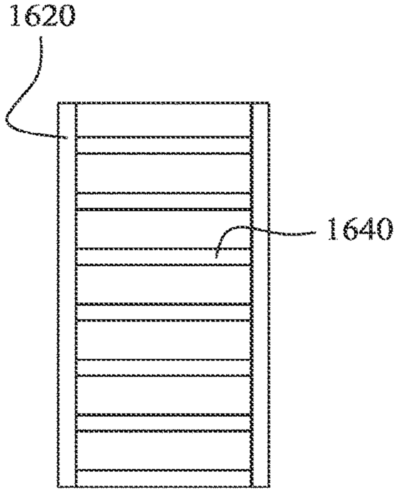
Figures 7B, 21:
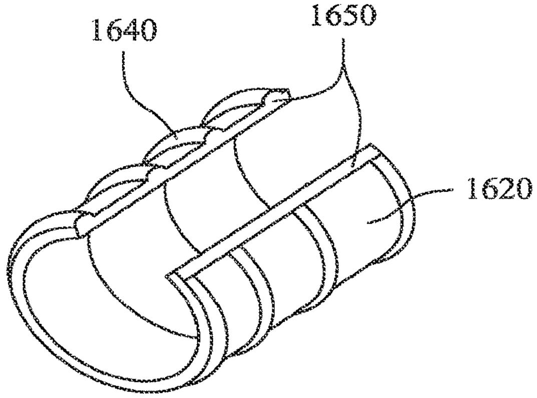
Figures 8A, 21:
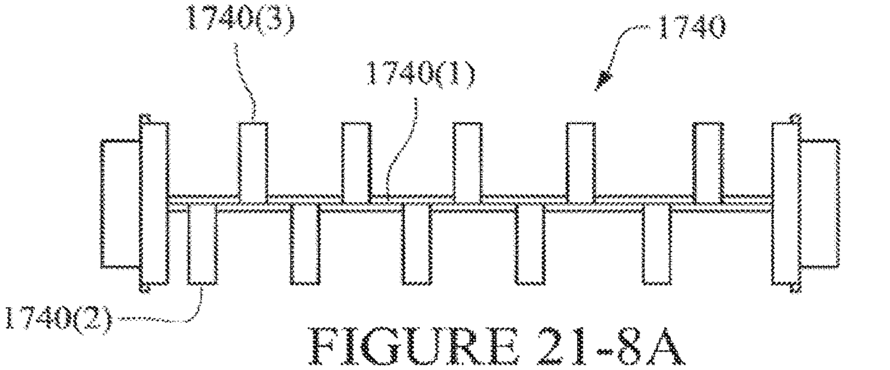
Figures 8B, 21:
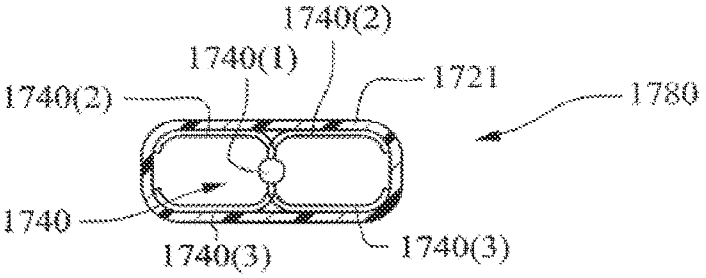
Figures 9, 21:
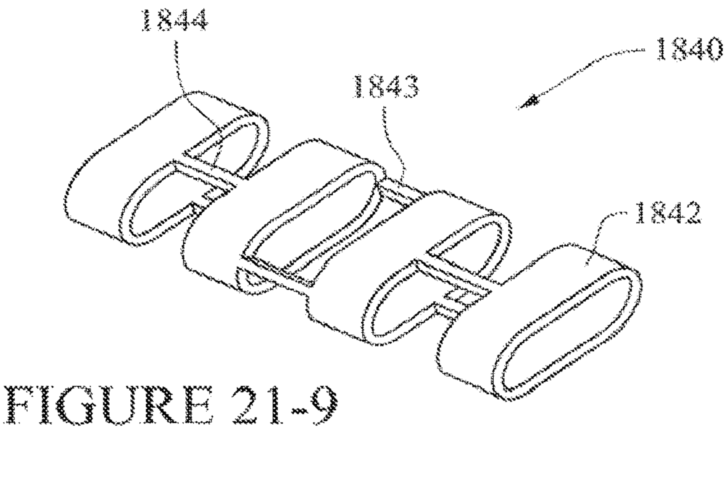
Figures 10, 21:
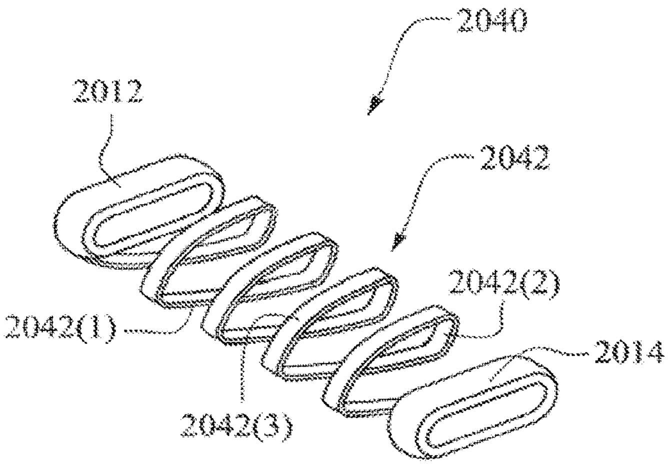
Figures 11, 21:
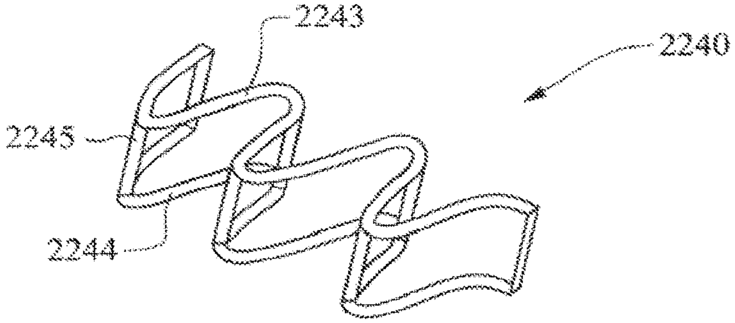

Referring to FIGS. 21-5A to 21-5D, a tube cover 1421, 1431 in sheet form may have a support structure 1440 formed thereon (e.g., co-extruded, printed, overmolded, heat formed). Each tube cover 1421, 1431 may be placed in a tool 1400 which thermoformed the tube covers 1421, 1431 along with the support structure 1440 into a half tube shape. The two tube covers 1421, 1431 are then welded together, as shown in FIG. 21-5C. After welding, flanges 1421(1), 1431(1) of the joined tube covers 1421, 1431 may be ultrasonically cut thereby leaving a rounded end 1450, as shown in FIG. 21-5D.

Turning to FIGS. 21-6A to 21-6C, an air delivery tube 1580 includes a tube cover 1521 that may have a rigid or semi-rigid support substrate 1540 inserted therein. In the illustrated example, the support substrate 1540 includes a central base 1540(1) and upper and lower generally curved arms 1540(2), 1540(3) extending from respective sides of the base.

In another example, shown in FIGS. 21-7A and 21-7B, a tube sheet 1620 may be provided with a support structure 1640 to form an integrated one piece composite self-supporting textile conduit. The tube sheet 1620 is preferably a fabric that is air-resistant or completely air-tight (e.g., may include film laminate or air-tight layer). The support structure 1640 may comprise a rib structure including one or more rib formations. The tube sheet 1620 may be inserted into a relatively flat tool and the support structure 1640 may be molded in a pattern on top of the tube sheet 1620. In another example, the support structure maybe overmolded onto the tube sheet 1620.

The tube sheet 1620 may include fasteners 1650 attached to end portions of the tube sheet such that the tube sheet may be rolled into a tube and the fasteners 1650 connected to retain the tube shape as an air delivery tube. It is noted that the ends of the tube sheet may be joined by other means.

Figures 5, 6, 7, 8, 8A:
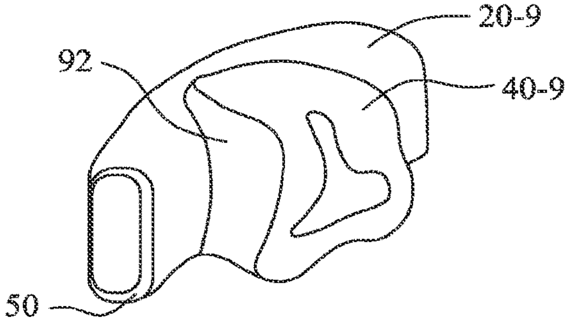
Figures 5, 6, 7, 8, 8B:
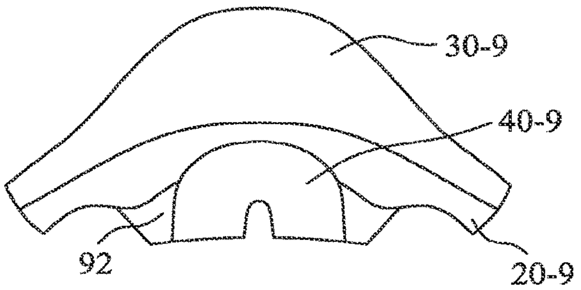
Figures 5, 6, 7, 8, 8C:
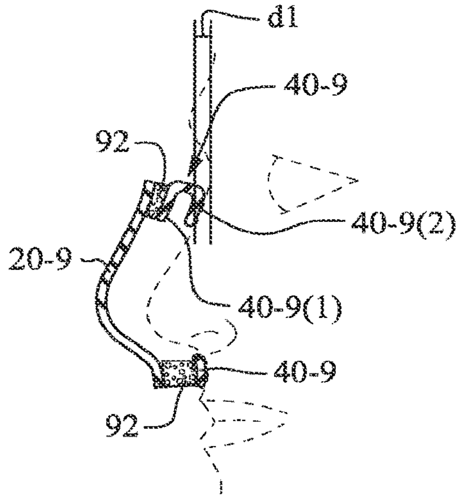
Figures 5, 6, 7, 8, 8D:
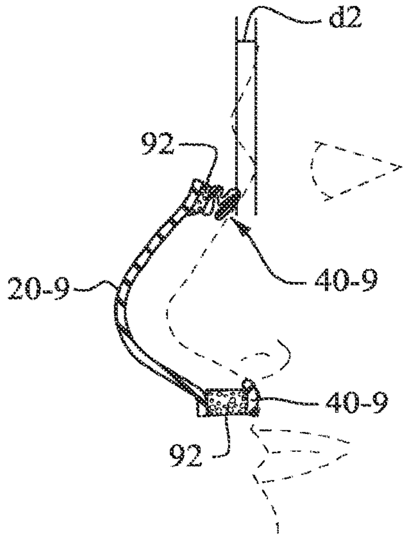
Figures 1, 6:
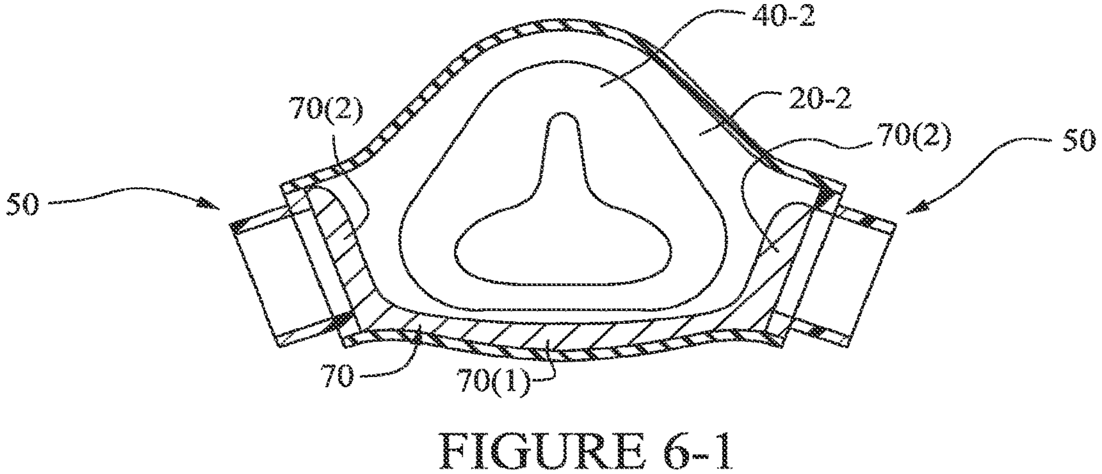
Figures 1, 7:
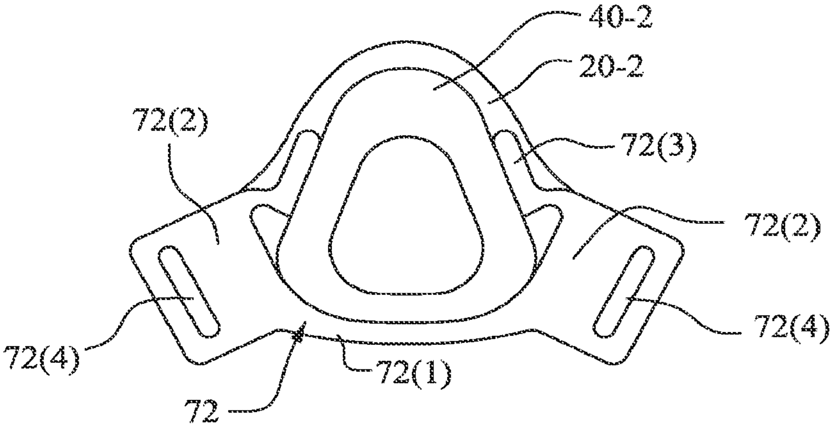
Figures 2, 7:
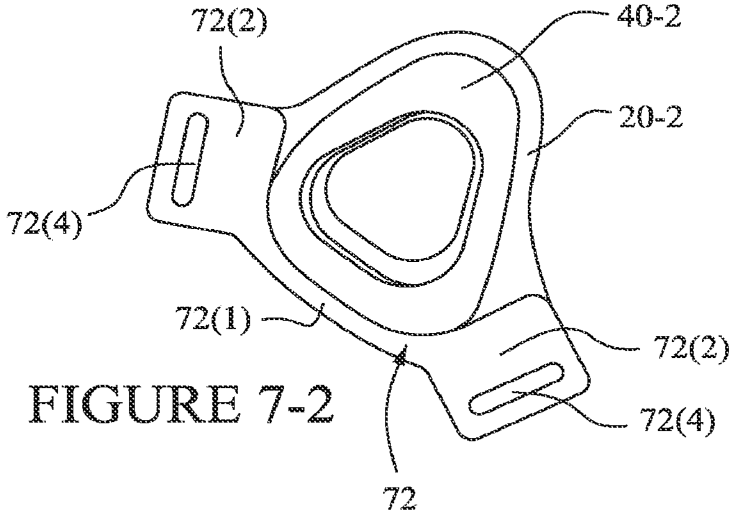
Figures 3, 7:
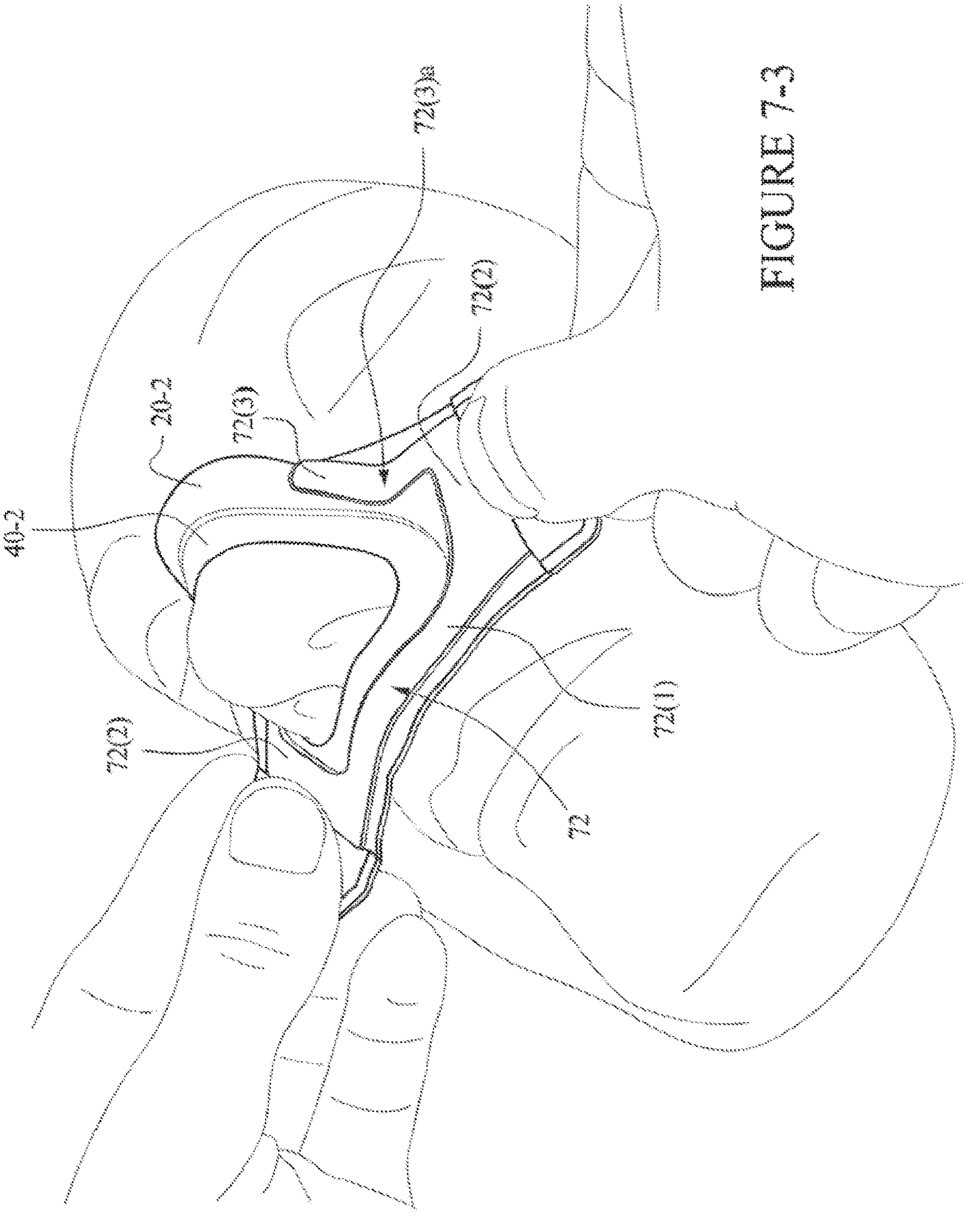
Figures 1, 8:
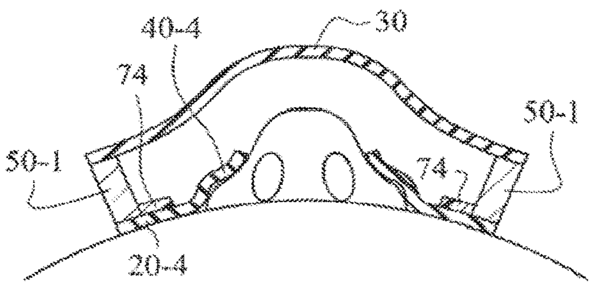
Figures 2, 8:
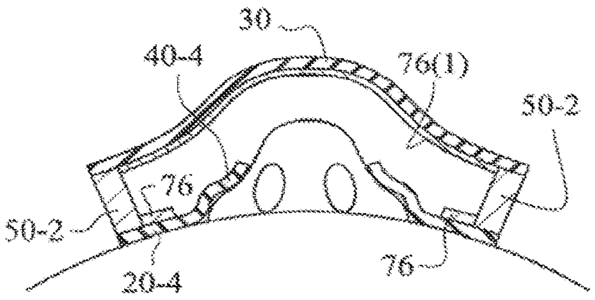
Figure 9:
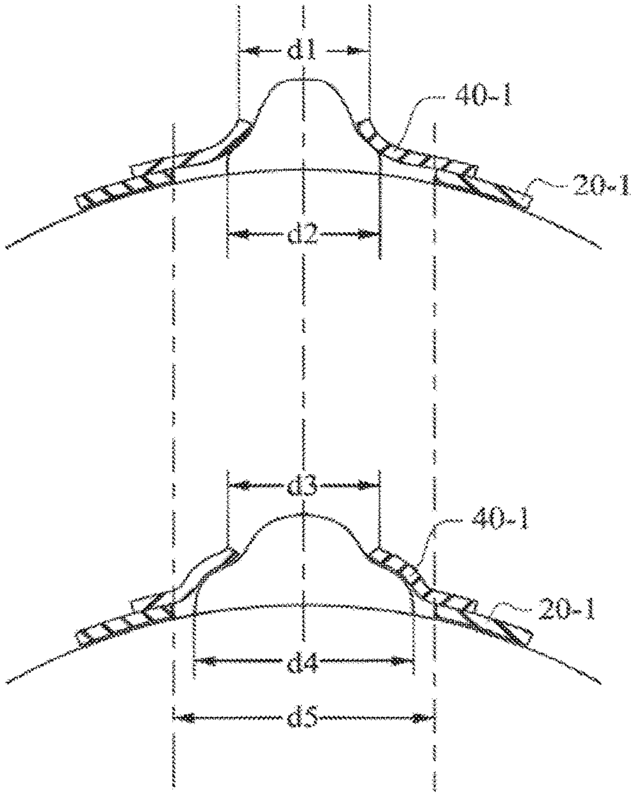
Figures 1, 10:
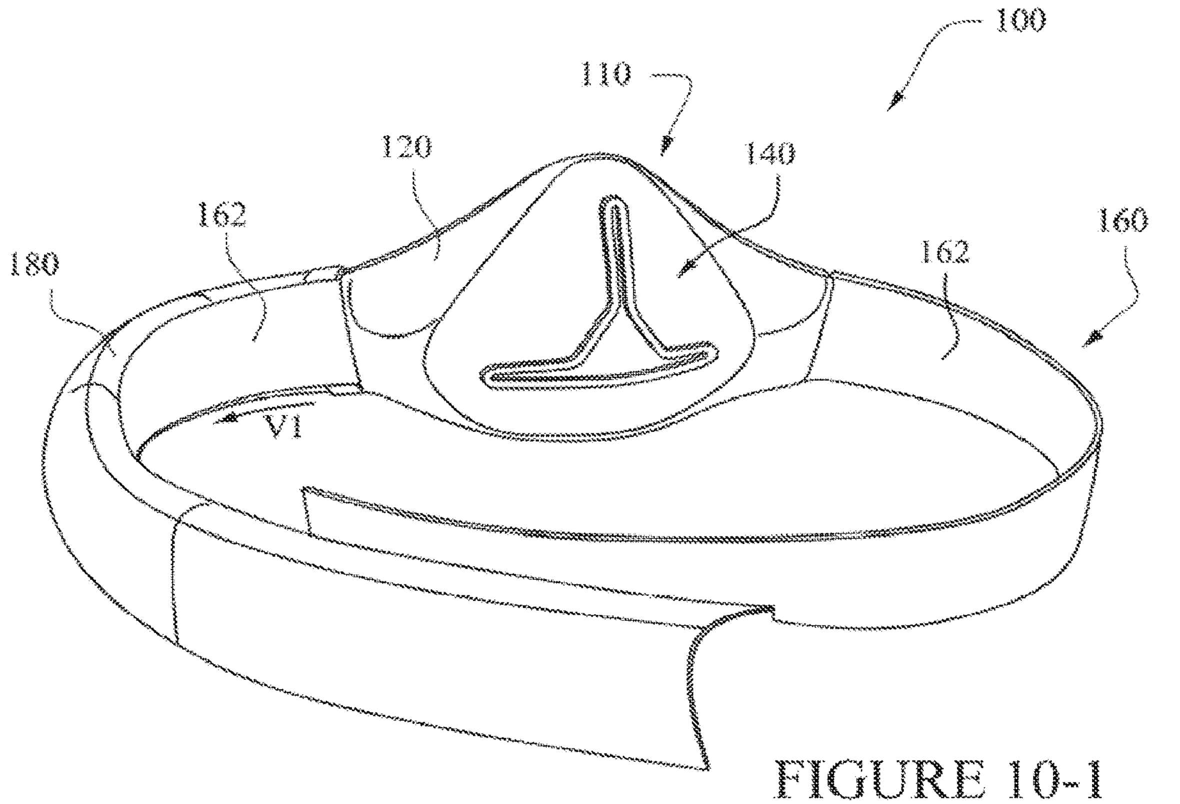
Figures 2, 10:
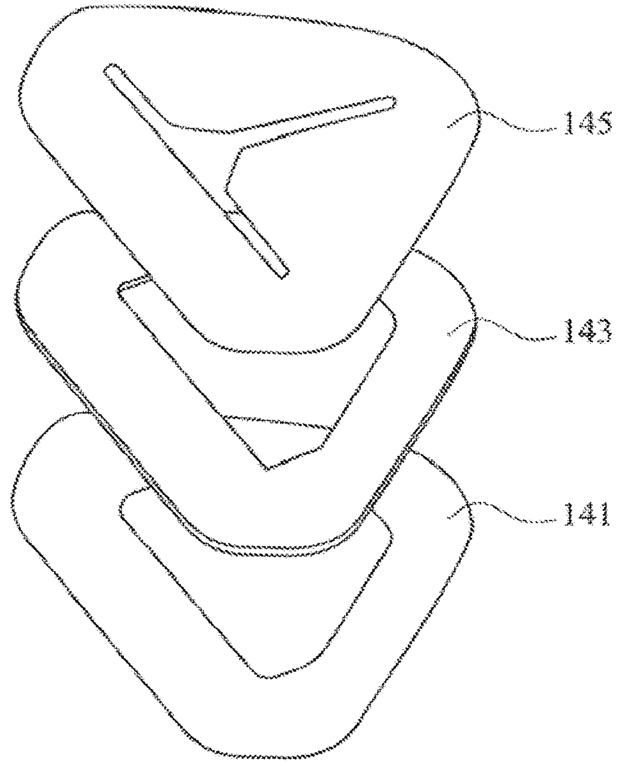
Figures 1, 11:
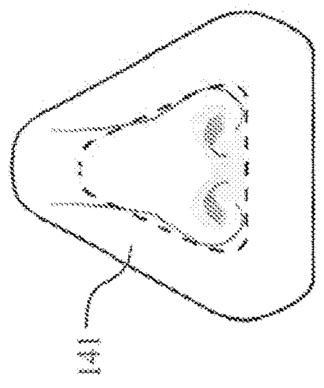
Figures 2, 11:
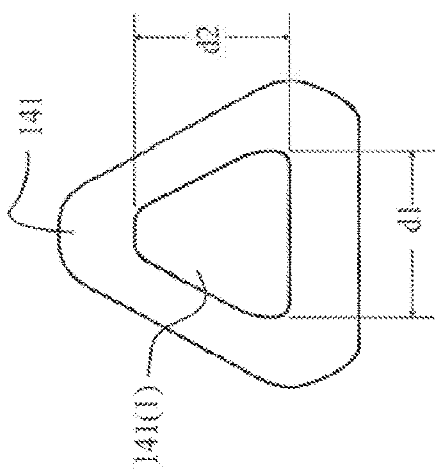
Figures 3, 11:
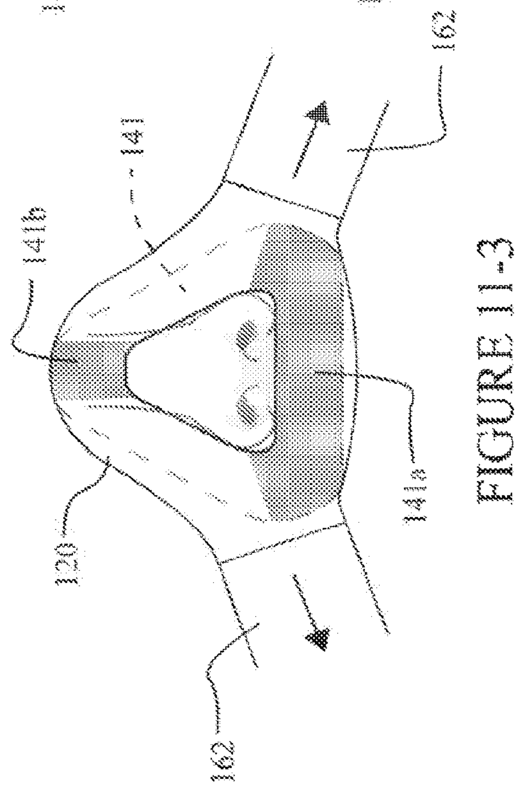
Figures 4, 11:
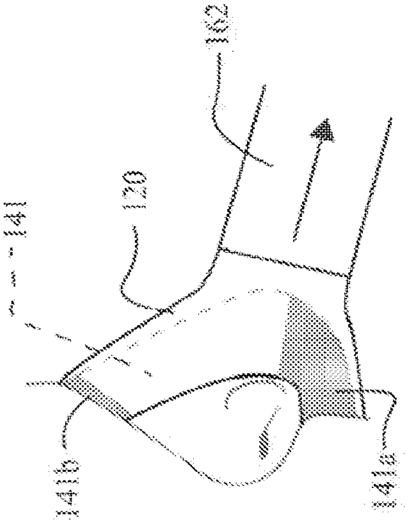
Figures 1, 12:
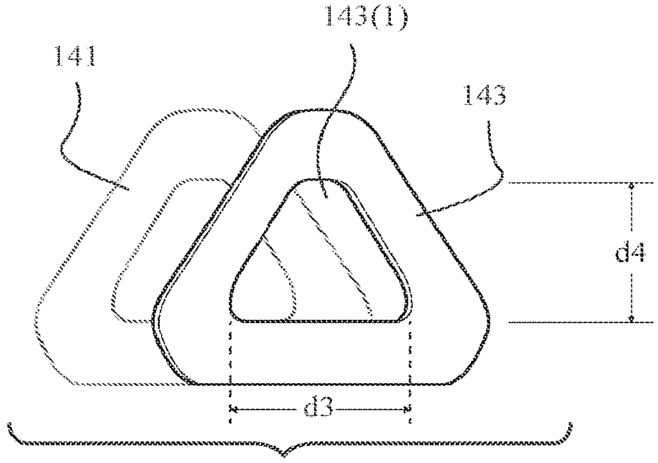
Figures 2, 12:
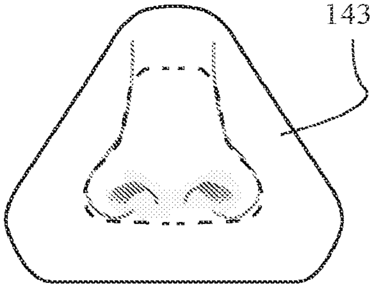
Figures 3, 12:
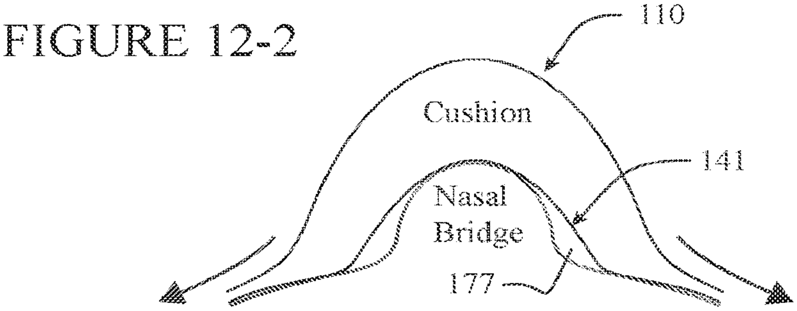
Figures 4, 12:
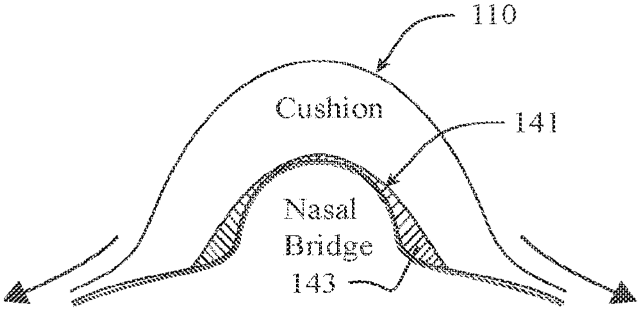
Figures 1, 13:
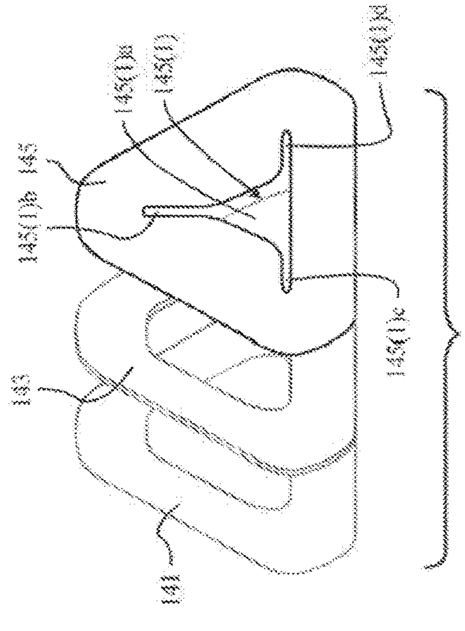
Figures 2, 13:
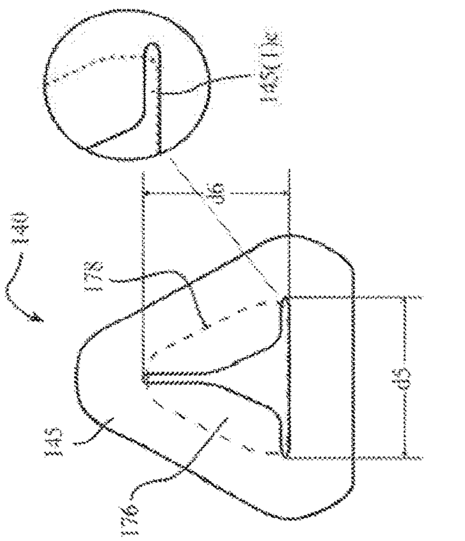
Figures 3, 13:
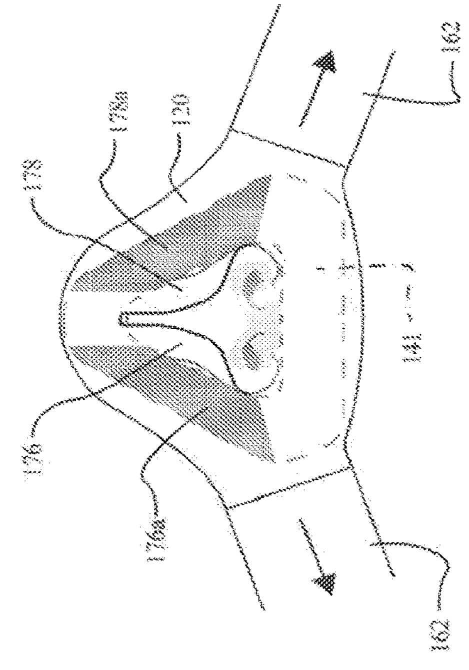
Figures 4, 13:
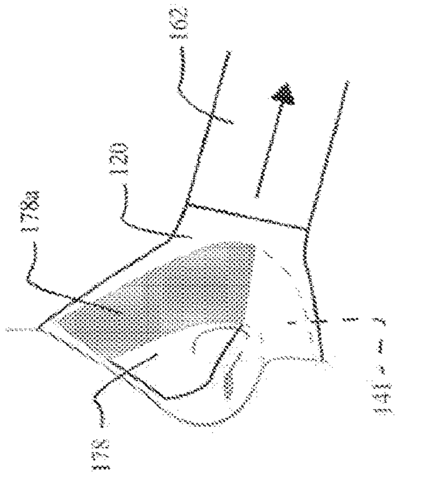

Similar to the tube 1580 shown in FIGS. 21-6A to 21-6C, a tube 1780 is shown in FIGS. 21-8A and 21-8B. A tube cover 1721 may have a rigid or semi-rigid support substrate 1740 inserted therein. In the illustrated example, the support substrate 1740 includes a central base 1740(1) and upper and lower generally curved arms 1740(2), 1740(3) extending from respective sides of the base. The arms extending from one side of the central base 1740(1) may be staggered with respect to the arms extending from the other side of the central base 1740(1).

In another example, as shown in FIG. 21-9, a support substrate 1840 includes a series of body portions 1842 connected by alternating sets of lateral links 1843 and central links 1844. The alternating links 1843, 1844 are designed to provide structural support to the support substrate 1840 in both the horizontal and vertical directions, while at the same time providing flexibility.

In another example, shown in FIG. 21-10, a support substrate 2040 includes a pair of body portions 2012, 2014 connected by winding connector 2042. The winding connector 2042 includes a series of flat legs 2042(1) extending along a bottom of the support substrate 2040 in a generally flat manner. The flat legs 2042(1) may extend at an angle. A series of vertical legs 2042(2) connect to end portions of respective flat legs and extend generally in a vertically manner so as to provide a space through a central portion of the winding connector 2042 that will function as an air passageway. A series of connecting legs 2042(3) may extend at an angle to interconnect the vertical legs 2042(2) with an adjacent flat leg 2042(1).

Figures 12A, 21:
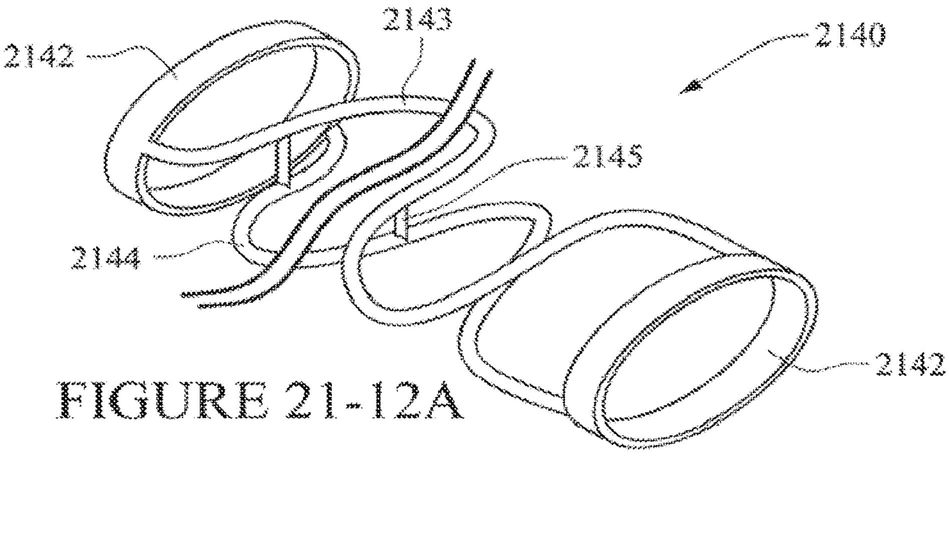
Figures 12B, 21:
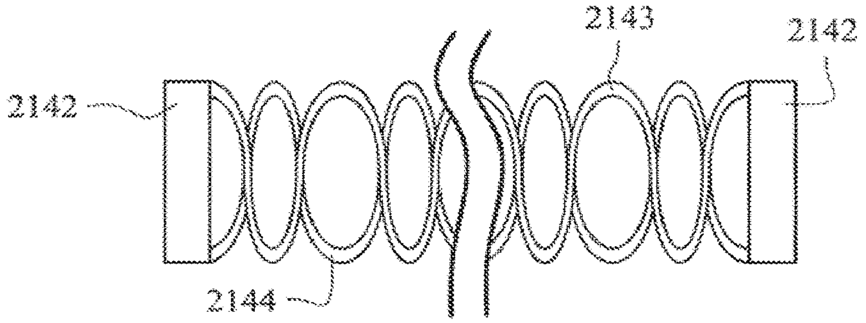
Figures 13, 21:
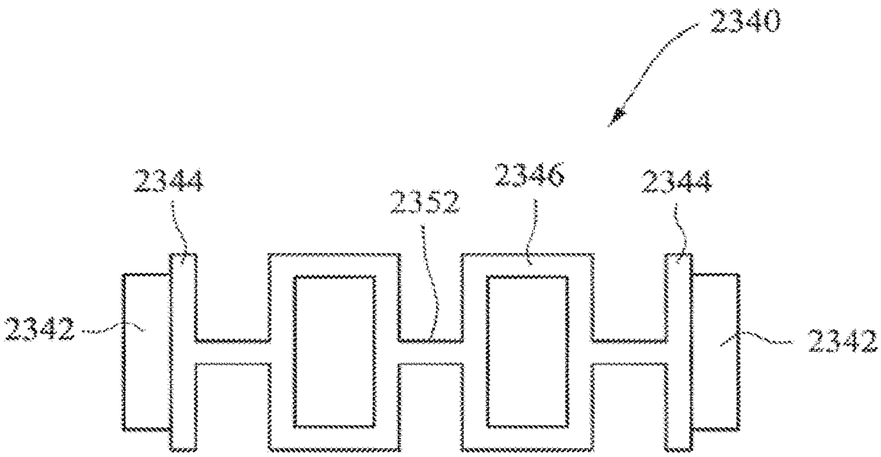

In yet another example shown in FIGS. 21-12A and 21-12B, a support substrate 2140 includes two support members 2142 connected by a first wave member 2143 and a second wave member 2144. The first and second wave members have a matching or opposite mirror image sinusoidal shape (i.e. the wave members 2143, 2144 are out of phase such that the peak of one of the wave members is aligned with a trough of the other wave member) and are connected to each support member 2142 at opposite points so as to provide a space between the wave members 2143, 2144 that will function as an air passageway. The wave members 2143, 2144 are described as having an identical shape; however, one skilled in the art would recognize that the wave members could have different shapes while still managing to provide structural support, form and/or crush resistance. Any suitable number of wave members could also be connected between the support members 2142.

Intermediate support members 2142 could also be provided. Preferably, wave members 2143, 2144 may be curved about the longitudinal axis of the tube (at the apex of the curves of the waves) to form the rounded edges of the tube i.e. to create capsule cross section.

A plurality of struts 2145 may extend between and connect the first 2143 and second 2144 wave members to provide structural support.

Referring to FIG. 21-11, this example shows a similar technology to that shown in FIGS. 21-12A and 21-12B; however, the first wave member 2243 and a second wave member 2244 are in phase i.e. the peaks and troughs of each wave are aligned. In addition, struts 2245 may be provided at the peaks and troughs of each wave instead of being positioned intermediate the peaks and troughs of each wave as shown in FIGS. 21-12A and 21-12B.

Referring to FIG. 21-13, a support substrate 2340 includes a series of body portions 2346 connected by links 2352. The support substrate 2340 is similar to the support substrate 1840 in FIG. 21-9 and is similarly designed to provide support while allowing flexibility. In contrast to the support substrate 1840, the support substrate 2340 may include openings or cutouts in the body portions 2346 which may reduce weight and/or provide increased flexibility. End portions 2344 may be connected to cuffs or connectors 2342 which may be configured to connect to a cuff of a cushion and/or a flow generator.

While the technology has been described in connection with several examples, it is to be understood that the technology is not to be limited to the disclosed examples, but on the contrary, is intended to cover various modifications and equivalent arrangements included within the spirit and scope of the technology. Also, the various examples described above may be implemented in conjunction with other examples, e.g., one or more aspects of one example may be combined with one or more aspects of another example to realize yet other examples. Further, each independent feature or component of any given assembly may constitute an additional example. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask system for delivering pressurized breathable gas to a patient for treatment of sleep disordered breathing, comprising:

a mask including:

a non-patient-contacting side comprising a first flexible material, the non-patient-contacting side forming an anterior portion of the mask in use, the first flexible material including a pair of lateral ends forming cuff connecting surfaces having curved shapes adapted to, respectively, engage and form at least part of an annular seal around a pair of cuffs adapted to connect to a pair of air delivery conduits;

a patient-contacting side comprising a second flexible material, the patient-contacting side forming a posterior portion of the mask in use, the non-patient contacting side and the patient-contacting side together at least partially forming a cavity adapted to be in fluid communication with the patient's airway such that both the non-patient contacting side and the patient-contacting side are exposed to therapeutic pressurized breathable gas in use; and a textile seal member adapted to sealingly engage the patient's face in use, the textile seal member being formed as part of the patient-contacting side and including a first layer of textile and a second layer of silicone, wherein the textile seal member includes an opening formed therein and configured to deliver breathable gas to the patient's airways in use, wherein the first flexible material of the non-patient contacting side of the mask comprises silicone forming an anterior-most portion of the mask, and wherein an insertable vent component is sealingly attached to the silicone of the non-patient contacting side to, in use, expel exhaust gases to atmosphere.

2. The mask system of claim 1, wherein the layer of silicone is an air impermeable layer.

3. The mask system of claim 1, wherein the non-patient contacting side of the mask includes a front panel, and the patient contacting side of the mask includes a back panel.

4. The mask system of claim 3, wherein the front panel comprises the silicone.

5. The mask system of claim 3, wherein the textile seal member has increased ability to conform to the patient's facial features as compared to the back panel.

6. The mask system of claim 3, wherein the textile seal member is thinner than other portions of patient-contacting side.

7. The mask system of claim 3, wherein the front panel and the back panel sealingly engage one another along respective outer perimeters of the front panel and the back panel to together at least partially form the cavity.

8. The mask system of claim 3, wherein the front panel is curved from an upper end portion to a lower end portion thereof to at least partially form the cavity.

9. The mask system of claim 3, wherein the back panel is curved from an upper end portion to a lower end portion thereof to at least partially form the cavity.

10. The mask system of claim 3, wherein the back panel is configured to flex to conform to the curvature of the patient's face in use.

11. The mask system of claim 3, wherein the mask has a headgear connection point on each side of the mask, wherein the front panel is curved from an upper end portion to a lower end portion thereof to at least partially form the cavity, wherein the back panel is curved from an upper end portion to a lower end portion thereof to at least partially form the cavity, wherein the back panel is configured to flex to conform to the curvature of the patient's face, and wherein the textile seal member is stretchable.

12. The mask system of claim 1, further comprising a pair of cuffs connected, respectively, to at least the cuff connecting surfaces of the non-patient-contacting side.

13. The mask system of claim 1, wherein the mask includes at least one cuff adapted to be coupled to an air delivery tube.

14. The mask system of claim 13, wherein the cuff includes vent openings formed therein to expel exhaust gases to atmosphere.

15. The mask system of claim 1, wherein the mask has a headgear connection point on each side of the mask.

16. The mask system of claim 1, further comprising headgear coupled to the mask and configured to support the mask in position on the patient's face in use, the headgear including at least one strap.

17. The mask system of claim 16, wherein the strap includes a fabric and a rigidizer is provided to the strap to add rigidity to the strap.

18. The mask system of claim 1, wherein the textile seal member is stretchable and elastic.

19. The mask system of claim 1, wherein the textile seal member is configured to apply a spring force against the patient's face in use.

20. The mask system of claim 1, wherein the mask is a nasal mask.

* * * * *